(12) United States Patent
Coffman et al.

(10) Patent No.: US 12,263,249 B2
(45) Date of Patent: Apr. 1, 2025

(54) FORMATION OF PARTICLES INCLUDING AGENTS

(71) Applicant: Elektrofi, Inc., Boston, MA (US)

(72) Inventors: Chase Spenser Coffman, Newton, MA (US); Lyndon Fitzgerald Charles, Jr., Medford, MA (US); Paul Brown, Boston, MA (US); Daniel Benjamin Dadon, East Boston, MA (US); Lisa Liu, Somerville, MA (US); Cory Robinson, Cambridge, MA (US); Dale Arlington Thomas, III, Hampden, ME (US)

(73) Assignee: Elektrofi, Inc., Boston, MA (US)

( * ) Notice: Subject to any disclaimer, the term of this patent is extended or adjusted under 35 U.S.C. 154(b) by 670 days.

(21) Appl. No.: 17/364,770

(22) Filed: Jun. 30, 2021

(65) Prior Publication Data

US 2021/0322317 A1     Oct. 21, 2021

Related U.S. Application Data

(62) Division of application No. 16/633,097, filed as application No. PCT/US2018/043774 on Jul. 25, 2018, now Pat. No. 11,077,059.

(Continued)

(51) Int. Cl.
   *A61K 9/14*         (2006.01)
   *B01J 2/06*         (2006.01)

(52) U.S. Cl.
   CPC .............. *A61K 9/145* (2013.01); *A61K 9/146* (2013.01); *B01J 2/06* (2013.01)

(58) Field of Classification Search
   CPC ......... A61K 9/145; A61K 9/146; B01J 13/02; B01J 2/06
   See application file for complete search history.

(56) References Cited

U.S. PATENT DOCUMENTS

| 3,013,007 A | 12/1961 | Dale et al. |
| 3,882,036 A | 5/1975 | Krezanoski et al. |

(Continued)

FOREIGN PATENT DOCUMENTS

| CN | 1750811 A | 3/2006 |
| EP | 0677332 A2 | 10/1995 |

(Continued)

OTHER PUBLICATIONS

Allahham, D. et al., "Development and application of a microcapillary rheometer for in-vitro evaluation of parenteral injectability," Journal of Pharmacy and Pharmacology, vol. 56; 709-716 (2004).

(Continued)

*Primary Examiner* — Carlos A Azpuru
(74) *Attorney, Agent, or Firm* — Hamilton, Brook, Smith & Reynolds, P.C.

(57) ABSTRACT

The invention provides methods for the preparation of particles including one or more agents, e.g., therapeutic or diagnostic agents. The particles can be formed by creating droplets of a first liquid, e.g., including an agent, and removing the first liquid, e.g., through its dispersal in a second liquid and/or evaporation, to solidify the droplets. Advantageously, the process of forming the particles does not significantly alter the structure or activity of the agents and may enhance the stability of the agents. For example, the particles may be stored for long periods of time without significant loss of activity, and in some embodiments, without the need for refrigeration. These particles may be used to generate stabilized pharmaceutical compositions for storage or other logistical purposes, pharmaceutical suspensions, pharmaceutical powder formulations (e.g., inhalable powders, injectable powders), creams or other topical pastes, nutraceuticals, or cosmetics.

19 Claims, 40 Drawing Sheets

Related U.S. Application Data

(60) Provisional application No. 62/676,195, filed on May 24, 2018, provisional application No. 62/536,746, filed on Jul. 25, 2017.

(56) References Cited

U.S. PATENT DOCUMENTS

| | | |
|---|---|---|
| 4,172,896 A | 10/1979 | Uno et al. |
| 4,531,056 A | 7/1985 | Labowsky et al. |
| 5,358,970 A | 10/1994 | Ruff et al. |
| 5,427,798 A | 6/1995 | Ludwig et al. |
| 5,541,231 A | 7/1996 | Ruff et al. |
| 5,595,721 A | 1/1997 | Kaminski et al. |
| 5,612,055 A | 3/1997 | Bedford et al. |
| 5,677,180 A | 10/1997 | Robinson et al. |
| 5,731,000 A | 3/1998 | Ruff et al. |
| 5,736,137 A | 4/1998 | Anderson et al. |
| 5,763,493 A | 6/1998 | Ruff et al. |
| 5,840,731 A | 11/1998 | Mayer et al. |
| 6,095,134 A | 8/2000 | Sievers et al. |
| 6,110,973 A | 8/2000 | Young |
| 8,013,022 B2 | 9/2011 | Deangelo et al. |
| 8,512,754 B2 | 8/2013 | Needham |
| 8,728,525 B2 | 5/2014 | Brown et al. |
| 8,779,094 B2 | 7/2014 | Johnston et al. |
| 8,939,388 B1 | 1/2015 | Beetz et al. |
| 9,259,701 B2 | 2/2016 | Palmer et al. |
| 9,364,542 B2 | 6/2016 | Chang |
| 9,643,996 B2 | 5/2017 | Petrel et al. |
| 11,077,059 B2 | 8/2021 | Coffman et al. |
| 11,459,376 B2 | 10/2022 | Brown et al. |
| 11,510,995 B2 | 11/2022 | Sanchez Martin et al. |
| 11,654,112 B2 | 5/2023 | Coffman et al. |
| 11,717,488 B2 | 8/2023 | Brown et al. |
| 11,795,429 B2 | 10/2023 | Bitterfield et al. |
| 12,115,262 B2 | 10/2024 | Coffman et al. |
| 2002/0081732 A1 | 6/2002 | Bowlin et al. |
| 2003/0055010 A1 | 3/2003 | De Haan |
| 2004/0197469 A1 | 10/2004 | Lyons et al. |
| 2005/0186183 A1 | 8/2005 | Deangelo et al. |
| 2006/0147400 A1 | 7/2006 | Piot |
| 2008/0026068 A1 | 1/2008 | Brown et al. |
| 2008/0095849 A1 | 4/2008 | Wu et al. |
| 2009/0035381 A1 | 2/2009 | Stankus et al. |
| 2009/0274765 A1 | 11/2009 | Beduneau et al. |
| 2010/0092526 A1 | 4/2010 | Baker et al. |
| 2010/0092778 A1* | 4/2010 | Watanabe ............ A61K 9/1658 264/14 |
| 2010/0330169 A1 | 12/2010 | Bunick et al. |
| 2012/0076800 A1 | 3/2012 | Dai et al. |
| 2012/0157591 A1 | 6/2012 | Rufner et al. |
| 2013/0256931 A1 | 10/2013 | Palmer et al. |
| 2014/0052020 A1 | 2/2014 | Allen et al. |
| 2014/0262694 A1 | 9/2014 | Knigge |
| 2014/0263694 A1 | 9/2014 | Lin et al. |
| 2014/0271843 A1 | 9/2014 | Ma et al. |
| 2014/0288282 A1 | 9/2014 | Petrel et al. |
| 2014/0303356 A1 | 10/2014 | Gramer et al. |
| 2014/0308270 A1 | 10/2014 | Lobo et al. |
| 2014/0348852 A1 | 11/2014 | Vos et al. |
| 2014/0378370 A1 | 12/2014 | Johnston et al. |
| 2014/0378655 A1 | 12/2014 | Anderson |
| 2015/0079395 A1 | 3/2015 | Cruise et al. |
| 2015/0157576 A1 | 6/2015 | Shum et al. |
| 2016/0128944 A1 | 5/2016 | Chawrai et al. |
| 2016/0250329 A1 | 9/2016 | Bukrinski et al. |
| 2016/0271064 A1 | 9/2016 | Sell et al. |
| 2018/0333493 A1 | 11/2018 | Shenoy |
| 2019/0374470 A1 | 12/2019 | Coffman et al. |
| 2020/0253875 A1 | 8/2020 | Coffman et al. |
| 2021/0220289 A1 | 7/2021 | Coffman et al. |
| 2021/0309724 A1 | 10/2021 | Brown et al. |
| 2021/0315827 A1 | 10/2021 | Brown et al. |
| 2021/0403599 A1 | 12/2021 | Badovinac-Crnjevic et al. |
| 2022/0211627 A1 | 7/2022 | Arrighi et al. |
| 2022/0389084 A1 | 12/2022 | Brown et al. |
| 2023/0065628 A1 | 3/2023 | Auer et al. |
| 2023/0094393 A1 | 3/2023 | Charles et al. |
| 2023/0181473 A1 | 6/2023 | Auer et al. |
| 2023/0338299 A1 | 10/2023 | Paul et al. |
| 2023/0355530 A1 | 11/2023 | Coffman et al. |
| 2024/0255517 A1 | 8/2024 | Carter et al. |
| 2024/0270864 A1 | 8/2024 | Brown et al. |
| 2024/0293332 A1 | 9/2024 | Brown et al. |
| 2024/0415782 A1 | 12/2024 | Coffman et al. |

FOREIGN PATENT DOCUMENTS

| | | |
|---|---|---|
| EP | 2773330 B1 | 9/2020 |
| JP | 2008-266128 A | 11/2008 |
| JP | 2010-524948 A | 5/2010 |
| JP | 2011-079747 A | 4/2011 |
| JP | 2013-166100 A | 8/2013 |
| JP | 2014-058466 A | 4/2014 |
| JP | 2014-129357 A | 7/2014 |
| WO | 99/11196 A1 | 3/1999 |
| WO | 03/35301 A1 | 5/2003 |
| WO | 2006/087354 A2 | 8/2006 |
| WO | 2008/062908 A1 | 5/2008 |
| WO | 2008/092084 A2 | 7/2008 |
| WO | 2010/044867 A1 | 4/2010 |
| WO | 2010/082543 A1 | 7/2010 |
| WO | 2011/131943 A2 | 10/2011 |
| WO | 2012/042274 A1 | 4/2012 |
| WO | 2014/057424 A2 | 4/2014 |
| WO | 2015/085898 A1 | 6/2015 |
| WO | 2015/138844 A1 | 9/2015 |
| WO | 2015/196091 A1 | 12/2015 |
| WO | 2016/014497 A1 | 1/2016 |
| WO | 2016/089309 A1 | 6/2016 |
| WO | 2017/106716 A1 | 6/2017 |
| WO | 2018/098376 A1 | 5/2018 |
| WO | 2019/023392 A1 | 1/2019 |
| WO | 2019/226969 A1 | 11/2019 |
| WO | 2020/051307 A1 | 3/2020 |
| WO | 2020/160323 A2 | 8/2020 |
| WO | 2021/050953 A1 | 3/2021 |
| WO | 2021/158959 A2 | 8/2021 |
| WO | 2021/168271 A1 | 8/2021 |
| WO | 2021/212019 A1 | 10/2021 |
| WO | 2022/256840 A2 | 12/2022 |
| WO | 2024/177927 A1 | 8/2024 |

OTHER PUBLICATIONS

Aniket et al., "MicroglassificationIM: A novel technique for protein dehydration," J Pharm Sci. 103(3): 810-820 (2014).

Banerjee et al., "Electrospray ionization mass spectrometry: a technique to access the information beyond the molecular weight of the analyte," Int J Anal Chem. Article 282574 (2012) (40 pages).

Bock et al., "Electrospraying of polymers with therapeutic molecules: state of the art," Prag Polym Sci. 37(11): 1510-1551 (2012)(67 pages).

Bogelein et al., "Cyclone selection influences protein damage during drying in a mini spray-dryer," Int J Pharm. 401(1-2): 68-71 (2010).

Capelle, M.A.H. et al., "High throughout screening of protein formulation stability: Practical considerations," European Journal of Pharmaceutics and Biopharmaceutics, vol. 65; 131-148 (2007).

Clackson, T. et al., "Making antibody fragments using phage display libraries," Nature vol. 352; 624-628 (1991).

Cloupeau et al., "Electrohydrodynamic spraying functioning modes: a critical review," J Aerosol Sci. 25(6): 1021-1036 (1994).

Cloupeau et al., "Electrostatic spraying ofliquids: Main functioning modes," J Electrostat. 25(2): 165-184 (1990).

CN Search report Mailed on Jul. 28, 2022 for CN Application No. 202080012222.

Dias et al., "Tolerability of High-Volume Subcutaneous Injections ofa Viscous Placebo Buffer: A Randomized, Crossover Study in Healthy Subjects," AAPS PharmSciTech. 16(5): 1101-1107 (2015).

(56) References Cited

OTHER PUBLICATIONS

Elektrofi, Inc., Redefining the Delivery of Biologics, 11 pages, retrieved from Internet URL: https://www.elektrofi.com/welcome#technology on Nov. 15, 2021.
English Translation of CN Office Action Mailed on Aug. 3, 2022 for CN Application No. 202080012222.
English translation of CN Search Report mailed Jul. 28, 2022 for CN Application No. 2020800122229.
European Search Report and Search Opinion Received for EP Application No. 18838118, mailed on May 6, 2021, 12 pages.
Fernandez de la Mora et al., "The current emitted by highly conducting taylor cones," J Fluid Mech. 260: 155-184 (1994).
Fernandez de la Mora et al., "The fluid dynamics of Taylor cones," Annu Rev Fluid Mech. 39: 217-43 (2007) (29 pages).
Forgacs, E. et al., "Direct (Normal)-Phase High-Performance Liquid Chromatography," Chapter II.B. in Molecular Basis of Chromatographic Separation, CRC Press, Baco Raton, FL; 120-131 (1997).
Galam et al., "High-throughput assay for the identification of Hsp90 inhibitors based on Hsp90dependent refolding of firefly luciferase," available in PMC Mar. 1, 2008, published in final edited form as: Bioorg Med Chem. 15(5): 1939-1946 (2007) (16 pages).
Ganan-Calvo et al., "Current and droplet size in the electrospraying ofliquids. Scaling laws," J Aerosol Sci. 28(2): 249-275 (1997).
Gapinski et al., "Structure and dimensions of core-shell nanoparticles comparable to the confocal vol. studied by means of fluorescence correlation spectroscopy," Langmuir. 32(10): 2482-2491 (2016).
Gikanga et al., "Manufacturing of High-Concentration Monoclonal Antibody Formulations via Spray Drying-the Road to Manufacturing Scale," PDA J Pharm Sci Technol. 69(1): 59-73 (2015) (16 pages).
Giugliano et al., "Efficacy, safety, and tolerability of a monoclonal antibody to proprotein convertase subtilisin/kexin type 9 in combination with a statin in patients with hypercholesterolaemia (LAPLACE-TIMI 57): a randomised, placebo-controlled, dose-ranging, phase 2 study," available in PMC Mar. 3, 2015, published in rmal edited form as: Lancet. 380(9858): 2007-17 (2012) (20pages).
Hickey, J.W. et al., "Biologically Inspired Design ofNanoparticle Artificial Antigen-Presenting Cells for Immunomodulation," Nano Letters, vol. 17; 7045-7054 (2017).
Hui et al., "Progress in preparation of peptide protein drug microspheres," The medicine herald, Issue 10, 2007, pp. 1-32.
International Preliminary Report on Patentability received for PCT Patent Application No. PCT/US18/43774, mailed on Feb. 6, 2020, 10 pages.
International Search Report and Written Opinion received for PCT Patent Application No. PCT/US18/43774, mailed or Oct. 3, 2018, 12 pages.
Janssen Biotech Inc., "Highlights of prescribing information," <http://www.janssenlabels.com/package-insert/product-monograph/prescribinginformation/DARZALEX-pi.pdl>, dated Jul. 2019, retrieved on Aug. 22, 2019 (13 pages).
Jones, A.J.S., "Analysis of Polypeptides and Proteins," Advanced Drug Delivery Reviews, vol. 10; 29-90 (1993).
Kaltashov et al., "Electrospray ionization mass spectrometry can provide estimates of protein surface areas in solution, " available in PMC Jan. 27, 2009, published in final edited form as: Anal Chem. 77(16): 5370-5379 (2005) (21 pages).
Kim et al., "Controlled production of emulsion drops using an electric field in a flow-focusing microfluidic device," Appl Phys Lett. 91: 133106 (2007) (3 Pages).
Ku et al., "Electrospray characteristics of highly viscous liquids," J Aerosol Sci. 33(10): 1361-1378 (2002).
Lal et al., "Clean western blot signals from immunoprecipitated samples," available in PMC Jan. 25, 2006, published in final edited form as: Mol Cell Probes. 19(6): 385-388 (2005) (5 pages).
Lavorini et al., "New inhaler devices—the good, the bad and the ugly," Respiration. 88(1): 3-15 (2014).
Lee et al., "Solid-state stabilization of a-Chymotrypsin and catalase with carbohydrates," Ind Eng Chem Res. 45(14): 5134-5147 (2006).
Li et al., "Effects of pulsed electric fields and heat treatment on stability and secondary structure of bovine immunoglobulin G," J Agric Food Chem. 53(3): 663-670 (2005).
Longman et al., "Identifying differences in solution Conformations ofhvo chimeric IgG3 antibodies through triple detection SEC," LCGC North America. 18(21): (2006) (5 pages).
Lopez-Herrera et al., "Coaxial jets generated from eleclified Taylor cones. Scaling laws," J Aerosol Sci. 34(5): 535-552 (2003).
Lopez-Herrera et al., "Coaxial jets generated from electrified Taylor cones. Scaling laws," J Aerosol Sci. 34(5): 535-552 (2003).
Loscertales et al., "Micro/nano encapsulation via electrified coaxial liquid jets," Science. 295(5560): 1695-8 (2002).
Makadia et al., "Poly lactic-co-glycolic acid (PLGA) as biodegradable controlled drug delivery carrier," Polymers (Basel). 3(3): 1377-1397 (2011).
Marks, J.D. et al., "By-passing Immunization Human Antibodies from V-gene Libraries Displayed on Phage," J. Mol. Biol., vol. 222; 581-597 (1991).
Miller et al., "Antibody nanoparticle dispersions formed with mixtures of crowding molecules retain activity and in vivo bioavailability," available in PMC Oct. 1, 2013, published in final edited form as: J Pharm Sci. 101(10): 3763-3778 (2012) (25 pages).
Miller et al., "Low viscosity highly concentrated injectable nonaqueous suspensions of lysozyme microparticles," available in PMC Feb. 17, 2011, published in final edited form as: Langmuir. 26(2): 1067-1074 (2010) (22 pages).
Moghadam et al., "Electro-spray of high viscous liquids for producing mono-sized spherical alginate beads," Particuology. 6(4): 271-275 (2008).
Morales-Cruz et al., "Two-step nanoprecipitation for the production of protein-loaded PLGA nanospheres," Results Pharma Sci. 2: 79-85 (2012).
Mueller et al., "The rheology of suspensions of solid particles," Proc R Soc A. 466: 1201-1228 (2010).
Naqvi et al., "Living cell factories—electrosprayed microcapsules and microcarriers for minimally invasive delivery," Adv Mater. 28(27): 5662-71 (2016)(10 pages).
Nguyen et al., "Pharmaceutical applications of electrospraying," J Pharm Sci. 105(9): 2601-2620 (2016).
Park et al., "One step immobilization of protein encapsulated core/shell particles onto nanofibers," Macromol Mater Eng. 295(6): 544-550 (2010).
Patel et al. "Poloxamers: A pharmaceutical excipients with therapeutic behaviors", 2009, 15, International Journal of PharmTech Research, vol. (1), No. 2, pp. 299-303.
Persic, L. et al., "An integrated vector system for the eukaryotic expression of antibodies or their fragments after selection from phage display libraries," Gene; 9-18 (1997).
Pivnik, A.V., "Use of rituximab for treatment of HIV-infected patients with hematological disorders," Genotekhnologiya Medical Center, Moscow, 7 pages; English Abstract Only (2013).
Press, O.W. et al., "Monoclonal Antibody 1F5 (Anti-CD20) Serotherapy of Human B Cell Lymphoma," Blood, vol. 69; No. 2; 584-591 (1987).
Reichardt, C., "Solvatochromic Dyes as Solvent Polarity Indicators," Chem. Rev., vol. 94; 2319-2358 (1994).
Richardson, H. et al., "Influence of the glass transition on solvent loss from spin-cast glassy polymer thin films," Eur. Phys. J. E, vol. 12; 021; S87-S91 (2003).
Saglam et al., "Preparation of high protein micro-particles using two-step emulsification," Food Hydrocolloids. 25(5): 1139-48 (2011).
Sblattero, D. and Bradbury, A., "Exploiting recombination in single bacteria to make large phage antibody libraries," Nature Biotechnology, vol. 18; 75-80 (2000).
Serra-Peinado, C., et al., "Expression of CD20 after viral reactivation renders HIV-reservoir cells susceptible to Rituximab," Nature Communications, vol. 10; 15 pages (2019).
Shire et al., "Challenges in the development of high protein concentration formulations," J Pharm Sci. 93(6): 1390-402 (2004).
Takats et al., "Electrosonic spray ionization. A gentle technique for generating folded proteins and protein complexes in the gas phase and for studying ion-molecule reactions at atmospheric pressure," Anal Chem. 76(14): 4050-58 (2004).

(56) References Cited

OTHER PUBLICATIONS

Torchilin. "Multifunctional nanocarriers," Adv Drua Deliv Rev. 58(14): 1532-55 (2006).
Vehring, "Pharmaceutical particle engineering via spray drying," Pharm Res. 25(5): 999-1022 (2008).
Vonhoff, Sebastian, Thesis: "The Influence of Atomization Conditions on Protein Secondary and Tertiary Structure During Microparticle Formation by Spray-Freezing-Drying," Doktorgrades Dr. rer. nat, Der Natunvissenschaftlichen Fakultat, der Friedrich-Alexander Universitat Erlangen-Ntimberg, 2010, Chapters 6.4.3-6.6 and 8; 45 pages.
Wang et al., "FDA's regulatory science program for generic PLAI PLGA-based drug products," Am Phann Rev. <https://www.americanpharmaceuticalrevie,v.com/Featured-Articles/ 188841-FDA-s-Regulatory-Science-Program-for-Generic-PLA-PLGA-Based-Drug-Products/>, dated Jun. 15, 2016, retrieved on Jun. 27, 2022 (11 pages).
Wanning et al., "Pharmaceutical spray freeze drying," Int J Pharm. 488(1-2): 136-53 (2015).
Xie et al., "Encapsulation of protein drugs in biodegradable microparticles by co-axial electrospray," J Colloid Interface Sci. 317(2): 469-76 (2008).
Yuan et al., "Coaxial electrospray of curcumin-loaded microparticles for sustained drug release," PLoS One. 10(7):e0132609 (2015) (15 pages).
Yuan et al., "One-step fabrication of triple-layered rnicrocapsules by a tri-axial flow focusing device for microencapsulation of soluble drugs and imaging agents," Proc SPIE vol. 9711, Imaging, Manipulation, and Analysis of Biomolecules, Cells, and Tissues IX (2016) (12 pages).
Zhang et al., "Coaxial electrospray ofrnicroparticles and nanoparticles for biomedical applications," Expert Rev Med Devices. 9(6): 595-612 (2012).
Zhiqi, L., et al., "Functional Emulsifiers and Emulsions", China Light Industry Press, Apr. 30, 2000, 2 pages.

Ziabicki et al., "Crystal nucleation in an electric field," Macromol Symp. 104(1): 65-87 (1996).
CN Search report Mailed on Jan. 13, 2024 for CN Application No. 2021800293477.
English Translation of CN Office Action Mailed on Jan. 13, 2024 for CN Application No. 2021800293477.
English translation of CN Search Report mailed Jan. 13, 2024 for CN Application No. 2021800293477.
English translation of Office Action issued in Chinese Patent Application No. 201780072350.0, issued May 17, 2021 (16 pages).
Fenn et al., "Electrospray ionization for mass spectrometry of large biomolecules," Science. 246(4926): 64-71 (Oct. 6, 1989).
Mardles. E. W. J., "Viscosity of Suspensions and the Einstein Equation," Nature. 145: 970 (Jun. 22, 1940).
Nema et al., Pharmaceutical Dosage Forms: Parenteral Medications, Third Edition, vol. 3: Requlations, Validation and the Future. Informa Healthcare, vii-304 (2010) (328 pages).
Supplementary Partial European Search Report for European Patent Application No. 17873547.8, dated Jun. 15, 2020 (9 pages).
U.S. Department of Health and Human Services, "Q3C—Tables and List: Guidance for Industry," Aug. 2018 (10 pages).
Zhang et al., "Coaxial electrospray of ranibizumab-loaded microparticles for sustained release of anti-VEGF therapies," PloS One. 10(8): e0135608 (2015) (16 pages).
Frost, G.I., "Recombinant human hyaluronidase (rHuPH20): an enabling platform for subcutaneous drug and fluid administration," Expert Opinion Drug Deliv., vol. 4; No. 4; 427-440 (2007).
Jun, L., "Guizho Science and Technology Press", Agricultural building materials, Aug. 31, 1999, 4 pages (Concise explanation met by the English Translation of CN Appl 202080064558 office action provided herewith).
Kaltashov et al., "Estimates of Protein Surface Areas in Solution by Electrospray Ionization Mass Spectrometry," available in PMC Jan. 27, 2009, published in final edited form as: Anal Chem. 77(16): 5370-5379 (2005) (21 pages).

* cited by examiner 100 um 200 um 100 um 300 um 30 um 20 um 20 um 30 um 10 um 100 um 30 um 100 um 50 um 300 um 100 um 200 um 100 um 200 um 30 um 50 um 30 um 10 um 30 um 10 um 300 um 30 um 200 um 300 um 30 um 200 um 300 um 200 um 300 um 300 um 20 um 200 um 300 um 100 um 10 um 30 um 30 um 20 um 30 um 10 um 100 μm 20 μm 30 um 10 um 100 um 10 um 100 um 10 um 30 um 100 um 100 um 100 um

FORMATION OF PARTICLES INCLUDING AGENTS

RELATED APPLICATIONS

This application is a Divisional of U.S. application Ser. No. 16/633,097, filed Jul. 25, 2018, which is the U.S. National Stage of International Application No. PCT/US2018/043774, filed Jul. 25, 2018, which designates the U.S., published in English, and claims the benefit of U.S. Provisional Application No. 62/676,195, filed May 24, 2018, and U.S. Provisional Application No. 62/536,746, filed Jul. 25, 2017. The entire teachings of the above applications are incorporated herein by reference.

BACKGROUND OF THE INVENTION

Current limitations with respect to the delivery of agents, e.g., therapeutic or diagnostic agents, include their solubility thresholds, stability, and unfavorable rheological properties. These are particularly acute in the case of high concentration solutions of agents, e.g., >100 mg/mL, such as those which are sometimes needed to administer high doses of therapeutic or diagnostic agents. Particulate matter synthesized from the agents is one option for addressing these limitations. Therefore, a need exists for robust and controllable methods of particle preparation.

SUMMARY OF THE INVENTION

In one aspect, the invention provides a method of forming particles by providing droplets including a first liquid and an agent, contacting the droplets with a second liquid, and allowing the droplets to dry to form the particles.

In some embodiments, the agent is a therapeutic or diagnostic agent. In other embodiments, the agent is another agent, such as a metal or other element, silica, titania, a metal salt, a metal oxide, a metal nitride, a metal sulfide, a metal alkoxide, a polymer, or any combination thereof.

In another aspect, the invention provides a method of forming particles by providing droplets including a first liquid and a therapeutic or diagnostic agent, contacting the droplets with a second liquid, and allowing the droplets to dry to form the particles.

In some embodiments, the second liquid has a density between that of the droplets and the particles. The droplets float on the second liquid, but the particles formed do not float on the second liquid. The first liquid evaporates to dry the droplets.

In certain embodiments, the second liquid has a density greater than that of the droplets. The droplets and particles formed float on the second liquid. The first liquid evaporates to dry the droplets.

In some embodiments, the second liquid has a density lower than that of the droplets, and the droplets do not float on the second liquid. The first liquid disperses into the second liquid to dry the droplets.

In some embodiments, the particles have diameters from 0.1 to 1000 µm, e.g., 1 to 400 µm, 1 to 200 µm, 1 to 100 µm, 1 to 50 µm, 1 to 25 µm, 1 to 10 µm, 10 to 100 µm, 50 to 100 µm, 50 to 75 µm, or 75 to 100 µm.

In some embodiments, the concentration of the therapeutic or diagnostic agent in the first liquid is from 0.0001 to 1000 mg/mL, e.g., 100 to 800, 200 to 700, 200 to 600, or 300 to 700 mg/mL. In other embodiments, the particles have a mass loading of the therapeutic or diagnostic agent from 1% to 100%.

In some embodiments, the particles have less than 10% by weight of the first liquid or the second remaining after drying.

In other embodiments, the first liquid is aqueous or an organic solvent. Exemplary aqueous liquids are water, 0.9% saline, lactated Ringer's solution, dextrose 5%, a buffer, and any combination thereof. The buffer may include acetate buffer, histidine buffer, succinate buffer, HEPES buffer, tris buffer, carbonate buffer, citrate buffer, phosphate buffer, glycine buffer, barbital buffer, and cacodylate buffer. Exemplary organic solvents are acetic acid, acetone, acetonitrile, alkanes (e.g., hexanes, heptane), amyl acetate, butanol, butyl acetate, chlorobenzene, chloroform, cumene, cyclohexane, 1,2-dichloroethene, dichloromethane, diethyl ether, dimethoxyethane, dimethylacetamide, dimethylformamide, dimethyl sulfoxide, 1,4-dioxane, ethanol, 2-ethoxyethanol, ethyl acetate, ethyl nitrate, ethyleneglycol, formic acid, hydrazine, isopropanol, methanol, methyl acetate, 2-methyl-1-butanol, 2-methyl-1-propanol, methylbutyl ketone, methylcyclohexane, methylethyl ketone, methylpyrrolidone, methyl tert-butyl ether, nitromethane, propanol, propyl acetate, sulfolane, sarcosine, tetrahydrofuran, tetralin, toluene, 1,1,2-tricholoroethane, triethylamine, urea, xylene, and any combination thereof.

The first liquid may further include another component, such as a carbohydrate, a pH adjusting agent, a salt, a chelator, a mineral, a polymer, a surfactant, a protein stabilizer, an emulsifier, an antiseptic, an amino acid, an antioxidant, a protein, an organic solvent, a paraben, a bactericide, a fungicide, a vitamin, a preservative, or nutrient media. In some embodiments, each of the other components is, independently, 0.0001 to 99% (w/v) of the first liquid, e.g., 0.0001 to 90% (w/v), 0.0001 to 50% (w/v), 0.0001 to 10% (w/v), 0.0001 to 1% (w/v), or 0.0001 to 0.1% (w/v). Exemplary carbohydrates include dextran, trehalose, sucrose, agarose, mannitol, lactose, sorbitol, or maltose. The pH adjusting agent may be acetate, citrate, glutamate, glycinate, histidine, lactate, maleate, phosphate, succinate, tartrate, bicarbonate, aluminum hydroxide, phosphoric acid, hydrochloric acid, DL-lactic/glycolic acids, phosphoryletha-nolamine, tromethamine, imidazole, glyclyglycine, or monosodium glutamate. Exemplary salts include sodium chloride, calcium chloride, potassium chloride, sodium hydroxide, stannous chloride, magnesium sulfate, sodium glucoheptonate, sodium pertechnetate, or guanidine hydrochloride. The chelator can be disodium edetate or ethylenediaminetetraacetic acid. The mineral can be calcium, zinc, or titanium dioxide. Examples of polymers include propyleneglycol, glucose star polymer, silicone polymer, polydimethylsiloxane, polyethylene glycol, carboxymethylcellulose, poly(glycolic acid), poly(lactic-co-glycolic acid), or polylactic acid. The surfactant may be polysorbate, magnesium stearate, sodium dodecyl sulfate, TRITON™ N-101, glycerin, or polyoxyethylated castor oil. Exemplary protein stabilizers include acetyltryptophanate, caprylate, or N-acetyltryptophan. In other embodiments, the protein stabilizer is trehalose, PEG 200, PEG 300, PEG 3350, PEG 8000, PEG 10000, PEG 20000, polyoxamers, polyvinylpyrrolidone, polyacrylic acids, poly(vinyl) polymers, polyesters, polyaldehydes, tert-polymers, polyamino acids, hydroxyethyl starch, N-methyl-2-pyrrolidone, sorbitol, sucrose, or mannitol. The emulsifier can be polysorbate 80, polysorbate 20, sorbitan monooleate, ethanolamine, polyoxyl 35 castor oil, poloxyl 40 hydrogenated castor oil, carbomer 1342, a corn oil-mono-di-triglyceride, a polyoxyethylated oleic glyceride, or a poloxamer. Exemplary antiseptics include phenol, m-cresol, benzyl alcohol, 2-phenyloxyethanol, chlorobutanol, neomycin, benzethonium chloride, gluteraldehyde, or beta-propiolactone. The amino acid may be alanine, aspartic acid, cysteine, isoleucine, glutamic acid, leucine, methionine, phenylalanine, pyrrolysine, serine, selenocysteine, threonine, tryptophan, tyrosine, valine, asparagine, L-arginine, histidine, glycine, glutamine, or a combination thereof. The antioxidant can be gluta-thione, ascorbic acid, cysteine, or tocopherol. The protein can be protamine, protamine sulfate, or gelatin. The organic solvent can be dimethyl sulfoxide or N-methyl-2-pyrrolidone. The preservative can be methyl hydroxybenzoate, thimerosal, parabens, formaldehyde, or castor oil. The paraben can be a parahydroxybenzoate. The bactericide can be benzalkonium chloride. In certain embodiments, the liquid may further include an analgesic, such as acetaminophen or lidocaine. The first liquid may further include adenine, tri-n-butyl phosphate, octa-fluoropropane, white petrolatum, or p-aminophenyl-p-anisate.

In certain embodiments, the amount of additional compound, i.e., excipient, present in the first liquid, second, liquid, or medium, is as shown in the following table.

| Excipient | Range 1 | Range 2 | Range 3 | Range 4 |
| --- | --- | --- | --- | --- |
| Carbohydrate | 10-30% | 3-50% | 1-80% | 0.3-99% |
| pH adjusting agent | 0.5-5% | 0.2-40% | 0.05-70% | 0.01-99% |
| Salt | 10-50% | 3-70% | 1-85% | 0.3-99% |
| Chelator | 0.01-1% | 0.003-40% | 0.001-80% | 0.0003-99% |
| Mineral | 10-50% | 3-70% | 1-80% | 0.3-99% |
| Polymer | 10-60% | 3-75% | 1-85% | 0.3-99% |
| Surfactant | .01-1% | 0.003-40% | 0.001-80% | 0.0003-99% |
| Protein stabilizer | 10-70% | 3-70% | 1-85% | 0.3-99% |
| Emulsifier | .01-1% | 0.003-40% | 0.001-80% | 0.0003-99% |
| Antiseptic | .5-10% | 0.2-50% | 0.05-70% | 0.02-99% |
| Amino acids | 10-25% | 3-50% | 1-85% | 0.3-99% |
| Antioxidant | 0.01-1% | 0.003-40% | 0.001-80% | 0.0003-99% |
| Protein | 1-10% | 0.3-50% | 0.1-75% | 0.03-99% |
| Organic solvent | 0.001-2% | 0.0003-1% | 0.0001-10% | 0.00003-99% |
| Nutrient media | 10-50% | 3-70% | 1-85% | 0.3-99% |
| Paraben | 0.01-5% | 0.005-10% | 0.001-50% | 0.001-99% |
| Bactericide | 0.01-5% | 0.005-10% | 0.001-50% | 0.001-99% |
| Fungicide | 0.01-5% | 0.005-10% | 0.001-50% | 0.001-99% |
| Vitamin | 1-50% | 1-70% | 0.1-85% | 0.01-99% |
| Analgesic | 0.01-5% | 0.005-10% | 0.001-50% | 0.001-99% |

In some embodiments, the second liquid is an oil, an organic solvent, aqueous, an ionic liquid, or a combination thereof. Exemplary oils are coconut oil, cottonseed oil, fish oil, grape seed oil, hazelnut oil, hydrogenated vegetable oils, lime oil, olive oil, palm seed oil, peanut oil, peppermint oil, safflower oil, sesame oil, soybean oil, sunflower oil, walnut oil, and any combination thereof.

Exemplary organic solvents are benzyl benzoate, acetone, ethyl lactate, dimethyl isosorbide, dimethyl sulfoxide, glycofurol, diglyme, methyl tert-butyl ether, polyethylene glycol, 2-pyrrolidone, tetrahydrofurfuryl alcohol, trigylcerides, methyl acetate, ethyl acetate, propyl acetate, butyl acetate, amyl acetate, chloroform, dichloromethane, ethanol, methanol, propanol, butanol, acetonitrile, diethyl ether, diglyme, 1,2-dimethoxyethane, dimethylformamide, pentane, toluene, and any combination thereof.

In some embodiments, the organic solvent is ethyl lactate, tocopherol, octa-fluoropropane, (perfluorohexyl)octane, n-acetyltryptophan, trigylcerides, triglycerides of the fractionated plant fatty acids C8 and C10, propylene glycol diesters of saturated plant fatty acids C8 and C10, ethyl laurate, methyl caprylate, methyl caprate, methyl myristate, methyl oleate, methyl linoleate, dimethyl adipate, dibutyl suberate, diethyl sebacate, ethyl macadamiate, trimethylolpropane triisosterate, isopropyl laurate, isopropyl myristate, diethyl succinate, polysorbate esters, ethanol amine, propanoic acid, octanoic acid, triacetin, citral, anisole anethol, benzaldehyde, linalool, caprolactone, phenol, thioglycerol, dimethylacetamide, ethyl formate, ethyl hexyl acetate, eugenol, clove bud oil, diethyl glycol monoether, benzyl alcohol, dimethyl isosorbide, ethyl ether, isopropyl acetate, methyl isobutyl ketone, methyl tert-butyl ether, N-methyl pyrrolidone, perfluorodecalin, 2-pyrrolidone, ethyl oleate, ethyl caprate, dibutyl adipate, fatty acid esters, hexanoic acid, octanoic acid, triacetin, diethyl glycol monoether, gamma-butyrolactone, eugenol, clove bud oil, citral, limonene, polyoxyl 40 hydrogenated castor oil, polyoxyl 35 castor oil, octanol, hexanol, decanol, gamma-butyrolactone, tocopherol, octa-fluoropropane, (perfluorohexyl)octane, n-acetyltryptophan, ethyl laurate, methyl caprylate, methyl caprate, methyl myristate, methyl oleate, methyl linoleate, dimethyl adipate, dibutyl suberate, diethyl sebacate, ethyl macadamiate, trimethylolpropane triisosterate, isopropyl laurate, isopropyl myristate, diethyl succinate, polysorbate esters, ethanol amine, propanoic acid, citral, anisole, anethol, benzaldehyde, linalool, caprolactone, phenol, thioglycerol, dimethylacetamide, TRANSCUTOL® HP (diethylene glycol monoethyl ether), solketal, isosorbide dimethyl ether, ethyl formate, ethyl hexyl acetate, and any combination thereof.

In particular embodiments, the organic solvent is an alkyl acetate, an aryl acetate, an aryl alkyl acetate, or a combination thereof.

Exemplary aqueous liquids are concentrated solutions comprising salts, buffers, carbohydrates, proteins, biologics, polymers, or surfactants. Exemplary salts include sodium chloride, sodium citrate, calcium chloride, sodium iodide, and potassium iodide. Exemplary buffers include, phosphate buffer solution, sodium citrate, borate buffered saline, N-cyclohexyl-2-aminoethanesulfonic acid (CHES) buffer, tris (hydroxymethyl)aminoethane (Tris), (4-(2-hydroxyethyl)-1-piperazineethanesulfonic acid) (HEPES), or (3-(N-morpholino)propanesulfonic acid) (MOPS). Exemplary carbohydrates include dextran, trehalose, sucrose, agarose, mannitol, lactose, sorbitol, or maltose. Exemplary proteins include serum albumin (e.g., bovine serum albumin), monoclonal antibodies, cytokines (e.g., TNFalpha, IFN-gamma, TGF-beta, IL-10 etc.), or globulins (e.g., protein C). Exemplary biologics include DNA, or RNA. Exemplary polymers include, propyleneglycol, glucose star polymer, polydimethylsiloxane, polyethylene glycol, carboxymethylcellulose, poly(glycolic acid), poly(lactic-co-glycolic acid), or polylactic acid, PEG 200, PEG 300, PEG 3350, PEG 8000, PEG 10000, PEG 20000, polyvinylpyrrolidone, or polyamino acids. Exemplary surfactants include, polysorbate, magnesium stearate, sodium dodecyl sulfate, TRITON™ N-101, glycerin, docusate, sodium stearate, decyl glucoside, nonoxynol-9, or cetyltrimethylammonium bromide.

Exemplary ionic liquids contain pyridinium, pyridazinium, pyrimidinium, pyrazinium, imidazolium, pyrazolium, thiazolium, oxazolium, triazolium, ammonium, sulfonium, halides, sulfates, sulfonates, carbonates, phosphates, bicarbonates, nitrates, acetates, $PF_6^-$, $BF_4^-$, triflate, nonaflate, bis(triflyl)amide, trifluoroacetate, heptafluorobutanoate, haloaluminate, or any combination thereof. In some embodiments, the second liquid is a mixture of, e.g., two or more liquids of different polarities. In some embodiments, the solubility of the first liquid in one component of the mixture differs from the solubility of the first liquid in another component or components of the mixture. In some embodiments, where the first liquid disperses into the second, the morphology of the particles produced can be controlled by adjusting the ratio of the liquids in the mixture. For example, a mixture including a higher vol % of the lower solubility can give rounder particles. One liquid in the mixture can be from 1 to 99 vol %, e.g., 1-10 vol %, 5-25 vol %, 10-30 vol %, 15-50 vol %, 20-60 vol %, 30-75 vol %, 40-80 vol %, 50-99 vol %, or 75-99 vol %, with the balance being the other liquid or liquids. Exemplary mixtures are benzyl benzoate/acetone (e.g., 5-30% benzyl benzoate, such as 5:95, 10:90, 15:85, 20:80, 25:75, or 30:70), isopropyl alcohol/sesame oil (e.g., 35-65% isopropyl alcohol, such as about 35:65, 40:60, 45:55, 50:50, 55:45, 60:40, or 65:35), hexanes/ethanol (e.g., 10-35% hexanes, such as about 10:90, 15:85, 20:80, 25:75, 30:70, or 35:65), toluene/acetonitrile (e.g., 10-35% toluene, such as about 10:90, 15:85, 20:80, 25:75, 30:70, or 35:65), cottonseed oil/butyl acetate (e.g., 10-35% cottonseed oil, such as about 10:90, 15:85, 20:80, 25:75, 30:70, or 35:65), toluene/ethyl acetate (e.g., 10-35% toluene, such as about 10:90, 15:85, 20:80, 25:75, 30:70, or 35:65), diethyl ether/isopropanol (e.g., 5-30% diethyl ether, such as about 5:95, 10:90, 15:85, 20:80, 25:75, or 30:70), tetrahydrofuran/pentane (e.g., 35-65% THF, such as about 35:65, 40:60, 45:55, 50:50, 55:45, 60:40, or 65:35), safflower oil/methanol (e.g., 25-55% safflower oil, such as about 25:75, 30:70, 35:65, 40:60, 45:55, 50:50, or 55:45), and lime oil/acetone (5-30% lime oil, such as about 5:95, 10:90, 15:85, 20:80, 25:75, or 30:70).

In some embodiments, the first liquid or the second liquid has a viscosity from 0.01 cP to 10,000 cP, e.g., from 0.01 to 1,000 cP, from 0.01 to 100 cP, from 0.01 to 50 cP, from 0.01 to 25 cP, from 0.01 to 10 cP, from 0.01 to 5 cP, from 0.01 to 1 cP.

The method may further include removing the particles from the second liquid through centrifugation, sieving, filtration, magnetic collection, solvent exchange, or decanting.

The method may further include washing the particles with a third liquid. In certain embodiments, the third liquid is an organic solvent. Exemplary organic solvents are acetic acid, acetone, acetonitrile, alkanes (e.g., hexanes, heptane), amyl acetate, butanol, butyl acetate, chlorobenzene, chloroform, cumene, cyclohexane, 1,2-dichloroethene, dichloromethane, diethyl ether, dimethoxyethane, dimethylacetamide, dimethylformamide, dimethyl sulfoxide, 1,4-dioxane, ethanol, 2-ethoxyethanol, ethyl acetate, ethyl nitrate, ethyleneglycol, formic acid, hydrazine, isopropanol, methanol, methyl acetate, 2-methyl-1-butanol, 2-methyl-1-propanol, methylbutyl ketone, methylcyclohexane, methylethyl ketone, methylpyrrolidone, methyl tert-butyl ether, nitromethane, propanol, propyl acetate, sulfolane, sarcosine, tetrahydrofuran, tetralin, toluene, 1,1,2-tricholoroethane, triethylamine, urea, xylene, and any combination thereof.

The third liquid may be removed through evaporation or lyophilization.

In certain embodiments, the second liquid may include a surfactant, carbohydrate, a pH adjusting agent, a salt, a chelator, a mineral, a polymer, a protein stabilizer, an emulsifier, an antiseptic, an amino acid, an antioxidant, a protein, an organic solvent, a paraben, a bactericide, a fungicide, a vitamin, preservative, or nutrient media. In some embodiments, each of the other components is present, independently, at 0.0001 to 99% (w/v) of the liquid, e.g., at 0.0001 to 90% (w/v), at 0.0001 to 50% (w/v), at 0.0001 to 10% (w/v), at 0.0001 to 1% (w/v), or at 0.0001 to 0.1% (w/v). Exemplary carbohydrates include dextran, trehalose, sucrose, agarose, mannitol, lactose, sorbitol, or maltose. The pH adjusting agent may be acetate, citrate, glutamate, glycinate, histidine, lactate, maleate, phosphate, succinate, tartrate, bicarbonate, aluminum hydroxide, phosphoric acid, hydrochloric acid, DL-lactic/glycolic acids, phosphorylethanolamine, tromethamine, imidazole, glyclyglycine, or monosodium glutamate. Exemplary salts include sodium chloride, calcium chloride, potassium chloride, sodium hydroxide, stannous chloride, magnesium sulfate, sodium glucoheptonate, sodium pertechnetate, or guanidine hydrochloride. The chelator can be disodium edetate or ethylenediaminetetraacetic acid. The mineral can be calcium, zinc, or titanium dioxide. Examples of polymers include propyleneglycol, glucose star polymer, silicone polymer, polydimethylsiloxane, polyethylene glycol, carboxymethylcellulose, poly(glycolic acid), poly(lactic-co-glycolic acid), or polylactic acid. Exemplary protein stabilizers include acetyltryptophanate, caprylate, or N-acetyltryptophan. In other embodiments, the protein stabilizer is trehalose, PEG 200, PEG 300, PEG 3350, PEG 8000, PEG 10000, PEG 20000, polyoxamers, polyvinylpyrrolidone, polyacrylic acids, poly (vinyl) polymers, polyesters, polyaldehydes, tert-polymers, polyamino acids, hydroxyethylstarch, N-methyl-2-pyrrolidone, sorbitol, sucrose, or mannitol. The emulsifier can be polysorbate 80, polysorbate 20, sorbitan monooleate, ethanolamine, polyoxyl 35 castor oil, poloxyl 40 hydrogenated castor oil, carbomer 1342, a corn oil-mono-di-triglyceride, a polyoxyethylated oleic glyceride, or a poloxamer. Exemplary antiseptics include phenol, m-cresol, benzyl alcohol, 2-phenyloxyethanol, chlorobutanol, neomycin, benzethonium chloride, gluteraldehyde, or beta-propiolactone. The amino acid may be alanine, aspartic acid, cysteine, isoleucine, glutamic acid, leucine, methionine, phenylalanine, pyrrolysine, serine, selenocysteine, threonine, tryptophan, tyrosine, valine, asparagine, L-arginine, histidine, glycine, glutamine, or a combination thereof. The antioxidant can be glutathione, ascorbic acid, cysteine, or tocopherol. The protein can be protamine, protamine sulfate, or gelatin. The organic solvent can be dimethyl sulfoxide or N-methyl-2-pyrrolidone. The preservative can be methyl hydroxybenzoate, thimerosal, parabens, formaldehyde, or castor oil. Exemplary surfactants are polysorbate, magnesium stearate, sodium dodecyl sulfate, glycerin, PEGylated phospholipids, TRITONs, sorbitan monopalmitate, polysorbate 80, 4-lauryl etherpolyoxyethylene polyoxypropylene copolymer, ethoxylated sorbitan esters, ethoxylated castor oil, fatty acids, bile salts, ethoxylated glycerides, ethoxylated fatty acids, sphingolipids, sorbitan ester, polyglycosides, cetyl alcohol, cocamide, glucosides, maltosides, monolaurin, polyglycol steroidal esters, fatty acid esters, poloxamers, phospholipids, fatty acid salts, sterol alcohols, sterol alcohol salts, cationic surfactants, anionic surfactants, amphoteric surfactants, zwitterionic detergents, or any combination thereof. The paraben can be a parahydroxybenzoate. The bactericide can be benzalkonium chloride. In certain embodiments, the liquid may further include an analgesic, such as acetaminophen or lidocaine.

In some embodiments, the therapeutic or diagnostic agent in the particles has 0.5 to 1.0 activity per unit, e.g., 0.75 to 1.0 or 0.9 to 1.0 activity per unit.

In some embodiments, the particles have less than 10% aggregation or less than 10% fragmentation of the diagnostic or therapeutic agent, e.g., less than 9, 8, 7, 6, 5, 4, 3, 2, 1, 0.5, 0.1%. In some embodiments, the particles have less than 50% change in charge variants of the diagnostic or therapeutic agent, e.g., less than 40, 30, 20, 10, 9, 8, 7, 6, 5, 4, 3, 2, 1, 0.5, 0.1%, compared to the agent prior to particle formation.

In some embodiments, the suspension of particles may include insoluble particulate matter larger than or equal to 1 μm in size. In some cases, the number of insoluble particles is from 0 to 100,000,000 per mL, e.g., less than 10,000,000, 1,000,000, 100,000, 10,000, 1000, 100, 10, or 1 per mL. For example, the number of insoluble particles greater than 10 μm is from 0 to 6,000 per mL, e.g., less than 5,000, 4,000, 3,000, 2,000, 1,000, 500, 100, 10, or 1 per mL, and/or the number of insoluble particles greater than 25 μm is from 0 to 600 per mL, e.g., less than 500, 400, 300, 200, 100, 50, 10, or 1 per mL.

Exemplary therapeutic or diagnostic agents are nucleic acids, oligonucleotides, antibodies or fragment thereof, amino acids, peptides, proteins, cells, bacteria, gene therapeutics, genome engineering therapeutics, epigenome engineering therapeutics, carbohydrates, chemical drugs, contrast agents, magnetic particles, polymer beads, metal nanoparticles, metal microparticles, quantum dots, antioxidants, antibiotic agents, hormones, nucleoproteins, polysaccharides, glycoproteins, lipoproteins, steroids, analgesics, local anesthetics, anti-inflammatory agents, anti-microbial agents, chemotherapeutic agents, exosomes, outer membrane vesicles, vaccines, viruses, bacteriophages, adjuvants, vitamins, minerals, organelles, and any combination thereof.

In some embodiments, the particles have a core-shell morphology, where the shell may include multiple layers. In certain embodiments, the core is solid, gel, or liquid. In some embodiments, the shell is a gel, in particular a hydrogel, ionogel, or organogel. Exemplary hydrogels, ionogels and organogels include collagen hydrogels, chitosan hydrogels, methylcellulose hydrogels, dextran hydrogels, alginate hydrogels, agarose hydrogels, poly(methyl methacrylate) hydrogels, poly(amido amine) hydrogels, poly(ethyleneimine) hydrogels, polyethylene oxide hydrogels, gelatin hydrogels, hyaluronic acid hydrogels, 4-tert-butyl-1-aryl cyclohexanol organogels, L-lysine derivative organogels, poly(ethylene glycol) organogels, polycarbonate organogels, polyester organogels, polyalkene organogels, oxalyl amide derivative organogels, and any combinations thereof.

In a related aspect, the invention provides a composition, e.g., a suspension or dried form, containing a plurality of particles that include an agent, e.g., a therapeutic or diagnostic agent. The composition preferably has a concentration of insoluble particles of between 0 and 100,000,000 per mL in suspension or upon reconstitution. In some embodiments, the concentration of insoluble particles is between 0 and 1,000,000 per mL in suspension or upon reconstitution. In some embodiments, the concentration of insoluble particles is between 0 and 10,000 per mL in suspension or upon reconstitution. In some embodiments, the concentration of insoluble particles with a characteristic size greater than or equal to 10 μm is between 0 to 6,000 per mL in suspension or upon reconstitution. In certain embodiments, the concentration of insoluble particles with a characteristic size greater than or equal to 25 μm is between 0 to 600 per mL in suspension or upon reconstitution. The therapeutic or diagnostic agent preferably has 0.5 to 1.0 activity per unit, e.g., 0.75 to 1.0 activity per unit, or 0.9 to 1.0 activity per unit (e.g., about 0.99 activity per unit).

In yet another related aspect, the invention provides a composition containing a plurality of particles that include an agent, e.g., a therapeutic or diagnostic agent, where the storage stability of the agent in the particles is improved with respect to the storage stability of a first liquid of the agent. In some embodiments, storage conditions are defined by time (e.g., more than 2 years, more than 1 year, more than 6 months, more than 3 months, more than 1 month, or more than 1 week) and temperature (e.g., −80° C. to 100° C., −80° C. to 60° C., −20° C. to 60° C., 4 to 60° C.), among potentially other variables. In some embodiments, the storage time is 3 days, 7 days, 30 days, 90 days, 180 days, 1 year, or 2 years. In some embodiments, this temperature is −80° C., −40° C., −20° C., 4° C., 25° C., 40° C., or 40-60° C. In some embodiments, after dissolution or reconstitution of the particles following storage, SvPs are present in quantities from about 0 to 100,000,000 per mL, e.g., from 0 to 10,000,000 per mL, from 0 to 1,000,000 per mL, from 0 to 500,000 per mL, from 0 to 100,000 per mL, from 0 to 50,000 per mL, from 0 to 10,000 per mL, from 0 to 6,000 per mL, from 0 to 1,000 per mL, from 0 to 600 per mL, from 0 to 250 per mL, from 0 to 100 per mL, from 0 to 60 per mL, or from 0 to 10 per mL. In some embodiments, the count of particles with characteristic size greater than or equal to 10 μm is from 0 to 6,000 per mL, e.g., from 0 to 1,000 per mL, from 0 to 100 per mL, from 0 to 10 per mL, from 0 to 5 per mL, from 0 to 3 per mL, or from 0 to 1 per mL. In some embodiments, the count of particles with characteristic size greater than or equal to 25 μm is from 0 to 600 per mL, e.g., from 0 to 100 per mL, from 0 to 10 per mL, from 0 to 3 per mL, from 0 to 1 per mL, from 0 to 0.5 per mL, or from 0 to 0.1 per mL. In some embodiments, after dissolution or reconstitution of the particles following storage, the therapeutic or diagnostic agent retains from 0.5 to 1.0 activity, e.g., from 0.75 to 1.0 activity, from 0.9 to 1.0 activity, from 0.95 to 1.0 activity, from 0.99 to 1.0 activity, or from 0.999 to 1.0 activity. In some embodiments, dissolution or reconstitution of the particles following storage provides less than a 10% increase in aggregates of the agent, e.g., a protein, (e.g., less than 8%, less than 5%, less than 4%, less than 3%, less than 1%, less than 0.5%, or less than 0.1%) as compared to the agent in the first liquid prior to processing. In some embodiments, the dissolution or reconstitution of the particles after storage provides less than a 10% increase in fragments of the agent, e.g., a protein, (e.g., less than 8%, less than 5%, less than 4%, less than 3%, less than 1%, less than 0.5%, or less than 0.1%) as compared to the therapeutic or diagnostic agent in the first liquid prior to processing. In some embodiments, the dissolution or reconstitution of the particles following storage provides less than a 50% change in charge variants in the population of the agent, e.g., an antibody or an antibody fragment, (e.g., less than 40, 30, 20, 10, 8, 5, 4, 3, or 1%) as compared to the therapeutic or diagnostic agent prior to particle formation.

In some embodiments, the particles described herein are discrete, roughly spheroidal, and of controlled dispersity with a characteristic size from sub-micrometers to tens of micrometers, in contrast to, e.g., a porous monolithic "cake", such as is typically produced during conventional lyophilization. This morphology typically allows for a flowable powder (as described by low Hausner ratios) without post-processing. Sphericity of the particles may range from 0.1 to 1, e.g., be at least 0.2, 0.4, 0.6, or 0.8.

The particles may or may not include residual first and/or second liquid as described herein.

In another related aspect, the invention provides a composition containing a plurality of particles, where the particles are formed by a method as described herein.

Definitions

The term "about" refers to +/−10% of a recited value.

The term "droplet" refers to a material that has a liquid outer surface.

The term "particle" refers to a quantity of an agent or agents which, in one aspect, is either in a state of matter that is substantially solid as compared to a liquid droplet or in a gel form. In some embodiments, the particle includes a core and a shell, where the shell is viewed as an encapsulant. In other embodiments, the particle does not include a shell, in which case the particle is made up entirely of a core.

The term "encapsulant" refers to a substance that can be dried or gelled around a particle core to form a shell.

The term "core-shell morphology" refers to a morphology having multiple layers that comprise different components and/or concentrations of components. A "dry" particle component, i.e., a dry core or a dry shell, including the agent or agents, has undergone a desiccation step or series of desiccation steps, such that its moisture or solvent content is substantially reduced in relation to that before any desiccation. In some embodiments, the residual moisture or solvent content of the dry component is less than about 10% by weight, e.g., less than about 5% by weight. Exemplary methods for the measurement of moisture content include chemical titration methods, e.g., Karl Fischer titration involving a vacuum oven. A variety of solvents, including water, may also be measured using weight loss methods involving thermal excitation. Exemplary methods include thermogravimetric analysis with Infrared spectroscopy (TGA-IR).

The term "transport number" refers to the ratio of the rate of a solute mass transport process in a droplet or particle to the rate of a solvent mass transport process outside of a droplet or particle.

The term "Rayleigh limit" refers to the specific charge, e.g., in units of Coulombs per kilogram, corresponding to the point at which Coulombic repulsion overcomes the binding forces of surface tension in a drop, leading to Coulomb fission or shedding of charge from the drop through some other mechanism.

The term "pharmaceutical composition" denotes a composition in which a therapeutic or diagnostic agent retains, or partially retains, its intended biological activity or functional form, and in which only pharmaceutically acceptable components are included.

A "pharmaceutically acceptable" component, e.g., an excipient, is a component which is suitable for administration to a subject, e.g., a human.

The term "powder formulation" refers to a solid formulation including solid particles in the absence of a carrier liquid. In some embodiments, the powder formulation is suitable for powder injection, e.g., with a Portal PRIME device.

The term "stabilizer" refers to an excipient or a mixture of excipients which stabilizes the physical and/or chemical properties of agents, e.g., therapeutic or diagnostic agents. In some embodiments, stabilizers prevent, e.g., degradation of the therapeutic or diagnostic agents during droplet formation, desiccation, and/or storage of the particulate matter. Exemplary stabilizers include, but are not limited to, sugars, salts, hydrophobic salts, detergents, reducing agents, cyclodextrins, polyols, carboxylic acids, and amino acids.

A "stable" formulation refers to a formulation in which the therapeutic or diagnostic agent retains an acceptable portion of its essential physical and/or chemical and/or biological properties over an acceptable period of time. In the case of proteins and peptides, e.g., exemplary methods of assessing stability are reviewed in (i) Peptide and Protein Drug Delivery, 247-301, Vincent Lee Ed., Marcel Dekker, Inc., New York, NY, 1991, and (ii) Jones, A., Adv. Drug Delivery Rev. 10: 29-90 (1993). In certain embodiments, chemical stability of a protein is assessed by measuring the size distribution of the sample at several stages. These include, e.g., before particle formation (assessment of the feed solution), immediately after particle formation, and again after a period of storage, where storage takes place either within or in the absence of a suspension formulation carrier medium. In certain embodiments, the size distribution is assessed by size exclusion chromatography (SEC-HPLC).

The term "activity" refers to the ratio of a functional or structural aspect of an agent, e.g., a therapeutic or diagnostic agent, at two points in time. The denominator of the ratio corresponds to a measure of the functional or structural aspect of the agent in the feed solution, immediately in advance of droplet formation. The numerator of the ratio corresponds to the same measure of a functional or structural aspect of the agent at a later point in time, e.g., immediately after particle formation. In certain embodiments, the activity of a protein is assessed through size exclusion chromatography with a high performance liquid chromatography system (SEC-HPLC) or the proclivity of the protein for binding select targets.

The term "excipient" refers to an additive to a preparation or formulation, which may be useful in achieving a desired modification to the characteristics of the preparation or formulation. Such modifications include, but are not limited to, physical stability, chemical stability, and therapeutic efficacy. Exemplary excipients include, but are not limited to, a carbohydrate, a pH adjusting agent, a salt, a chelator, a mineral, a polymer, a surfactant, a protein stabilizer, an emulsifier, an antiseptic, an amino acid, an antioxidant, a protein, an organic solvent, or nutrient media.

The term "feed solution" refers to a preparation of the therapeutic or diagnostic agents in the first liquid, either as a solution, a slurry, or some other liquid form. In some embodiments, the preparation contains excipients and, optionally, a buffer.

The term "viscosity" is used to describe the property of a fluid acting to resist shearing flow. For the purposes of the present invention, viscosity can be determined using a rheometer, e.g., AR-G2 Rheometer (TA Instruments, USA), fitted with a cone and plate (2° /40 mm) at 25° C. at a specified shear rate. In certain embodiments, the viscosity is measured at a shear rate in the Newtonian regime. In other embodiments, the viscosity is measured at a shear rate of 100 $s^{-1}$ or greater, e.g., at 1000 $s^{-1}$ or greater than 1000 $s^{-1}$, or greater than 10,000 $s^{-1}$ or greater than 50,000 $s^{-1}$.

The term "solvent polarity" refers to the overall solvation capability (solvation power) of the solvent, which in turn depends on the action of all possible, nonspecific and specific, intermolecular interactions between solute ions or molecules and solvent molecules, excluding, however, those interactions leading to definite chemical alterations of the ions of molecules of the solute (Chem. Rev., 1994, 94, 2319-2358). A prediction of solvent polarity may be made from their dielectric constant. Solvents with high dielectric constants are considered more polar and those with low dielectric constants are considered less polar or nonpolar (<~15).

The term "vessel" refers to any embodiment of a container for a second liquid. Exemplary embodiments include an open bath, a closed bath, or a microfluidic junction, i.e., the tubing or channels within which and through which microfluidic droplet generation may proceed.

The term "primary desiccation" refers to a step by which a droplet comprising a first liquid is placed in contact with a second liquid and desiccated by the second liquid, e.g., through dispersal of the first liquid in the second liquid, and/or through evaporation.

The term "secondary desiccation" refers to a post-processing step by which the residual moisture and/or solvent content of the particles is modified. Exemplary methods of secondary desiccation include vacuum drying, with or without application of heat, lyophilization, fluidized bed drying, and slurry spray drying. Secondary desiccation may also be used to remove any washing liquids that are used to separate the particles from the second liquid.

Figure 1:
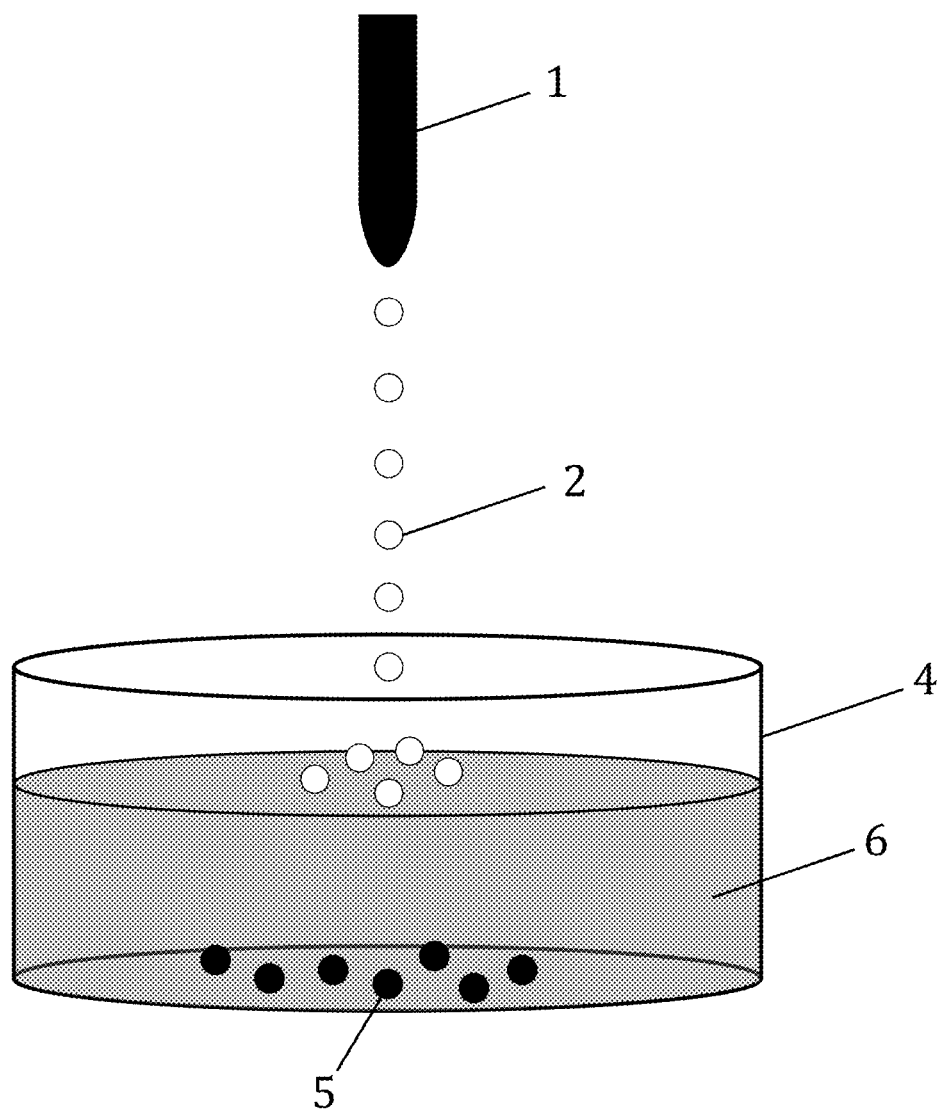
FIG. 1 is a scheme showing a droplet source 1 that produces droplets 2. The droplets 2 are collected by a vessel 4 that contains a second liquid 6. The density of the second liquid 6 is between that of the droplets 2 and the particles 5, such that the droplets 2 float on the surface of the second liquid 6. The droplets 2 dry to form particles 5 that, unlike the droplets, are more dense than the second liquid 6. The particles 5, therefore, do not float on the surface of the second liquid 6.

FIG. 7 is a scheme showing a vessel 4 containing a second liquid. A wire electrode 14 is disposed in the vessel.

FIG. 8 is a scheme showing a vessel 4 containing a second liquid. The bottom of the vessel 4 is an electrode 15.

FIGS. 9A-28B are series of images of human IgG particles that were formed through methods of the invention.

FIG. 29A-29B depicts images of bovine IgG particles that were formed through methods of the invention.

FIGS. 30A-31B are series of images of human IgG particles that were formed through methods of the invention.

FIGS. 32A-32B depict images of mucin particles that were formed through methods of the invention.

FIG. 33 depicts an image oligonucleotide particles that were formed through methods of the invention.

FIGS. 34-40 are images of mAb particles that were formed through methods of the invention.

DETAILED DESCRIPTION

The invention provides methods for the preparation of particles including one or more agents, e.g., therapeutic or diagnostic agents. The particles can be formed by creating droplets of a first liquid, e.g., including an agent, and removing the first liquid, e.g., through its dispersal in a second liquid and/or evaporation, to solidify the droplets. Advantageously, the process of forming the particles does not significantly alter the structure or activity of the agents and may enhance the stability of the agents. For example, the particles may be stored for long periods of time without significant loss of activity, and in some embodiments, without the need for refrigeration. These particles may be used to generate stabilized pharmaceutical compositions for storage or other logistical purposes, pharmaceutical suspensions, pharmaceutical powder formulations (e.g., inhalable powders, injectable powders), creams or other topical pastes, nutraceuticals, or cosmetics.

Droplets

Droplets of the invention can be formed through any of several techniques that are known in the art. These include rotary atomization, pneumatic atomization, ultrasonic atomization, sonic atomization, vibrating mesh nebulization, jet atomization, microfluidic droplet generation, electrospray, or homogenization. The droplets include a first liquid and one or more agents, e.g., a therapeutic and/or diagnostic agent. The concentration of any agent, e.g., a therapeutic or diagnostic agent, in the first liquid can be in the range of 0.0001 to 1000 mg/mL, e.g., 100 to 900 mg/mL, 200 to 800 mg/mL, 200 to 700 mg/mL, 200 to 600 mg/mL, or 300 to 500 mg/mL.

The first liquid can be aqueous or an organic solvent. For example, when aqueous, the first liquid may be water, 0.9% saline, lactated Ringer's solution, dextrose 5%, or a buffer. In some embodiments, the buffer is an acetate buffer, a histidine buffer, a succinate buffer, HEPES buffer, tris buffer, carbonate buffer, citrate buffer, phosphate buffer, glycine buffer, barbital buffer, and cacodylate buffer. The first liquid can further include, e.g., a carbohydrate, a pH adjusting agent, a salt, a chelator, a mineral, a polymer, a surfactant, a protein stabilizer, an emulsifier, an antiseptic, an amino acid, an antioxidant, a protein, an organic solvent, a paraben, a bactericide, a fungicide, a vitamin, a preservative, and/or nutrient media. For example, oligopeptides, e.g., trileucine, can be used as stabilizers for particles. In some cases, the liquid can further include an analgesic, such as acetaminophen or lidocaine. In some embodiments, the carbohydrate is dextran, trehalose, sucrose, agarose, mannitol, lactose, sorbitol, or maltose. In some embodiments, the pH adjusting agent is acetate, citrate, glutamate, glycinate, histidine, lactate, maleate, phosphate, succinate, tartrate, bicarbonate, aluminum hydroxide, phosphoric acid, hydrochloric acid, DL-lactic/glycolic acids, phosphorylethanolamine, tromethamine, imidazole, glyclyglycine, or monosodium glutamate. In some embodiments, the salt is sodium chloride, calcium chloride, potassium chloride, sodium hydroxide, stannous chloride, magnesium sulfate, sodium glucoheptonate, sodium pertechnetate, or guanidine hydrochloride. In some embodiments, the chelator is disodium edetate or ethylenediaminetetraacetic acid. In some embodiments, the mineral is calcium, zinc, or titanium dioxide. In some embodiments, the polymer is propyleneglycol, glucose star polymer, silicone polymer, polydimethylsiloxane, polyethylene glycol, carboxymethylcellulose, poly(glycolic acid), poly(lactic-co-glycolic acid), or polylactic acid. In some embodiments, the surfactant is polysorbate, magnesium stearate, sodium dodecyl sulfate, TRITON™ N-101, glycerin, or polyoxyethylated castor oil. In some embodiments, the protein stabilizer is acetyltryptophanate, caprylate, N-acetyltryptophan, trehalose, PEG 200, PEG 300, PEG 3350, PEG 8000, PEG 10000, PEG 20000, polyoxamers, polyvinylpyrrolidone, polyacrylic acids, poly(vinyl) polymers, polyesters, polyaldehydes, tert-polymers, polyamino acids, hydroxyethyl starch, N-methyl-2-pyrrolidone, sorbitol, sucrose, or mannitol, e.g., trehalose, PEG 200, PEG 300, PEG 3350, PEG 8000, PEG 10000, PEG 20000, polyoxamers, polyvinylpyrrolidone, polyacrylic acids, poly(vinyl) polymers, polyesters, polyaldehydes, tert-polymers, polyamino acids, hydroxyethyl starch, N-methyl-2-pyrrolidone, sorbitol, sucrose, or mannitol. In some embodiments, the emulsifier is selected from polysorbate 80, polysorbate 20, sorbitan monooleate, ethanolamine, polyoxyl 35 castor oil, poloxyl 40 hydrogenated castor oil, carbomer 1342, a corn oil-mono-di-triglyceride, a polyoxyethylated oleic glyceride, or a poloxamer. In some embodiments, the antiseptic is phenol, m-cresol, benzyl alcohol, 2-phenyloxyethanol, chlorobutanol, neomycin, benzethonium chloride, gluteraldehyde, or beta-propiolactone. In some embodiments, the amino acid is asparagine, L-arginine, histidine, glycine, or glutamine. In some embodiments, the antioxidant is glutathione, ascorbic acid, cysteine, or tocopherol. In some embodiments, the protein is protamine, protamine sulfate, or gelatin. In some embodiments, the organic solvent may be dimethyl sulfoxide or N-methyl-2-pyrrolidone. In some embodiments, the preservative is methyl hydroxybenzoate, thimerosal, parabens, formaldehyde, or castor oil. The paraben can be a parahydroxybenzoate. The bactericide can be benzalkonium chloride. In certain embodiments, the liquid may further include an analgesic, such as acetaminophen or lidocaine. In some embodiments, the liquid can further include adenine, tri-n-butyl phosphate, octa-fluoropropane, white petroleum, or p-aminophenyl-p-anisate.

In some embodiments, the organic solvent is acetic acid, acetone, acetonitrile, alkanes (e.g., hexanes, heptane), amyl acetate, butanol, butyl acetate, chlorobenzene, chloroform, cumene, cyclohexane, 1,2-dichloroethene, dichloromethane, diethyl ether, dimethoxyethane, dimethylacetamide, dimethylformamide, dimethyl sulfoxide, 1,4-dioxane, ethanol, 2-ethoxyethanol, ethyl acetate, ethyl nitrate, ethyleneglycol, formic acid, hydrazine, isopropanol, methanol, methyl acetate, 2-methyl-1-butanol, 2-methyl-1-propanol, methylbutyl ketone, methylcyclohexane, methylethyl ketone, methylpyrrolidone, methyl tert-butyl ether, nitromethane, propanol, propyl acetate, sulfolane, sarcosine, tetrahydrofuran, tetralin, toluene, 1,1,2-tricholoroethane, triethylamine, urea, xylene, or any combination thereof.

In some embodiments, the droplet has a core-shell morphology in the which the first liquid (the droplet "core") is surrounded by one or more concentric layers of additional liquid (the droplet "shell(s)"), each of which may or may not be defined by a unique set of components and/or a unique concentration of components. Each shell liquid can be aqueous or an organic solvent and include one or more agents, e.g., therapeutic or diagnostic agents. The concentration of any agent, e.g., a therapeutic or diagnostic agent, in any shell liquid can be in the range of 0.0001 to 1000 mg/mL, e.g., 100 to 900 mg/mL, 200 to 800 mg/mL, 200 to 700 mg/mL, 200 to 600 mg/mL, or 300 to 500 mg/mL. For example, when aqueous, any of the shell liquids may be water, 0.9% saline, lactated Ringer's solution, dextrose 5%, or a buffer. In some embodiments, the buffer is an acetate buffer, a histidine buffer, a succinate buffer, HEPES buffer, tris buffer, carbonate buffer, citrate buffer, phosphate buffer, glycine buffer, barbital buffer, and cacodylate buffer. The shell liquid can further include, e.g., a carbohydrate, a pH adjusting agent, a salt, a chelator, a mineral, a polymer, a surfactant, a protein stabilizer, an emulsifier, an antiseptic, an amino acid, an antioxidant, a protein, an organic solvent, a paraben, a bactericide, a fungicide, a vitamin, a preservative, and/or nutrient media. In some embodiments, the carbohydrate is dextran, trehalose, sucrose, agarose, mannitol, lactose, sorbitol, or maltose. In some embodiments, the pH adjusting agent is acetate, citrate, glutamate, glycinate, histidine, lactate, maleate, phosphate, succinate, tartrate, bicarbonate, aluminum hydroxide, phosphoric acid, hydrochloric acid, DL-lactic/glycolic acids, phosphoryletha-nolamine, tromethamine, imidazole, glyclyglycine, or monosodium glutamate. In some embodiments, the salt is sodium chloride, calcium chloride, potassium chloride, sodium hydroxide, stannous chloride, magnesium sulfate, sodium glucoheptonate, sodium pertechnetate, or guanidine hydrochloride. In some embodiments, the chelator is disodium edetate or ethylenediaminetetraacetic acid. In some embodiments, the mineral is calcium, zinc, or titanium dioxide. In some embodiments, the polymer is propyleneglycol, glucose star polymer, silicone polymer, polydimethylsiloxane, polyethylene glycol, carboxymethylcellulose, poly(glycolic acid), poly(lactic-co-glycolic acid), or polylactic acid. In some embodiments, the surfactant is polysorbate, magnesium stearate, sodium dodecyl sulfate, TRITON™ N-101, glycerin, or polyoxyethylated castor oil. In some embodiments, the protein stabilizer is acetyltryptophanate, caprylate, N-acetyltryptophan, trehalose, PEG 200, PEG 300, PEG 3350, PEG 8000, PEG 10000, PEG 20000, polyoxamers, polyvinylpyrrolidone, polyacrylic acids, poly(vinyl) polymers, polyesters, polyaldehydes, tert-polymers, polyamino acids, hydroxyethyl starch, N-methyl-2-pyrrolidone, sorbitol, sucrose, or mannitol, e.g., trehalose, PEG 200, PEG 300, PEG 3350, PEG 8000, PEG 10000, PEG 20000, polyoxamers, polyvinylpyrrolidone, polyacrylic acids, poly(vinyl) polymers, polyesters, polyaldehydes, tert-polymers, polyamino acids, hydroxyethyl starch, N-methyl-2-pyrrolidone, sorbitol, sucrose, or mannitol. In some embodiments, the emulsifier is selected from polysorbate 80, polysorbate 20, sorbitan monooleate, ethanolamine, polyoxyl 35 castor oil, poloxyl 40 hydrogenated castor oil, carbomer 1342, a corn oil-mono-di-triglyceride, a polyoxyethylated oleic glyceride, or a poloxamer. In some embodiments, the antiseptic is phenol, m-cresol, benzyl alcohol, 2-phenyloxyethanol, chlorobutanol, neomycin, benzethonium chloride, gluteraldehyde, or beta-propiolactone. In some embodiments, the amino acid is asparagine, L-arginine, histidine, glycine, or glutamine. In some embodiments, the antioxidant is glutathione, ascorbic acid, cysteine, or tocopherol. In some embodiments, the protein is protamine, protamine sulfate, or gelatin. In some embodiments, the organic solvent may be dimethyl sulfoxide or N-methyl-2-pyrrolidone. In some embodiments, the preservative is methyl hydroxybenzoate, thimerosal, parabens, formaldehyde, or castor oil. The paraben can be a parahydroxybenzoate. The bactericide can be benzalkonium chloride. In certain embodiments, the shell liquid may further include an analgesic, such as acetaminophen or lidocaine. In some embodiments, the shell liquid can further include adenine, tri-n-butyl phosphate, octa-fluoropropane, white petroleum, or p-aminophenyl-p-anisate.

In some embodiments, the organic solvent is acetic acid, acetone, acetonitrile, alkanes (e.g., hexanes, heptane), amyl acetate, butanol, butyl acetate, chlorobenzene, chloroform, cumene, cyclohexane, 1,2-dichloroethene, dichloromethane, diethyl ether, dimethoxyethane, dimethylacetamide, dimethylformamide, dimethyl sulfoxide, 1,4-dioxane, ethanol, 2-ethoxyethanol, ethyl acetate, ethyl nitrate, ethyleneglycol, formic acid, hydrazine, isopropanol, methanol, methyl acetate, 2-methyl-1-butanol, 2-methyl-1-propanol, methylbutyl ketone, methylcyclohexane, methylethyl ketone, methylpyrrolidone, methyl tert-butyl ether, nitromethane, propanol, propyl acetate, sulfolane, sarcosine, tetrahydrofuran, tetralin, toluene, 1,1,2-tricholoroethane, triethylamine, urea, xylene, and any combination thereof.

In some embodiments, a surfactant in the first liquid and/or the shell liquid(s) prevents coalescence of the droplets. Surfactants useful for the invention include, but are not limited to, polysorbate, magnesium stearate, sodium dodecyl sulfate, glycerin, PEGylated phospholipids, TRITONs, e.g., TRITON™ N-101, sorbitan monopalmitate, polysorbate 80, 4-lauryl etherpolyoxyethylene polyoxypropylene copolymer, ethoxylated sorbitan ester, ethoxylated castor oil, a fatty acid, a bile salt, an ethoxylated glyceride, an ethoxylated fatty acid, a sphingolipid, a sorbitan ester, polyglycoside, cetyl alcohol, cocamide, glucosides, maltosides, monolaurin, polyglycol steroidal esters, fatty acid esters, a poloxamer, phospholipids, salts of fatty acids, sterol alcohols and their salts, cationic surfactants (e.g., cetyltrimethylammonium bromide (CTAB), benzalkonium chloride (BAC)), anionic surfactants (e.g., docusates, sulfonates, carboxylates, and alkyl ether phosphates), amphoteric surfactants (e.g., alkyl iminopropionates), and zwitterionic detergents (e.g., sultaines and betaines), or any combination thereof.

In some embodiments, one or more of the shell layers is a hydrogel, ionogel, organogel, or some combination thereof. Exemplary hydrogels are prepared from polymers such as collagen, chitosan, methylcellulose, dextran, alginate, agarose, poly(methyl methacrylate), poly(amido amine), poly(ethyleneimine), polyethylene oxide, gelatin, hyaluronic acid, and any combination thereof, and may contain water, aqueous solutions, and other polar solvents. Exemplary organogels are prepared form organogelators such as 4-tert-butyl-1-aryl cyclohexanols, L-lysine derivatives, poly(ethylene glycol), polycarbonate, polyesters, polyalkenes, oxalyl amide derivatives containing alkyl ester groups, and low molecular weight compounds such as fatty acids and n-alkanes. They contain a non-polar solvent phase. Ionogels are analogous to organogels with the exception that the solvent phase is an ionic liquid.

In some embodiments the, the droplets are electrically charged. As a fraction of the Rayleigh limit, the droplets may on average be charged from 0 to 1, e.g., from 0.1 to 1.0, from 0.2 to 1.0, from 0.3 to 1.0, from 0.4 to 1.0, or from 0.5 to 1.0. In some embodiments, charging assists in the mitigation of droplet coalescence.

Formation of Particles

Figure 2:
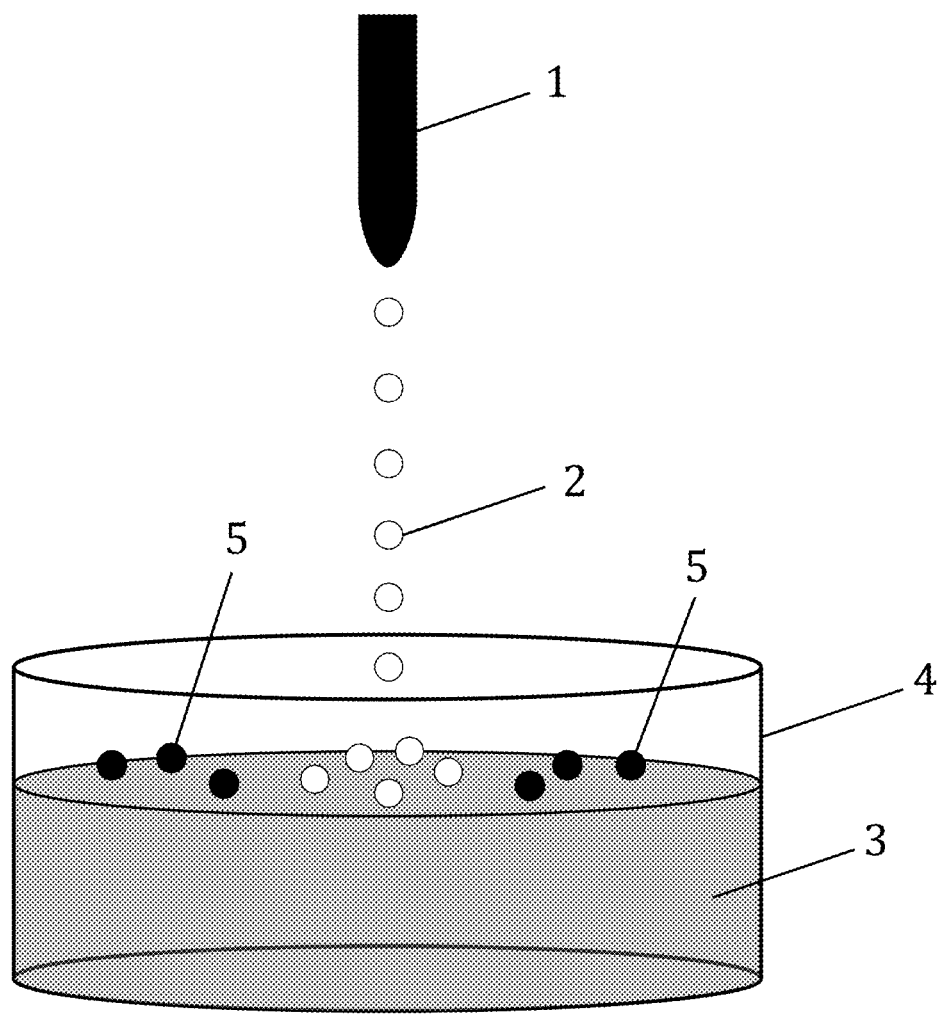
FIG. 2 is a scheme showing a droplet source 1 that produces droplets 2. The droplets 2 are collected by a vessel 4 that contains a second liquid 3. The density of the second liquid 3 is greater than that of the droplets 2, such that the droplets 2 float on the surface of the second liquid 3. The droplets 2 dry to form particles 5 that are also less dense than the second liquid 3. Similar to the droplets 2, the particles formed 5 float on the surface of the second liquid 3.
Figure 3:
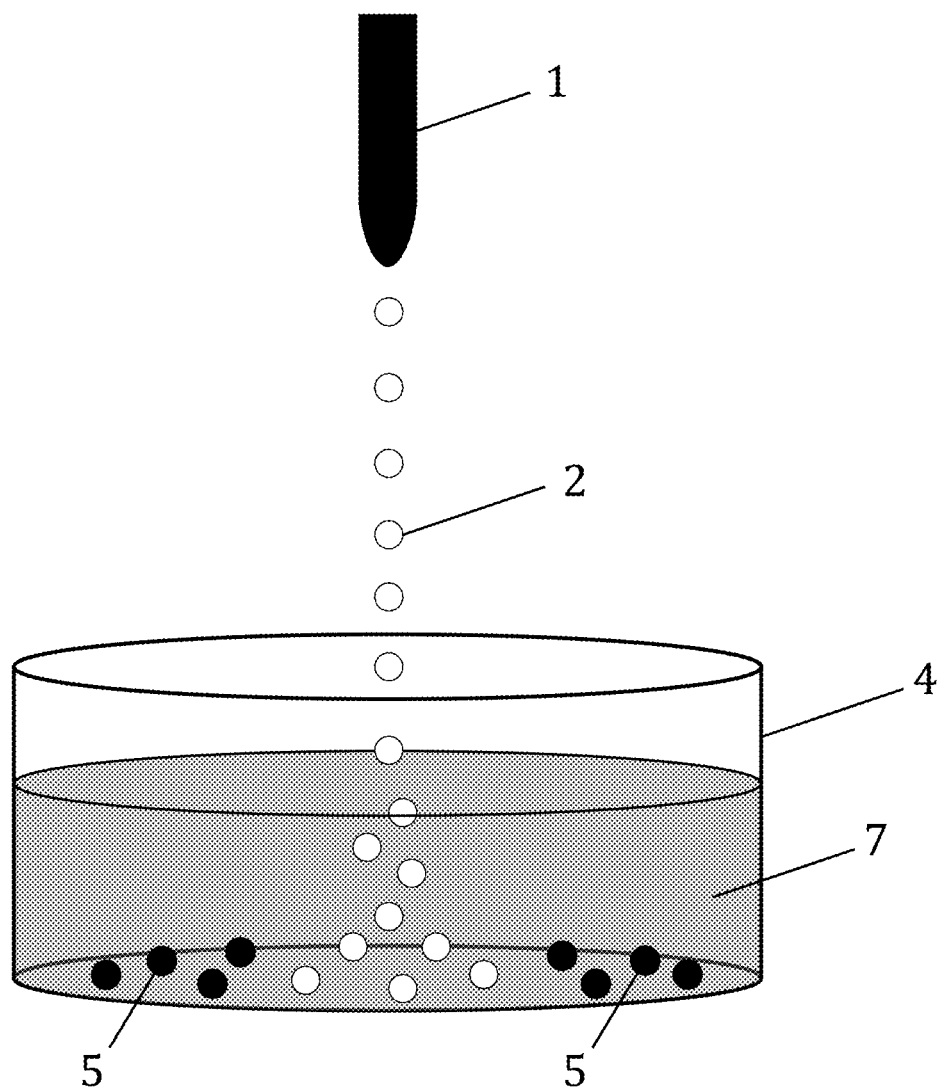
FIG. 3 is a scheme showing a droplet source 1 that produces droplets 2. The droplets 2 are collected by a vessel 4 that contains a second liquid 7. The density of the second liquid 7 is lower than or matching that of the droplets 2, such that the droplets 2 do not float on the surface of the second liquid 7. The droplets 2 dry to form particles 5 that are more dense than the second liquid 7. Similar to the droplets 2, the formed particles 5, therefore, do not float on the surface of the second liquid 7.
Figure 4:
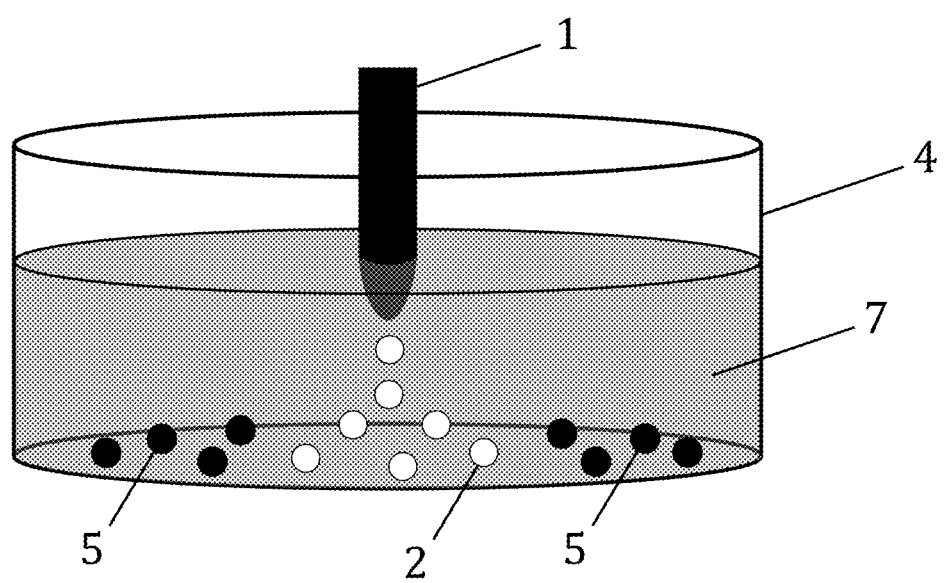
FIG. 4 is a scheme showing a droplet source 1 that produces droplets 2. The droplet source 1 is at least partially immersed in a second liquid 7 contained by a vessel 4, such that the droplets 2 are immediately in contact with the second liquid 7. The droplets 2 dry to form particles 5. The droplets and particles may or may not float on the second liquid 7.

Particles are formed by placing droplets that include a first liquid in contact with a second liquid that facilitates removal of the first liquid. In some embodiments, the droplets are formed in a separate medium and placed into contact with the second liquid thereafter, e.g., by dripping or spraying them into or onto the second liquid (FIGS. 1-3). In other embodiments, the droplets are formed within the second liquid, such that they are immediately in contact (FIG. 4).

In some embodiments, particles are formed after the first liquid disperses throughout the second liquid, such as through a diffusion process. In such embodiments the second liquid may have varying degrees of miscibility with the first liquid and represent a weakly or negligibly solubilizing medium in relation to the components of the particles, e.g., the therapeutic or diagnostic agents. The agents, e.g., therapeutic or diagnostic agents, are typically less soluble in the second liquid relative to the first liquid in the timeframe of or under the conditions of production, e.g., at least 5, 10, 100, or 1000 times less soluble. In certain embodiments, the second liquid is an oil, organic solvent, aqueous solution, ionic liquid, or any combination thereof. Exemplary oils are coconut oil, corn oil, cottonseed oil, fish oil, grape seed oil, hazelnut oil, hydrogenated vegetable oils, lime oil, olive oil, palm seed oil, peanut oil, peppermint oil, safflower oil, sesame oil, soybean oil, sunflower oil, walnut oil, castor oil, polyoxyl 35 castor oil, or any combination thereof.

Exemplary organic solvents are benzyl benzoate, acetone, ethyl lactate, dimethyl isosorbide, dimethyl sulfoxide, glycofurol, diglyme, methyl tert-butyl ether, polyethylene glycol, 2-pyrrolidone, tetrahydrofurfuryl alcohol, trigylcerides, methyl acetate, ethyl lactate, ethyl acetate, propyl acetate, butyl acetate, amyl acetate, chloroform, dichloromethane, ethanol, methanol, propanol, butanol, acetonitrile, diethyl ether, diglyme, 1,2-dimethoxyethane, dimethylformamide, pentane, toluene, tocopherol, octa-fluoropropane, (perfluorohexyl)octane, n-acetyltryptophan, trigylcerides, triglycerides of the fractionated plant fatty acids C8 and C10 (e.g., MIGLYOL® 810 and MIGLOYL® 812N), propylene glycol diesters of saturated plant fatty acids C8 and C10 (e.g., MIGLYOL® 840), ethyl laurate, methyl caprylate, methyl caprate, methyl myristate, methyl oleate, methyl linoleate, dimethyl adipate, dibutyl suberate, diethyl sebacate, ethyl macadamiate, trimethylolpropane triisosterate, isopropyl laurate, isopropyl myristate, diethyl succinate, polysorbate esters, ethanol amine, propanoic acid, octanoic acid, triacetin, citral, anisole anethol, benzaldehyde, linalool, caprolactone, phenol, thioglycerol, dimethylacetamide, transcutol, Solketal, ethyl formate, ethyl hexyl acetate, eugenol, clove bud oil, diethyl glycol monoether, ethyl lactate, tocopherol, octa-fluoropropane, (perfluorohexyl)octane, n-acetyltryptophan, trigylcerides, triglycerides of the fractionated plant fatty acids C8 and C10, ethyl laurate, methyl caprylate, methyl caprate, methyl myristate, methyl oleate, methyl linoleate, dimethyl adipate, dibutyl suberate, diethyl sebacate, ethyl macadamiate, trimethylolpropane triisosterate, isopropyl laurate, isopropyl myristate, diethyl succinate, polysorbate esters, ethanol amine, propanoic acid, octanoic acid, triacetin, citral, anisole anethol, benzaldehyde, linalool, phenol, thioglycerol, dimethylacetamide, ethyl formate, ethyl hexyl acetate, eugenol, clove bud oil, diethyl glycol monoether, benzyl alcohol, dimethyl isosorbide, ethyl ether, isopropyl acetate, methyl isobutyl ketone, methyl tert-butyl ether, N-methyl pyrrolidone, perfluorodecalin, 2-pyrrolidone, ethyl oleate, ethyl caprate, dibutyl adipate, fatty acid esters, hexanoic acid, octanoic acid, triacetin, diethyl glycol monoether, gamma-butyrolactone, eugenol, clove bud oil, citral, limonene, polyoxyl 40 hydrogenated castor oil, polyoxyl 35 castor oil, octanol, hexanol, decanol, gamma-butyrolactone, tocopherol, octa-fluoropropane, (perfluorohexyl)octane, n-acetyltryptophan, ethyl laurate, methyl caprylate, methyl caprate, methyl myristate, methyl oleate, methyl linoleate, dimethyl adipate, dibutyl suberate, diethyl sebacate, ethyl macadamiate, trimethylolpropane triisosterate, isopropyl laurate, isopropyl myristate, diethyl succinate, polysorbate esters, ethanol amine, propanoic acid, citral, anisole, anethol, benzaldehyde, linalool, caprolactone, phenol, thioglycerol, dimethylacetamide, TRANSCUTOL® HP, solketal, isosorbide dimethyl ether, ethyl formate, ethyl hexyl acetate, and any combination thereof.

In some embodiments, the organic solvent is ethyl lactate, tocopherol, octa-fluoropropane, (perfluorohexyl)octane, n-acetyltryptophan, trigylcerides, triglycerides of the fractionated plant fatty acids C8 and C10, ethyl laurate, methyl caprylate, methyl caprate, methyl myristate, methyl oleate, methyl linoleate, dimethyl adipate, dibutyl suberate, diethyl sebacate, ethyl macadamiate, trimethylolpropane triisosterate, isopropyl laurate, isopropyl myristate, diethyl succinate, polysorbate esters, ethanol amine, propanoic acid, octanoic acid, triacetin, citral, anisole anethol, benzaldehyde, linalool, caprolactone, phenol, thioglycerol, dimethylacetamide, ethyl formate, ethyl hexyl acetate, eugenol, clove bud oil, diethyl glycol monoether, benzyl alcohol, dimethyl isosorbide, ethyl ether, isopropyl acetate, methyl isobutyl ketone, methyl tert-butyl ether, N-methyl pyrrolidone, perfluorodecalin, 2-pyrrolidone, ethyl oleate, ethyl caprate, dibutyl adipate, fatty acid esters, hexanoic acid, octanoic acid, triacetin, diethyl glycol monoether, gamma-butyrolactone, eugenol, clove bud oil, citral, limonene, polyoxyl 40 hydrogenated castor oil, polyoxyl 35 castor oil, octanol, hexanol, decanol, gamma-butyrolactone, tocopherol, octa-fluoropropane, (perfluorohexyl)octane, n-acetyltryptophan, ethyl laurate, methyl caprylate, methyl caprate, methyl myristate, methyl oleate, methyl linoleate, dimethyl adipate, dibutyl suberate, diethyl sebacate, ethyl macadamiate, trimethylolpropane triisosterate, isopropyl laurate, isopropyl myristate, diethyl succinate, polysorbate esters, ethanol amine, propanoic acid, citral, anisole, anethol, benzaldehyde, linalool, caprolactone, phenol, thioglycerol, dimethylacetamide, TRANSCUTOL® HP, solketal, isosorbide dimethyl ether, ethyl formate, ethyl hexyl acetate, and any combination thereof.

Acetate organic solvents, e.g., alkyl acetates (such as methyl acetate, ethyl acetate, propyl acetate, butyl acetate, 2-ethyl hexyl acetate, and amyl acetate), aryl acetates (such as phenyl acetate and tolyl acetate), and aryl alkyl acetates (such benzyl acetate and phenethyl acetate), are exemplary organic solvents.

Exemplary aqueous liquids may contain stabilizers, e.g., crowding agents, such as salt (e.g., sodium chloride), sugars and sugar alcohols (e.g., sorbitol, dextran 40, dextran 6000, or trehalose), or polymers (e.g., PEG 3350, PEG 300, PEG 8000, PEG 20k, Ficoll 400, Ficoll 70, or polyvinylpyrrolidone, e.g., Povidone). Exemplary ionic liquids contain pyridinium, pyridazinium, pyrimidinium, pyrazinium, imidazolium, pyrazolium, thiazolium, oxazolium, triazolium, ammonium, sulfonium, halides, sulfates, sulfonates, carbonates, phosphates, bicarbonates, nitrates, acetates, $PF_6^-$, $BF_4^-$, triflate, nonaflate, bis(triflyl)amide, trifluoroacetate, heptafluorobutanoate, haloaluminate, or any combination thereof.

In some embodiments, where the first and second liquids are aqueous, particles are obtained via osmotic drying of the droplets. The second liquid used to dry the particles includes a high concentration of a solute, e.g., at least 0.03 osmol, at least 0.2 osmol, at least 1.0 osmol, or at least 1.2 osmol. Such solutions may include salts, sugars, sugar alcohols, polymers, and/or proteins. An exemplary salt is sodium chloride. Exemplary sugars and sugar alcohols include sorbitol, dextran 40, dextran 6000, and trehalose. Exemplary polymers include PEG 3350, PEG 300, PEG 8000, PEG 20k, Ficoll 400, Ficoll 70, and polyvinylpyrrolidone, e.g., povidone. An exemplary protein is bovine serum albumin.

In some embodiments, the second liquid may be a liquid surfactant or include a surfactant. Exemplary surfactants are PEGylated phospholipids, TRITONs, sorbitan monopalmitate, polysorbate 80, 4-lauryl etherpolyoxyethylene polyoxypropylene copolymer, ethoxylated sorbitan ester, ethoxylated castor oil, a fatty acid, monolaurin, polyglycol steroidal esters, a poloxamer, phospholipids, a bile salt, an ethoxylated glyceride, an ethoxylated fatty acid, a sphingolipid, a sorbitan ester, polyglycoside, cetyl alcohol, cocamide, glucosides, maltosides, fatty acid esters, cetyl alcohol, cocamide, salts of fatty acids, sterol alcohols and their salts, cationic surfactants (e.g., cetyltrimethylammonium bromide (CTAB), benzalkonium chloride (BAC)), anionic surfactants (e.g., docusates, sulfonates, carboxylates, and alkyl ether phosphates), amphoteric surfactants (e.g., alkyl iminopropionates), and zwitterionic detergents (e.g., sultaines and betaines), and any combination thereof.

Figure 5:
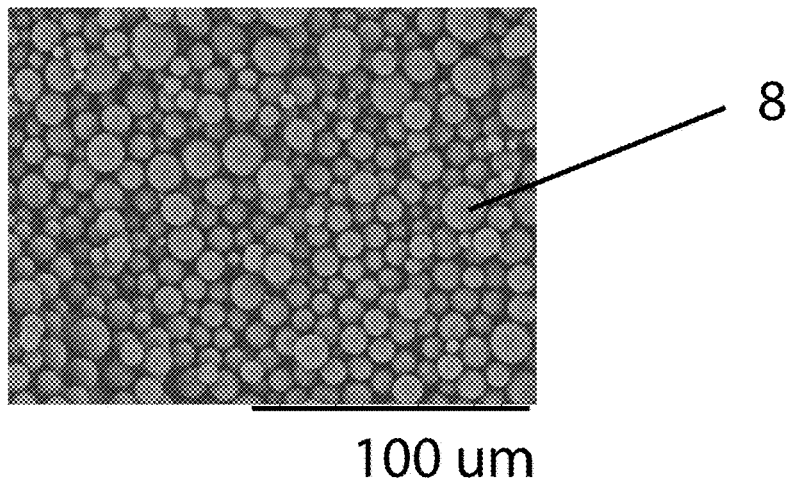
FIG. 5 is a series of images of particles of human IgG protein that were formed from an aqueous solution under different drying conditions. Among other drying properties, particles 8 have high transport numbers as solute transport in the droplet is fast compared to solute transport out of the droplet. Among other drying properties, particles 9 and 10 have low transport numbers as solute transport in the droplet is slow compared to solvent transport out of the droplet.
Figure 5:
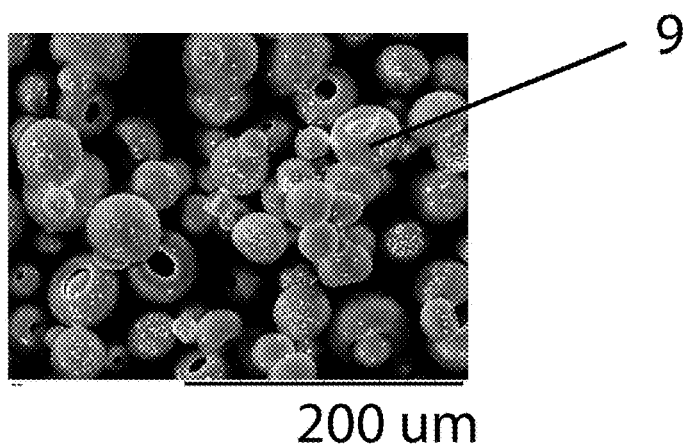
Figure 5:
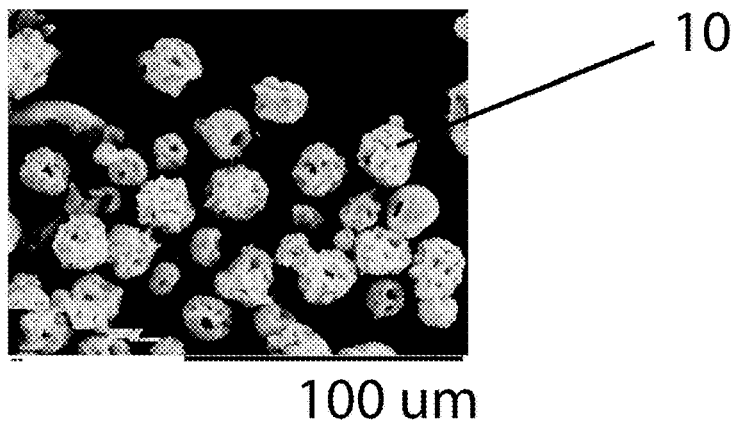

In some embodiments, the drying rate of the droplets, the transport number (i.e., the ratio of the solute transport rate within the drop to the transport rate of the first liquid away from the drop), and the particle formation dynamics following solute precipitation or phase separation within the droplet, among other important parameters of the particle formation process, are modulated by controlling, e.g., the temperature, viscosity, surface tension, and/or solvent polarity of the first liquid and/or the second liquid. The miscibility of the two liquids, i.e., the solubility of the first liquid in the second liquid, and the degree to which the second liquid is pre-saturated with the first liquid may also be controlled. Notably, such modulation can influence the size, morphology, density, porosity, and surface energy of the particles. It can also help to regulate important physicochemical properties which can be difficult to address when drying without the second liquid, e.g., in air, as with conventional spray drying. These properties include the dissolution rates of the particles and their flow properties (R. Vehring, Pharmaceutical Res., 2008, 25, 999-1022). Several particle morphologies which can be achieved by judicious control of the second liquid, which in turn modulates various parameters of the particle formation process, are illustrated in FIG. 5.

Depending on the chosen process conditions, drying of the particles may occur over a period of nanoseconds to days. In embodiments where the first liquid is aqueous and where the second liquid is an organic solvent, drying times can vary, e.g., between 1 us and 1000 s depending on the solvent chemistry. Exemplary transport numbers during the drying period are greater than 1, indicating a regime where transport of solutes within the drop is fast as compared to the radial velocity of the receding droplet surfaces. Such transport numbers tend to correlate with regular, spherical particle morphologies. In some embodiments, the transport number is between 0 and 1, in which case the droplet surface moves fast in relation to the solutes, thereby leading to an enriched layer of solute near the surface of the drop. Situations of this type typically correlate with irregular particle morphologies.

In some embodiments, the temperature of the first and/or second liquid is controlled. The first liquid and the second liquid may be kept at the same temperature or at different temperatures. In some embodiments, the temperature of each liquid may be, independently, from −100 to 300° C., e.g., −20 to 180° C., 1 to 100° C., 1 to 50° C., or 20 to 50° C.

In some embodiments, the viscosity of the first and/or second liquid is controlled. In some embodiments, the viscosity of the first liquid and/or the second liquid affects a coefficient of diffusion or dispersal of the first liquid in the second liquid, thereby regulating the drying rate and transport number. The viscosity of each liquid may be, independently, from 0.01 cP to 10,000 cP, e.g., from 0.01 to 1,000 cP, from 0.01 to 100 cP, from 0.01 to 50 cP, from 0.01 to 25 cP, from 0.01 to 10 cP, from 0.01 to 5 cP, from 0.01 to 1 cP. Methods of controlling viscosity include temperature regulation and viscosity modifying additives. Mixtures of liquids may also be used to control viscosity.

In some embodiments, the solvent polarity of the first liquid and/or second liquid is controlled. In some embodiments, the solvent polarity of each liquid may have a dielectric constant, independently, from about 1 to about 200, e.g., about 1 to about 180, about 10 to about 140, about 30 to about 120, about 50 to about 100, or 70 to about 80.

In some embodiments, the solubility of the first liquid in the second liquid is controlled. In some embodiments, the solubility of the first liquid in the second liquid ranges from 0 g/L to fully miscible, e.g., from 0 to 100 g/L, from 0 to 50 g/L, from 0 to 25 g/L, or from 0 to 10 g/L. Methods of controlling the solubility include temperature regulation. Mixtures of liquids may also be used to control solubility. In some embodiments, the first liquid is placed in contact with the second liquid, and the solubility is adjusted thereafter by modifying the composition of the second liquid, e.g., by adjusting the relative ratios of the components of the second liquid.

In some embodiments, the saturation level of the first liquid in the second liquid is controlled. The saturation level can range from 0 to 100%, e.g., from 0 to 50%, from 0 to 10%, from 0 to 5%, or from 0 to 1%.

In some embodiments, the second liquid is a mixture of two or more liquids. In some embodiments, the mixture is used to tune the viscosity and/or polarity of the second liquid. In some embodiments, the mixture may also be used to tune the solubility of the first liquid in the second liquid. Since such properties can affect the rate and transport number associated with the drying process, they may be used to directly control various particle properties (e.g., size, morphology, density, etc.) through simple adjustment of the relative ratios of the liquids comprising the mixture. Consider, for example, a two-part mixture for which the first liquid is more soluble in one component (Component A) than the other (Component B). In certain embodiments, increasing the relative quantify of Component B will yield particles which are rounder than what would otherwise be achievable using only Component A. For two-part mixtures, one liquid in the mixture can have a concentration from 0 to 99.9999 vol %, e.g., from 0 to 99 vol %, from 0 to 95 vol %, from 0 to 90 vol %, from 0 to 75 vol %, from 0 to 50 vol %, from 0 to 25 vol %, from 0 to 10 vol %, from 0 to 5 vol %, from 0 to 1 vol %, or from 0 to 0.0001 vol %. Exemplary two-part mixtures include benzyl benzoate/acetone (e.g., 5-30% benzyl benzoate, such as 5:95, 10:90, 15:85, 20:80, 25:75, or 30:70), isopropyl alcohol/sesame oil (e.g., 35-65% isopropyl alcohol, such as about 35:65, 40:60, 45:55, 50:50, 55:45, 60:40, or 65:35), hexanes/ethanol (e.g., 10-35% hexanes, such as about 10:90, 15:85, 20:80, 25:75, 30:70, or 35:65), toluene/acetonitrile (e.g., 10-35% toluene, such as about 10:90, 15:85, 20:80, 25:75, 30:70, or 35:65), cottonseed oil/butyl acetate (e.g., 10-35% cottonseed oil, such as about 10:90, 15:85, 20:80, 25:75, 30:70, or 35:65), toluene/ethyl acetate (e.g., 10-35% toluene, such as about 10:90, 15:85, 20:80, 25:75, 30:70, or 35:65), diethyl ether/isopropanol (e.g., 5-30% diethyl ether, such as about 5:95, 10:90, 15:85, 20:80, 25:75, or 30:70), tetrahydrofuran/pentane (e.g., 35-65% THF, such as about 35:65, 40:60, 45:55, 50:50, 55:45, 60:40, or 65:35), safflower oil/methanol (e.g., 25-55% safflower oil, such as about 25:75, 30:70, 35:65, 40:60, 45:55, 50:50, or 55:45), and lime oil/acetone (5-30% lime oil, such as about 5:95, 10:90, 15:85, 20:80, 25:75, or 30:70). One of ordinary skill in the art would be able to choose appropriate liquid combinations and ratios, e.g., components of the second liquid, to control the particle drying speed and transport number.

A surfactant may be used as a component of the second liquid. In some embodiments, the surfactant helps to establish an interface between the first and second liquid, and in some instances to regulate the drying speed and transport number. In some embodiments, the surfactant may also limit coalescence of the drops during the drying process and/or mitigate damage to the agents, e.g., therapeutic or diagnostic agents, at the interface between the first liquid and the second liquid. The concentration of the surfactant in the second liquid can range from 0 to 100 vol %, e.g., from 0 to 50 vol %, from 0 to 25 vol %, from 0 to 10 vol %, from 0 to 5 vol %, from 0 to 1 vol %, from 0 to 0.1 vol %, from 0 to 0.01 vol %, from 0 to 0.001 vol %, or from 0 to 0.0001 vol %. Exemplary surfactants include PEGylated phospholipids, TRITONs, e.g., TRITON™ N-101, sorbitan monopalmitate, polysorbate 80, 4-lauryl etherpolyoxyethylene polyoxypropylene copolymer, ethoxylated sorbitan ester, ethoxylated castor oil, a fatty acid, a bile salt, an ethoxylated glyceride, an ethoxylated fatty acid, a sphingolipid, a sorbitan ester, polyglycoside, cetyl alcohol, cocamide, glucosides, maltosides, monolaurin, polyglycol steroidal esters, fatty acid esters, a poloxamer, phospholipids, salts of fatty acids, sterol alcohols and their salts, cationic surfactants (e.g., cetyltrimethylammonium bromide (CTAB), benzalkonium chloride (BAC)), anionic surfactants (e.g., docusates, sulfonates, carboxylates, and alkyl ether phosphates), amphoteric surfactants (e.g., alkyl iminopropionates), and zwitterionic detergents (e.g., sultaines and betaines). Exemplary mixtures of second liquid and surfactant include Polysorbate 80/ethyl acetate (e.g., 0.5:95.5, such as about 0.1:99.9, 1:99, 2.5:97.5, 5:95, 10:90, 20:80), Span 20/ethyl acetate (0.5:95.5, such as about 0.1:99.9, 1:99, 2.5:97.5, 5:95, 10:90, 20:80), Polysorbate 20/ethyl acetate (e.g.,0.5:95.5, such as about 0.1:99.9, 1:99, 2.5:97.5, 5:95, 10:90, 20:80), Polysorbate 80/butyl acetate (e.g.,0.5:95.5, such as about 0.1:99.9, 1:99, 2.5:97.5, 5:95, 10:90, 20:80), Polysorbate 80/isopropanol (e.g.,0.5:95.5, such as about 0.1:99.9, 1:99, 2.5:97.5, 5:95, 10:90, 20:80), and Polysorbate 80/cottonseed oil/ethyl acetate (e.g.,0.5:20:79.5, such as about 0.1:20:79.9, 1:30:69, 2.5:10:87.5, 5:5:90, 10:5:75, 20:20:60).

In some embodiments, the excipients in the droplets are soluble in the second liquid on the timescale of and under the conditions of particle formation. This can lead to leaching of the excipients and changes to the relative ratios of components as particles are formed from the droplets, e.g., the droplets can have a higher excipient to agent ratio than the particles on account of excipient loss (H. C Shum, Biomicrofluidics, 2012, 6 (1), 012808). To counteract this, excipients can be added to the second liquid at appropriate concentrations. This can help to prevent concentration gradients and/or other driving forces that may in some embodiments lead to leaching. In some cases, the second liquid may include other components, such as a carbohydrate, a pH adjusting agent, a salt, a chelator, a mineral, a polymer, a protein stabilizer, an emulsifier, an antiseptic, an amino acid, an antioxidant, a protein, an organic solvent, a paraben, a bactericide, a fungicide, a vitamin, a preservative, or nutrient media. Exemplary carbohydrates include dextran, trehalose, sucrose, agarose, mannitol, lactose, sorbitol, or maltose. The pH adjusting agent may be acetate, citrate, glutamate, glycinate, histidine, lactate, maleate, phosphate, succinate, tartrate, bicarbonate, aluminum hydroxide, phosphoric acid, hydrochloric acid, DL-lactic/glycolic acids, phosphorylethanolamine, tromethamine, imidazole, glyclyglycine, or monosodium glutamate. Exemplary salts include sodium chloride, calcium chloride, potassium chloride, sodium hydroxide, stannous chloride, magnesium sulfate, sodium glucoheptonate, sodium pertechnetate, or guanidine hydrochloride. The chelator can be disodium edetate or ethylenediaminetetraacetic acid. The mineral can be calcium, zinc, or titanium dioxide. Examples of polymers include propyleneglycol, glucose star polymer, silicone polymer, polydimethylsiloxane, polyethylene glycol, carboxymethylcellulose, poly(glycolic acid), poly(lactic-co-glycolic acid), or polylactic acid. Exemplary protein stabilizers include acetyltryptophanate, caprylate, or N-acetyltryptophan. In other embodiments, the protein stabilizer is trehalose, PEG 200, PEG 300, PEG 3350, PEG 8000, PEG 10000, PEG 20000, polyoxamers, polyvinylpyrrolidone, polyacrylic acids, poly (vinyl) polymers, polyesters, polyaldehydes, tert-polymers, polyamino acids, hydroxyethyl starch, N-methyl-2-pyrrolidone, sorbitol, sucrose, or mannitol. The emulsifier can be polysorbate 80, polysorbate 20, sorbitan monooleate, ethanolamine, polyoxyl 35 castor oil, poloxyl 40 hydrogenated castor oil, carbomer 1342, a corn oil-mono-di-triglyceride, a polyoxyethylated oleic glyceride, or a poloxamer. Exemplary antiseptics include phenol, m-cresol, benzyl alcohol, 2-phenyloxyethanol, chlorobutanol, neomycin, benzethonium chloride, gluteraldehyde, or beta-propiolactone. The amino acid may be alanine, aspartic acid, cysteine, isoleucine, glutamic acid, leucine, methionine, phenylalanine, pyrrolysine, serine, selenocysteine, threonine, tryptophan, tyrosine, valine, asparagine, L-arginine, histidine, glycine, glutamine, or a combination thereof. The antioxidant can be glutathione, ascorbic acid, cysteine, or tocopherol. The protein can be protamine, protamine sulfate, or gelatin. The organic solvent can be dimethyl sulfoxide or N-methyl-2-pyrrolidone. The preservative can be methyl hydroxybenzoate, thimerosal, parabens, formaldehyde, or castor oil. The paraben can be a parahydroxybenzoate. The bactericide can be benzalkonium chloride. In certain embodiments, the liquid may further include an analgesic, such as acetaminophen or lidocaine. One of ordinary skill in the art would be able to determine an appropriate amount of the other components in the first or second liquid.

In some embodiments, the droplets of the invention carry an electrical charge, which is useful for preventing agglomeration on the timescale of and under the conditions of particle formation. In some embodiments, the agency of the electric field is such that free charges and/or polar molecules move to the surface of the droplet of the first liquid preferentially on account of Coulombic effects. The former phenomenon, the localization of free charges at the interface between the first liquid and the dielectric medium in which the droplets are formed, produces a layer of surface charge. In some embodiments, such effects are leveraged to influence the structure and/or surface properties of the droplet and/or particle. This includes instances in which the surface charge is used to achieve spherical particle morphologies under conditions in which they would not otherwise be readily accessible, i.e., low transport numbers. In some embodiments, e.g., coordination of the first liquid, which may be polar, near the surface of the droplet facilitates faster removal of the first liquid by the second liquid. It may also mitigate surface-related degradation events among the agents, e.g., the therapeutic or diagnostic agents, and, relative to what is typical in the absence of an electric field, decrease the residual quantity of first liquid in the particle after drying.

In some embodiments, the electric field is such that free charges and/or polar molecules move to the surface of the droplet of the first liquid preferentially on account of Coulombic effects, and one or several components of the droplets crystallize, e.g., therapeutic agents, diagnostic agents, or any of the various excipients that the droplet may comprise. Crystal nucleation of the agent or other droplet component may be controlled to obtain a desired polymorph preferentially (A. Ziabicki, L. Jarecki, Macromolecular Symposia, 1996, 104, 65-87). In some embodiments, crystallization may proceed along a preferential direction, such as along an electric field line.

Droplets of the invention may include one or more shell layers, each of which may or may not be typified by a unique solvent and have a unique composition of solutes, e.g., therapeutic agents, diagnostic agents, or excipients. When the droplets include one or more liquid (shell) layers, particle formation requires drying of at least the outermost layer of the droplet, but may also involve drying of one or more inner layers. In some embodiments, the outermost layer of the core-shell droplet is dried through methods of the invention to produce particles with a solid-shell and non-solid, i.e., liquid or gel-like, inner layers. In some embodiments, all layers of the core-shell droplet are dried through methods of the invention to produce particles with solid layers.

Core-shell particles may also be produced from droplets including a first liquid alone, i.e., in the absence of any shell liquids. In some embodiments, this is achieved by leveraging the proclivity of certain polar molecules and free charges to arrange themselves at the surface of the droplet when it carries net electrical charge and/or when an external electric field is applied. In certain instances, this produces a localization of the therapeutic or diagnostic agents, either towards the core of the droplet or its surface, which can be preserved during desiccation. In some embodiments, this involves a deterministic stratification of various agents (e.g., therapeutic agents, diagnostic agents, excipients) throughout the thickness of the particle. In certain embodiments, non-therapeutic components such as a salt (e.g., NaCl) or a sugar (e.g., sucrose) are driven to the surface, preferentially with the electric field, to form a thin shell around the particle, crystalline or otherwise. This shell may have protective effects or provide a measure of control over pharmacokinetics. In some embodiments, portions of the droplet components may be localized at the particle surface without necessarily forming a uniform or continuous shell.

Methods of Droplet and Particle Handling

Droplets of the invention can be placed in contact with a second liquid in one of several ways. In some embodiments, the droplets are formed within the second liquid, such that they are immediately in contact with one another. In other embodiments, the droplets are formed in a separate medium and placed into contact with the second liquid thereafter, e.g., by dripping or spraying them into or onto the second liquid. This medium can be, e.g., air, an inert gas, vacuum, or a third liquid in which the first liquid is at least partially immiscible on the timescale of and under the conditions of particle formation. In some embodiments, the second liquid is contained in a vessel where the droplets are collected.

The droplets and particles can have different densities, e.g., the solid particles can have a higher density than the liquid droplets. The density of the droplets and the particles may be higher, lower, or substantially the same as the second liquid. In some embodiments (FIG. 1), the second liquid 6 is contained in a vessel 4 and chosen such that its density is between that of the droplets 2 and the solid particles 5. In those embodiments, droplets are dispersed in a medium, e.g., air, inert gas, or vacuum, and collected with the second liquid. The droplets float on the interface between the second liquid 6 and the medium in which they are dispersed, such that the formation of particles is at least partially assisted by evaporation of the first liquid 1 into the medium. In such embodiments the temperature, pressure, and vapor content (of the first liquid) of the medium in which the droplets are dispersed can be regulated to control the evaporation characteristics. The temperature of the medium during evaporation can be from −100 to 300 degrees Celsius, e.g., from −100 to 200° C., from −100 to 150° C., from −100 to 100° C., from −75 to 75° C., from −40 to 40° C., from −30 to 30° C., from −20 to 20° C., from −10 to 10° C., or from −4 to 4° C. The pressure of the medium during evaporation can be from $10^{-6}$ atm to 10 atm, e.g., from $10^{-6}$ atm to 1 atm, from $10^{-5}$ atm to 1 atm, from $10^{-4}$ atm to 1 atm, or from $10^{-3}$ atm to 1 atm. The vapor content (of the first liquid) of the medium during evaporation, relative to the saturation point, can be from 0 to 100%, e.g., from 0 to 50%, from 0 to 25%, from 0 to 10%, from 0 to 5%, from 0 to 2%, from 0 to 1%, from 0 to 0.5%, from 0 to 0.1%, or from 0 to 0.01%. In some of these embodiments, the droplet density can increase during evaporation, leading to the particles 5 that sink into the second liquid 6.

In some embodiments (FIG. 2), the second liquid 3 in the vessel 4 is chosen such that its density is greater than that of the droplets 2 and the particles 5. In those embodiments, the droplets 2 float on the interface, such that removal of the first liquid 1, which is at least partially assisted by evaporation, forms particles 5 which also float.

In some embodiments (FIG. 3), the second liquid 7 in the vessel 4 is chosen such that its density is less than or equal to that of the droplets 2. In those embodiments, the droplets 2 do not necessarily float, and drying may occur through dispersal of the first liquid 1 in the second liquid 7 over time.

Figure 6:
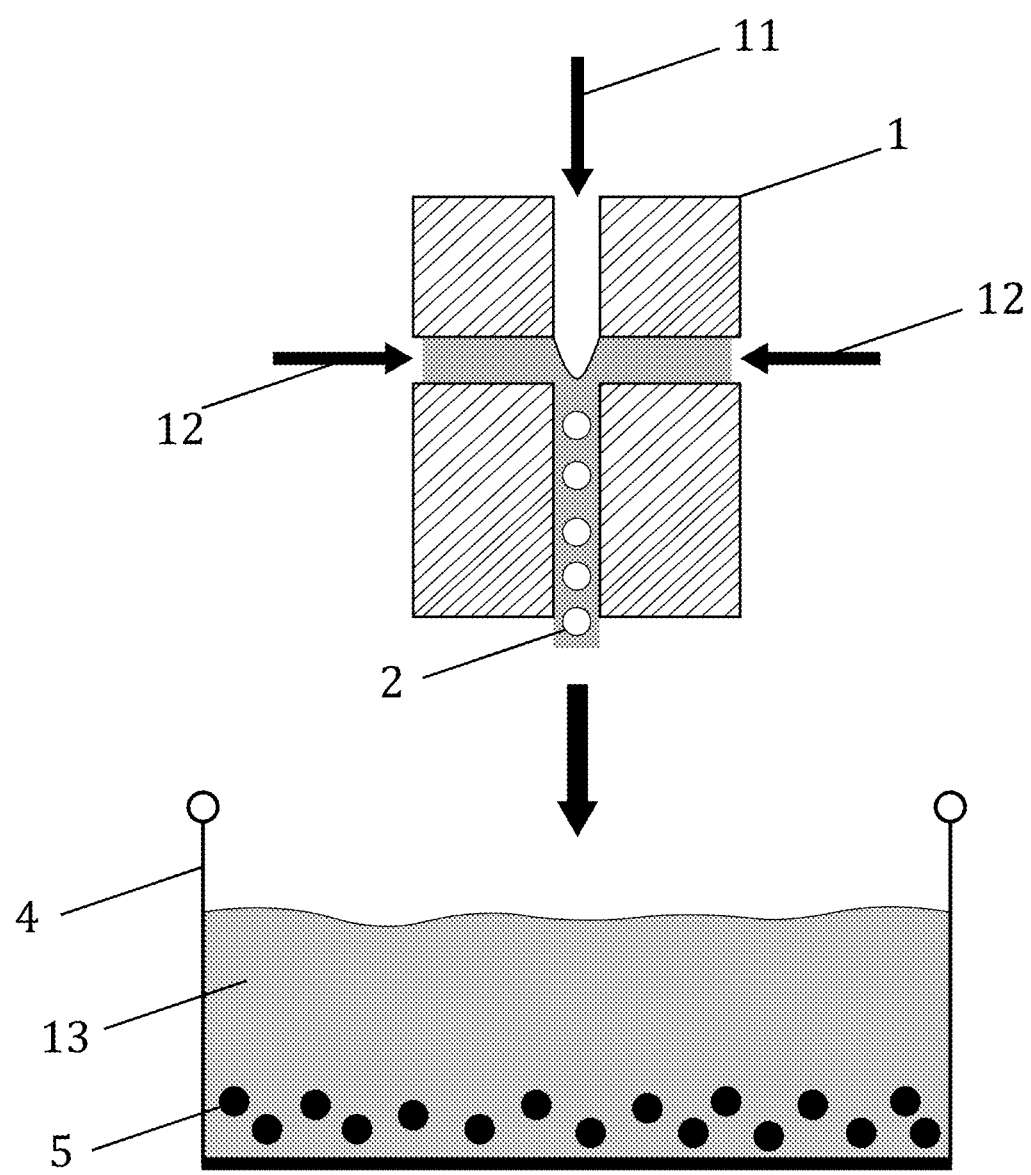
FIG. 6 is a scheme showing a microfluidic droplet source 1 that produces droplets 2. The first liquid 11 is co-flowed with an at least partially immiscible liquid 12 to form the droplets 2 that are collected by a vessel 4 containing the second liquid 13. The droplets 2 are dried to form particles 5 that may float on the second liquid 13, depending on the densities of the liquids. In some embodiments, the liquids 12 and 13 are the same liquids, while, in other embodiments, they are different.
Figure 7:
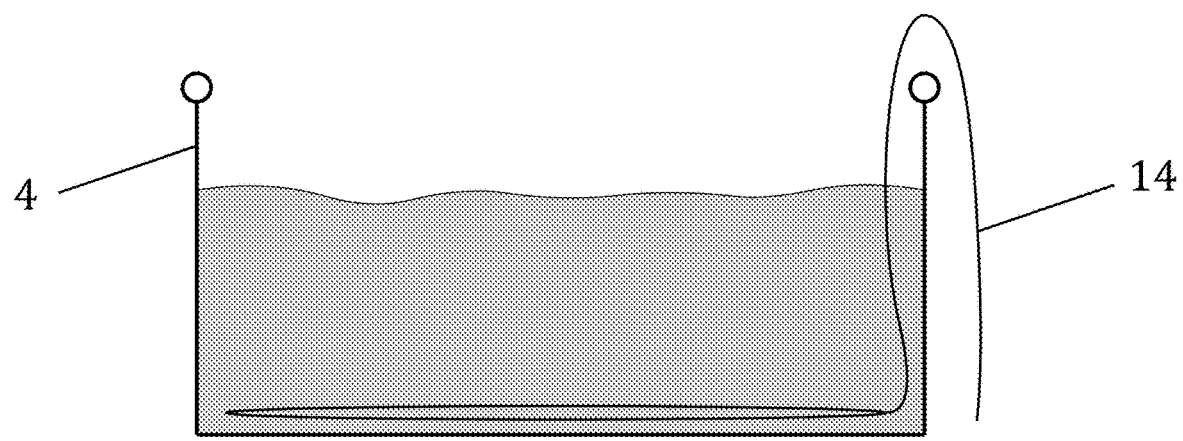
Figure 8:
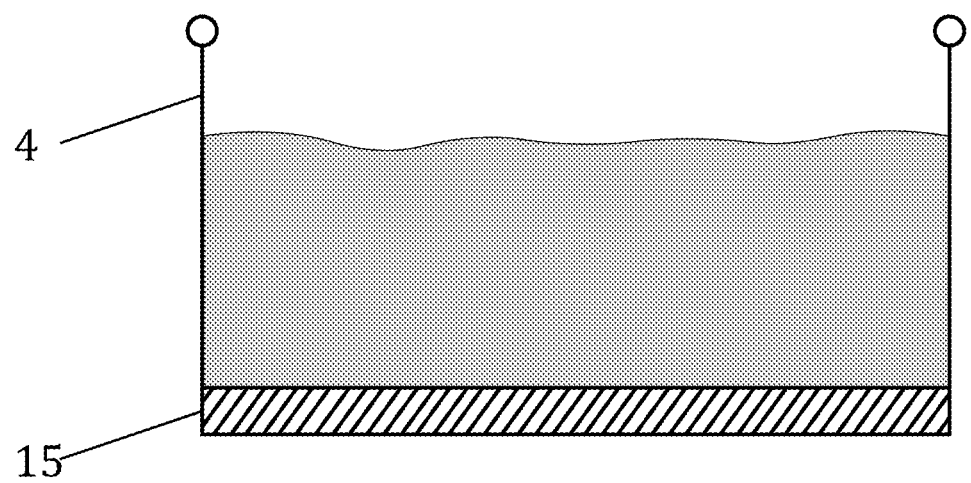
Figure 9A:
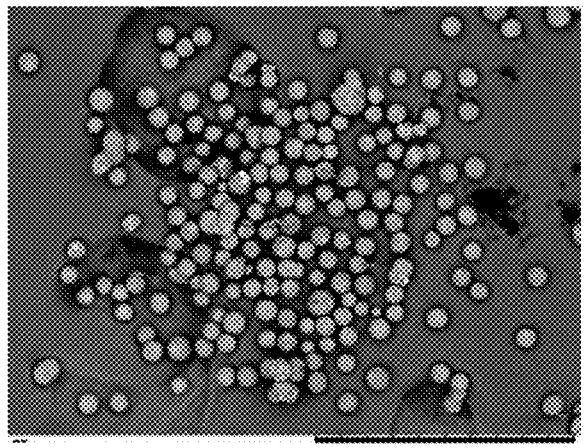
Figure 9B:
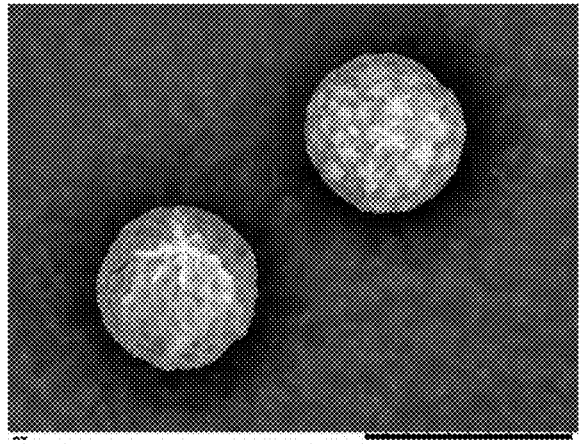
Figure 9C:
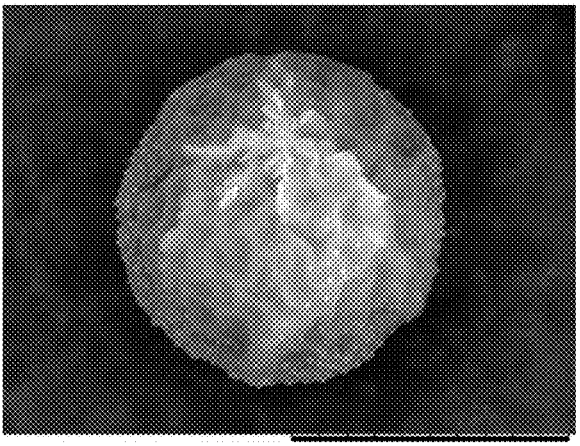
Figure 9D:
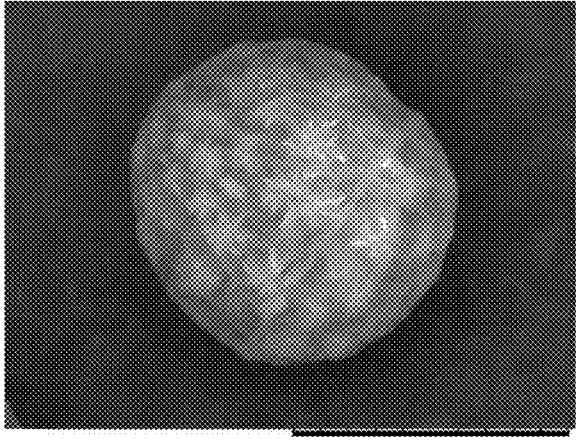
Figure 10:
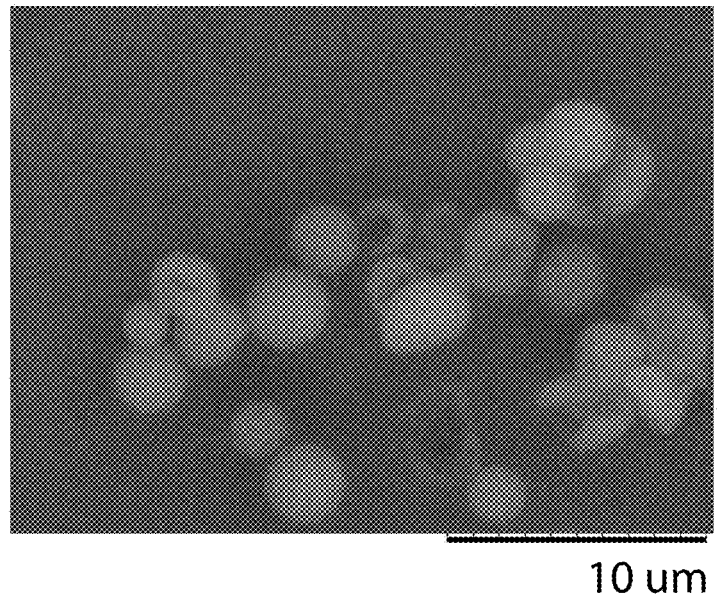
Figure 11A:
Figure 11B:
Figure 12A:
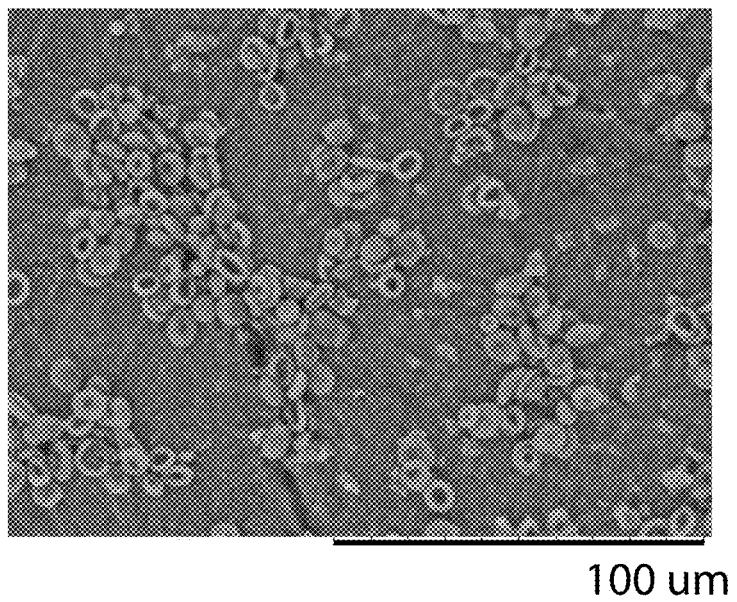
Figure 12B:
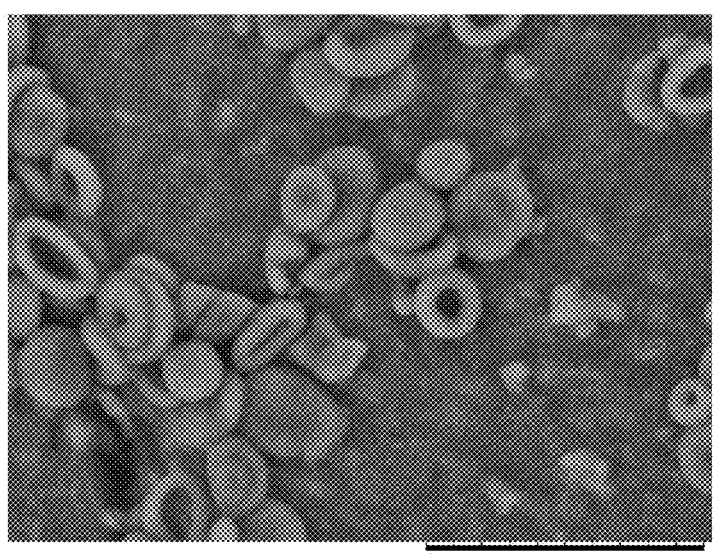

In some embodiments, droplets are formed using a microfluidic device (FIG. 6). In some such embodiments, microfluidic source 1 produces droplets 2, wherein the first liquid 11 is co-flowed with an at an least partially immiscible liquid 12, i.e., a third liquid, to form droplets 2. The droplets 2 can be collected in a vessel 4 containing a second liquid 13, in which they dry to form particles 5. In some embodiments, the liquids 12 and 13 are different but miscible. In some embodiments, the first liquid is co-flowed directly with the second liquid, such that an intermediate liquid 12 is obviated. Droplets may be formed by the traditional method, whereby flow in the microfluidic system remains Stokesian, typified by a low Reynolds number, or through inertial microfluidic technologies (J. Zhang et al. Lab Chip. 2016, 16, 10-34).

In some embodiments, an electric field and/or magnetic field is used to guide or steer charged and/or magnetic droplets into and through a second liquid. Such techniques are particularly useful when spraying droplets into a medium, e.g., air, and collecting them in a vessel of the second liquid. In some embodiments, the electric and/or magnetic field is also useful for overcoming buoyancy and/or surface tension effects. The forces associated with the electric and/or magnetic fields are such that the droplets can be driven into the second liquid in instances where the surface tension and/or density of the second liquid would otherwise make it difficult.

In some embodiments, the droplets are charged. In some such embodiments, the charge on the droplets or particles is all or partially dissipated before, during, or after desiccation by means of, e.g., contacting the droplets or particles with an electrode. In other embodiments, the charge on the droplets or particles is intentionally preserved, either completely or in part, by preventing direct contact between an electrode and the droplets or particles.

In some embodiments, the vessel includes an electrode. Exemplary electrodes include a wire (FIG. 7) and a conductive surface of the vessel (FIG. 8).

In some embodiments, a surfactant is added to the second liquid to decrease the surface tension. Such effects are useful for facilitating entry of the droplets into the second liquid when the droplets are first dispersed in a medium and then collected with a vessel of the second liquid.

The use of gentle stirring or a motion of the second liquid, e.g., such as in continuous stirred tank reactor or a linear flow channel, may also be useful during drying to, e.g., reduce droplet or particle aggregation. The second liquid can also include or be in contact with a drying substance (desiccant) to absorb the first liquid or otherwise sequester it, e.g., by reaction. Such substances are useful for ensuring a uniform, steady-state degree of saturation of the first liquid in the second liquid during drying. Exemplary desiccants include celite, molecular sieves, phosphorous pentoxide, magnesium sulfate, silica, calcium chloride, activated charcoal, and potassium carbonate, among others.

In some embodiments, the particles are removed from the second liquid via centrifugation, sieving, filtration, magnetic collection, solvent exchange, or decanting. In some embodiments, the particles are removed from the second liquid through a solvent exchange washing procedure. After removal of the bulk of the second liquid (e.g., after centrifugation and supernatant decanting), another liquid may be added which is volatile, miscible with the second liquid, and in which the particles are not soluble on the timescale and under the conditions of washing. In such a manner the second liquid can be replaced with a volatile washing liquid that is easier to remove. Additional cycles of concentration, supernatant removal, and backfilling with the washing liquid may lead to substantial reduction of the content of the second liquid. The washing liquid may be subsequently evaporated, e.g., by application of heat and/or vacuum, or removed via lyophilization. In some embodiments, the washing liquid is an organic solvent, such as acetic acid, acetone, acetonitrile, alkanes (e.g., hexanes, heptane), amyl acetate, butanol, butyl acetate, chlorobenzene, chloroform, cumene, cyclohexane, 1,2-dichloroethene, dichloromethane, diethyl ether, dimethoxyethane, dimethylacetamide, dimethylformamide, dimethyl sulfoxide, 1,4-dioxane, ethanol, 2-ethoxyethanol, ethyl acetate, ethyl nitrate, ethyleneglycol, formic acid, hydrazine, isopropanol, methanol, methyl acetate, 2-methyl-1-butanol, 2-methyl-1-propanol, methylbutyl ketone, methylcyclohexane, methylethyl ketone, methylpyrrolidone, methyl tert-butyl ether, nitromethane, propanol, propyl acetate, sulfolane, sarcosine, tetrahydrofuran, tetralin, toluene, 1,1,2-tricholoroethane, triethylamine, urea, xylene, and any combinations thereof. In some embodiments the washing liquid is a supercritical fluid, e.g., supercritical $CO_2$, a cryogenic fluid, e.g., liquid nitrogen, or a mixture of one of these liquids and an organic solvent.

The particles can be subjected to one or more secondary desiccation steps after separation from the second liquid.

Such steps can be utilized to remove washing liquid, as stated previously, and/or to modulate residual quantities of the first liquid in the particles. Exemplary methods of secondary desiccation include vacuum drying with or without application of heat, lyophilization, fluidized bed drying, and slurry spray drying.

Particle

The particles described herein are discrete, roughly spheroidal, and of controlled dispersity with a characteristic size from sub-micrometers to tens of micrometers, in contrast to, e.g., a porous monolithic "cake", such as is typically produced during conventional lyophilization. This morphology typically allows for a flowable powder (as described by low Hausner ratios) without post-processing.

The particles may include both a core and a shell. In some embodiments, the particles include a core but not a shell. The core is a gel core or dry solid-state core when no shell is present but may exist in the liquid state when the particles include a gel shell or dry solid-state shell. The morphology of the particles is approximately spherical, mushroom-like, or raisin-like, among potentially other morphologies, depending on the conditions of particle formation. In some embodiments the particle surfaces may have wrinkles or crenellations. When particles with core-shell architectures are employed, the individual layers may include the same or different agents, e.g., therapeutic or diagnostic agents, or no agents at all. Furthermore, layers with the same agents, e.g., therapeutic or diagnostic agents, may or may not include the agents in the same concentration.

The particles may include one or more agents, e.g., therapeutic or diagnostic agents. The particles can have diameters from 0.1 to 1000 µm, e.g., 0.1 to 90 µm, 90 to 230 µm, or 0.1 to 1 µm. The particles can have a size dispersity from 0 to 0.9, e.g., from 0 to 0.7, from 0 to 0.5, or from 0 to 0.2. Methods of measuring the particle size and distribution include imaging flow cytometry and image analysis of scanning electron micrographs of the particles in which an average spherical radius or diameter is calculated on the basis of the cross-sectional areas of the particles projected onto the plane of the image.

Cohesive forces (e.g., interfacial tension) on the droplet surface in the second liquid may pull the droplets into a spherical shape which is maintained during the course of drying. Sphericity of the particles may range from 0.1 to 1, e.g., be at least 0.2, 0.4, 0.6, or 0.8. This process can result in uniform particles with high sphericity (>0.9) and roundness. Methods of measuring particle sphericity include image analysis of scanning electron micrographs of the particles in which the average roundness is calculated on the basis of the cross-sectional shapes of the particles projected onto the plane of the image. Such roundness factors can be extended to identify the corresponding sphericity.

In some embodiments, the particles exhibit a skeletal density from about 1 to 6 g/cm$^3$, e.g., from about 1 to 5 g/cm$^3$, from about 1 to 3 g/cm$^3$, from about 1 to 2 g/cm$^3$, from about 1 to 1.5 g/cm$^3$, or from about 1.1 to 1.4 g/cm$^3$. Exemplary methods of density measurements include gas displacement pycnometry.

In some embodiments, residual quantities of the first liquid in the particles after desiccation are from 0 to 10% by weight, e.g., from 0 to 5% by weight, from 0 to 3% by weight, from 0 to 1% by weight, 0.01 to 5% by weight, from 0.01 to 3% by weight, or from 0.01 to 1% by weight. Exemplary methods of measuring residual solvent content include Karl Fischer titration, headspace gas chromatography mass spectrometry, and various weight-loss methods.

In some embodiments, residual quantities of the second liquid in the particles after desiccation are from 0 to 10% by weight, e.g., from 0 to 5% by weight, from 0 to 3% by weight, from 0 to 1% by weight, 0.01 to 5% by weight, from 0.01 to 3% by weight, or from 0.01 to 1% by weight. Exemplary methods of measuring residual solvent content include Karl Fischer titration, headspace gas chromatography mass spectrometry, and various weight-loss methods.

In some embodiments, residual quantities of one or more shell liquids in the particles after desiccation are from 0 to 10% by weight, e.g., from 0 to 5% by weight, from 0 to 3% by weight, or from 0 to 1% by weight. Exemplary methods of measuring residual solvent content include Karl Fischer titration, headspace gas chromatography mass spectrometry, and various weight-loss methods.

In some embodiments, the particles may exhibit a porosity from about 0 to 50%, e.g., from about 0 to 10%, from about 0 to 5%, from about 0 to 1%, from about 0 to 0.5%, from about 0 to 0.1%, or from about 0 to 0.01%. Exemplary pore size measurements include scanning electron microscopy (SEM), transmission electron microscopy (TEM), and confocal laser scanning microscopy analysis. The specific surface area of porous micro- and nanospheres may also be investigated by nitrogen adsorption/desorption analysis and a Brunauer-Emmett-Teller adsorption model. In embodiments where the pore sizes are sufficiently large, mercury-intrusion porosimetry may be employed.

In some embodiments, the particles have a residual net electrical charge of either polarity, i.e., net positive or net negative charge. In terms of magnitude, the particles may have from 0 to 10 billion charges, e.g., from 0 to 100 million charges, from 0 to 1 million charges, from 0 to 0.01 million charges, or from 0 to 100 charges. The magnitude of a charge is defined as the magnitude of charge carried by an electron, i.e., the elementary charge, $1.6 \times 10^{-19}$ Coulombs. Exemplary methods of measuring particle charge include those involving the analysis of particle motion in response to an externally applied electric field, e.g., electrical mobility. In some cases, this is done while particles are suspended in an insulating liquid such as an oil.

In certain embodiments, the therapeutic or diagnostic agents have a zeta potential from about −90 to 90 mV; e.g., from about −60 to 60 mV, from about −40 to 40 mV, from about −20 to 20 mV, or from about −5 to 5 mV. Exemplary methods of measuring zeta potential include reconstituting the therapeutic or diagnostic agents by dissolving the particles in water and analyzing the solution by electrophoretic light scattering. This is similar to a dynamic light scattering (DLS) measurement which is performed in the presence of a positive or negative electric field.

In some embodiments, insoluble particulate matter with characteristic sizes greater than or equal to 1 µm persist upon reconstitution of the particles of the invention into a liquid pharmaceutical composition. These are sometimes referred to as Subvisible Particles (SvPs). SvPs are present in quantities from about 0 to 100,000,000 per mL, e.g., from 0 to 10,000,000 per mL, from 0 to 1,000,000 per mL, from 0 to 500,000 per mL, from 0 to 100,000 per mL, from 0 to 50,000 per mL, from 0 to 10,000 per mL, from 0 to 6,000 per mL, from 0 to 1,000 per mL, from 0 to 600 per mL, from 0 to 250 per mL, from 0 to 100 per mL, from 0 to 60 per mL, or from 0 to 10 per mL. In some embodiments, the count of particles with characteristic size greater than or equal to 10 µm is from 0 to 6,000 per mL, e.g., from 0 to 1,000 per mL, from 0 to 100 per mL, from 0 to 10 per mL, from 0 to 5 per mL, from 0 to 3 per mL, or from 0 to 1 per mL. In some embodiments, the count of particles with characteristic size greater than or equal to 25 µm is from 0 to 600 per mL, e.g., from 0 to 100 per mL, from 0 to 10 per mL, from 0 to 3 per mL, from 0 to 1 per mL, from 0 to 0.5 per mL, or from 0 to 0.1 per mL. Exemplary methods of measuring SVPs include analysis of the therapeutic or diagnostic agent with a Coulter Counter, HIAC Royco, or micro-flow imaging system after reconstitution and dilution of the therapeutic or diagnostic agent to a standard concentration, e.g., about 100 mg/mL or about 1 mg/mL.

In some embodiments, the particles include a loading of therapeutic or diagnostic agents from 1 to 100 wt %, e.g., from 50 to 100 wt %, from 75 to 100 wt %, from 90 to 100 wt %, from 95 to 100 wt %, from 99 to 100 wt %, or from 99.9 to 100 wt %. At these loadings the therapeutic or diagnostic agents retain from 0.5 to 1.0 activity during particle formation, e.g., from 0.75 to 1.0 activity, from 0.9 to 1.0 activity, from 0.95 to 1.0 activity, from 0.99 to 1.0 activity, or from 0.999 to 1.0 activity. This includes the activity retained through primary desiccation (i.e., desiccation utilizing a second liquid) and, in some cases, secondary desiccation.

In some cases, the method may further include suspending the particles in a pharmaceutically acceptable medium, e.g., reconstitution of the dried particles. In some embodiments, the dissolution or reconstitution of the particles provides less than a 10% increase in aggregates of the diagnostic or therapeutic agent, e.g., a protein, (e.g., less than 8%, less than 5%, less than 4%, less than 3%, less than 1%, less than 0.5%, or less than 0.1%) as compared to the therapeutic or diagnostic agent in the first liquid prior to processing. Exemplary methods of measuring aggregates include size exclusion high-performance liquid chromatography (SEC-HPLC), where the aggregate population is quantified by dividing the area under the peak corresponding to the aggregate population by the cumulative area contained beneath all peaks in the sample spectrum. Changes in aggregate percentage between two samples, e.g., Sample A and Sample B, are computed as the numerical difference in the respective aggregate percentages, i.e., by subtracting the aggregate percentage of Sample B from the aggregate percentage of Sample A, or vice versa.

In some embodiments, the dissolution or reconstitution of the particles provides less than a 10% increase in fragments of the diagnostic or therapeutic agent, e.g., a protein, (e.g., less than 8%, less than 5%, less than 4%, less than 3%, less than 1%, less than 0.5%, or less than 0.1%) as compared to the therapeutic or diagnostic agent in the first liquid prior to processing. Exemplary methods of measuring fragments include size exclusion high-performance liquid chromatography (SEC-HPLC), where the fragment population is quantified by dividing the area under the peak corresponding to the fragment population by the cumulative area contained beneath all peaks in the sample spectrum. Changes in fragment percentage between two samples, e.g., Sample A and Sample B, are computed as the numerical difference in the respective fragment percentages, i.e., by subtracting the fragment percentage of Sample B from the fragment percentage of Sample A, or vice versa.

In some embodiments, the process of particle formation provides less than a 50% change in charge variants in the population of a diagnostic or therapeutic agent, e.g., an antibody or an antibody fragment, (e.g., less than 40, 30, 20, 10, 8, 5, 4, 3, or 1%) as compared to the therapeutic or diagnostic agent prior to particle formation. Charge variants may be acidic, basic, or neutral, and the variation may be caused post-translation modifications at terminal amino acids, such as asparagine deamidation or lysine glycation. For example, charge variants include the loss of a positive charge by the loss of a C-terminal lysine residue, covalent bonding of the amine portions of two lysine residues by reducing sugars, or the conversion of an N-terminal amine to a neutral amide by the cyclization of N-terminal glutamines. Negative charges on proteins, e.g., antibodies, can appear by the conversion of asparagine residues to aspartic acid and/or isoaspartic residues via a deamidation reaction.

Exemplary methods of measuring charge variants include cation exchange chromatography (CIEX), where the variants are quantified by dividing the area under the peak corresponding to the variant, e.g., acidic, basic, or neutral population by the cumulative area contained beneath all peaks in the sample spectrum. Changes in charge variant population percentage between two samples, e.g., Sample A and Sample B, are computed as the numerical difference in the respective population variant percentages, i.e., by subtracting the specific variant, e.g., acidic, percentage of Sample B from the specific variant, e.g., acidic, percentage of Sample A, or vice versa. This analysis may be extended similarly for all variants within a population.

In some embodiments, the particles are flowable. The Hausner ratio may be from 1.0 to greater than 3.0, e.g., from 1.0 to 3.0, from 1.0 to 2.0, from 1.0 to 1.70 (e.g., very poor), from 1.0 to 1.59, from 1.0 to 1.35, from 1.0 to 1.25, or from 1.0 to 1.11 (e.g., excellent). Exemplary methods of measuring the flowability of a powder include the tapped density method (Carr R. L. Chem. Eng., 1965; 72:163-168). Bulk density may first be obtained by adding a known mass of powder to a graduated cylinder. The density can be calculated as mass/volume. The same sample may then be mechanically tapped until further volume change is not observed. The tapped density can then be calculated as mass divided by the final volume of the powder. A comparison of tapped and bulk density may be used to index the ability of the powder to flow. In particular, the Hausner ratio (unsettled apparent volume or bulk volume, $V_0$, divided by the final tapped volume, $V_f$) is a measure of the product's ability to settle and permits an assessment of the relative importance of interparticulate interactions. These interactions are less significant in free flowing powders. The bulk and tapped densities for such free flowing powders are close in value, such that the Hausner ratio is close to 1.0.

In some embodiments, the particles have one or more of the following characteristics: a size from 1 to 50 µm; a solid core; a gel or solid shell; a density from 1 to 1.5 g/cm$^3$; a residual solvent content from 0 to 5 wt %; a porosity from 0 to 10%; a net electrical charge of either polarity, i.e., positive or negative charge, from 0 to 1 million charges; therapeutic or diagnostic components with a zeta potential from −60 to 60 mV; SvPs from 0 to 1,000,000 per mL upon reconstitution; a therapeutic or diagnostic agent loading from 50 to 100 wt % in which the activity of the therapeutic or diagnostic agents is from 0.9 to 1.0 upon reconstitution; less than 10% aggregates upon reconstitution; less than 10% fragments upon reconstitution; and/or a Hausner ratio between 1.0 and 1.35, or between 1.0 and 1.11.

In some embodiments, the storage stability of the therapeutic or diagnostic agent in the particles is improved with respect to the storage stability of a first liquid of the therapeutic or diagnostic agent. In some embodiments, storage conditions are defined by time (e.g., more than 2 years, more than 1 year, more than 6 months, more than 3 months, more than 1 month, or more than 1 week) and temperature (e.g., −80° C. to 100° C., −80° C. to 60° C., −20° C. to 60° C., 4 to 60° C.), among potentially other variables. In some embodiments, the storage time is 3 days, 7 days, 30 days, 90 days, 180 days, 1 year, or 2 years. In some embodiments, this temperature is −80° C., −40° C., −20° C., 4° C., 25° C., 40° C., or 40-60° C. In some embodiments, after dissolution or reconstitution of the particles following storage, SvPs are present in quantities from about 0 to 100,000,000 per mL, e.g., from 0 to 10,000,000 per mL, from 0 to 1,000,000 per mL, from 0 to 500,000 per mL, from 0 to 100,000 per mL, from 0 to 50,000 per mL, from 0 to 10,000 per mL, from 0 to 6,000 per mL, from 0 to 1,000 per mL, from 0 to 600 per mL, from 0 to 250 per mL, from 0 to 100 per mL, from 0 to 60 per mL, or from 0 to 10 per mL. In some embodiments, the count of particles with characteristic size greater than or equal to 10 µm is from 0 to 6,000 per mL, e.g., from 0 to 1,000 per mL, from 0 to 100 per mL, from 0 to 10 per mL, from 0 to 5 per mL, from 0 to 3 per mL, or from 0 to 1 per mL. In some embodiments, the count of particles with characteristic size greater than or equal to 25 µm is from 0 to 600 per mL, e.g., from 0 to 100 per mL, from 0 to 10 per mL, from 0 to 3 per mL, from 0 to 1 per mL, from 0 to 0.5 per mL, or from 0 to 0.1 per mL. In some embodiments, after dissolution or reconstitution of the particles following storage, the therapeutic or diagnostic agent retains from 0.5 to 1.0 activity, e.g., from 0.75 to 1.0 activity, from 0.9 to 1.0 activity, from 0.95 to 1.0 activity, from 0.99 to 1.0 activity, or from 0.999 to 1.0 activity. In some embodiments, dissolution or reconstitution of the particles following storage provides less than a 10% increase in aggregates of the diagnostic or therapeutic agent, e.g., a protein, (e.g., less than 8%, less than 5%, less than 4%, less than 3%, less than 1%, less than 0.5%, or less than 0.1%) as compared to the therapeutic or diagnostic agent in the first liquid prior to processing. In some embodiments, the dissolution or reconstitution of the particles after storage provides less than a 10% increase in fragments of the diagnostic or therapeutic agent, e.g., a protein, (e.g., less than 8%, less than 5%, less than 4%, less than 3%, less than 1%, less than 0.5%, or less than 0.1%) as compared to the therapeutic or diagnostic agent in the first liquid prior to processing. In some embodiments, the dissolution or reconstitution of the particles following storage provides less than a 50% change in charge variants in the population of a diagnostic or therapeutic agent, e.g., an antibody or an antibody fragment, (e.g., less than 40, 30, 20, 10, 8, 5, 4, 3, or 1%) as compared to the therapeutic or diagnostic agent prior to particle formation.

Particle Core

The core of each particle typically includes one or more therapeutic or diagnostic agents. The core is a solid-state dry core or gel when no shell is present but may exist in the liquid state when the particle includes a gel shell or solid-state dry shell. When a shell is present, the shell may include the therapeutic or diagnostic agent, while the core may not.

Particle Shell

Generally, any excipient is suitable as a shell material. Exemplary excipients include, but are not limited to, sugars, salts, and amino acids. Therapeutic agents, diagnostic agents, and biocompatible polymers may also be used to form the shell. This includes small molecule drugs. Non-limiting examples of hydrophilic biocompatible polymers include poly(vinyl alcohol), poly(acrylic acid), poly(acrylamide), poly(ethylene oxide), or co-polymers or combinations of any two or more of them. Hydrophilic polymers may be modified to adjust their characteristics. The shell component may alternatively or additionally include one or more biocompatible hydrophobic polymers. Hydrophobic polymers may be modified to adjust their characteristics. Non-limiting examples of hydrophobic polymers include polycaprolactam, poly(lactic acid), poly(glycolic acid), polycaprolactone, PLGA or co-polymers, or combinations of any two or more of them. In some embodiments, a PLGA (50:50) polymer is used as a shell to encapsulate a therapeutic, e.g., an antibody or an antibody fragment, in an amount just below its solubility limit. The polymer also may be prepared as a function of PLGA at various lactic acid-glycolic acid ratios, as well as be co-polymer with other polymers, e.g., chitosan, cellulose, etc.

The thickness of the particle shell may range from 0 to 90% of the diameter of the particle in some embodiments. The shell does not have to be uniform of fully formed for encapsulation. In some embodiments the interface between the shell and the core is partially blended, such that a clear line of demarcation does not exist. Moreover, one or more therapeutic or diagnostic agents, as described herein, can be included in the particle shell. The therapeutic or diagnostic agents can be the same or different as those in the core. The concentration of the therapeutic or diagnostic agent in the shell may be in the range 0.0001 to 2000 mg/mL (or crystalline density of the therapeutic or diagnostic agent, if higher).

Core-Shell Ratio

For those embodiments in which the particle includes a shell, a core-shell volume ratio between 1:99 vol % and 99:1% are expected to be most useful, e.g., about 10:90 vol % or about 90:10 vol % or about 95:5 vol %. Complete coverage is not always required for sufficient encapsulation. In certain circumstances, e.g., for highly concentrated cores, thick shells can be beneficial. The core-shell ratio may be useful in the modulation of the release kinetics of the therapeutic or diagnostic agent or agents. In certain embodiments, it is advantageous to have a polydisperse system, e.g., for lowering the viscosity of a pharmaceutical suspension formulation comprising the particles. In this instance a variety of core-shell ratios may be of interest.

Therapeutics and Diagnostics

Exemplary therapeutic or diagnostic agents nucleic acids, oligonucleotides, antibodies or fragment thereof, amino acids, peptides, proteins, cells, bacteria, gene therapeutics, genome engineering therapeutics, epigenome engineering therapeutics, carbohydrates, chemical drugs, contrast agents, magnetic particles, polymer beads, metal nanoparticles, metal microparticles, quantum dots, antioxidants, antibiotic agents, hormones, nucleoproteins, polysaccharides, glycoproteins, lipoproteins, steroids, analgesics, local anesthetics, anti-inflammatory agents, anti-microbial agents, chemotherapeutic agents, exosomes, outer membrane vesicles, vaccines, viruses, bacteriophages, adjuvants, vitamins, minerals, organelles, and any combination thereof. Table 1 provides a list of therapeutic and diagnostic agents and the typical concentration range for the general class of compound in a pharmaceutical composition. Therapeutic and diagnostic agents may have a molecular weight of 20 to 200 kDa, e.g., 40 to 150 kDa, or 50 to 100 kDa. The concentration of the therapeutic or diagnostic agent in the droplet is typically at least 0.5 mg/mL, e.g., at least 1 mg/mL, at least 5 mg/mL, at least 50 mg/mL, at least 100 mg/mL or at least 500 mg/mL. The first therapeutic or diagnostic agent in the droplets may have 0.5 to 1.0 activity per unit, 0.75 to 1.0 activity per unit, or 0.9 to 1.0 activity per unit. Activity is measured relative to the same therapeutic or diagnostic agent prior to being dried.

TABLE 1

Various therapeutic and diagnostic agents in the droplets and their typical concentrations.

| Therapeutic/diagnostic agent | Concentration range (mg/mL) |
| --- | --- |
| proteins | 20-1500 (e.g., 20-600) (or crystalline density, if higher) |
| peptides | 20-1500 (e.g., 20-600) (or crystalline density, if higher) |
| chemical drugs | 0.0001-2000 (e.g., 0.0001-1000) (or crystalline density, if higher) |
| magnetic particles | 0.001-5400 (e.g., 0.001-500) (iron oxide density) |
| carbohydrates | 0.001-400 |
| nucleic acids | 0.001-100 |

In some embodiments, the therapeutic is an immunotherapeutic. In some embodiments, the immunotherapeutic is a PD-1 inhibitor such as a PD-1 antibody, a PD-L1 inhibitor such as a PD-L1 antibody, a CTLA-4 inhibitor such as a CTLA-4 antibody, a CSF-1R inhibitor, an IDO inhibitor, an Al adenosine inhibitor, an A2A adenosine inhibitor, an A2B adenosine inhibitor, an A3A adenosine inhibitor, an arginase inhibitor, or an HDAC inhibitor. In some embodiments, the immunotherapeutic is a PD-1 inhibitor (e.g., nivolumab, pembrolizumab, pidilizumab, BMS 936559, and MPDL328OA). In some embodiments, the immunotherapy is a PD-L1 inhibitor (e.g., atezolizumab and MEDI4736). In some embodiments, the immunotherapeutic is a CTLA-4 inhibitor (e.g., ipilimumab). In some embodiments, the immunotherapeutic is a CSF-1R inhibitor (e.g., pexidartinib and AZD6495). In some embodiments, the immunotherapeutic is an IDO inhibitor (e.g., norharmane, rosmarinic acid, and alpha-methyl-tryptophan). In some embodiments, the immunotherapeutic is an Al adenosine inhibitor (e.g., 8-cyclopentyl-1,3-dimethylxanthine, 8-cyclopentyl-1,3-dipropylxanthine, 8-phenyl-1,3-dipropylxanthine, bamifylline, BG-9719, BG-9928, FK-453, FK-838, rolofylline, or N-0861). In some embodiments, the immunotherapeutic is an A2A adenosine inhibitor (e.g., ATL-4444, istradefylline, MSX-3, preladenant, SCH-58261, SCH-412,348, SCH-442,416, ST-1535, VER-6623, VER-6947, VER-7835, viadenant, or ZM-241,385). In some embodiments, the immunotherapeutic is an A2B adenosine inhibitor (e.g., ATL-801, CVT-6883, MRS-1706, MRS-1754, OSIP-339,391, PSB-603, PSB-0788, or PSB-1115). In some embodiments, the immunotherapeutic is an A3A adenosine inhibitor (e.g., KF-26777, MRS-545, MRS-1191, MRS-1220, MRS-1334, MRS-1523, MRS-3777, MRE-3005-F20, MRE-3008-F20, PSB-11, OT-7999, VUF-5574, and SSR161421). In some embodiments, the immunotherapeutic is an arginase inhibitor (e.g., an arginase antibody, (2s)-(+)-amino-5-iodoacetamidopentanoic acid, NG-hydroxy-L-arginine, (2S)-(+)-amino-6-iodoacetamidohexanoic acid, or (R)-2-amino-6-borono-2-(2-(piperidin-1-yl)ethyl)hexanoic acid. In some embodiments, the immunotherapeutic is an HDAC inhibitor (e.g., valproic acid, SAHA, or romidepsin). In some embodiments, the immunotherapeutic is a toll-like receptor activator. In some embodiments, the immunotherapy is a RIG-I-like receptor activator. In some cases, the immunotherapeutic is a stimulator of interferon genes (STING) pathway avtivator. In some embodiments, the immunotherapeutic is an Interleukin-1 receptor agonist, e.g., an IL-R1 antagonist. In some embodiments, the immunotherapeutic is a PTEN inhibitor, e.g., a bisperoxovanadium compound. In some embodiments, the immunotherapeutic is a tumor necrosis factor receptor (TNFR), e.g., TNFR-1 or TNFR-2 inhibitor. In some embodiments, the immunotherapeutic is a Lymphocyte-activation gene 3 (LAG-3) inhibitor, e.g., GSK2831781.

In some embodiments, the therapeutic is ledipasvir/sofosbuvir, insulin glargine, lenalidomide, pneumococcal 13-valent conjugate vaccine, fluticasone/salmeterol, elvitegravir/cobicistat/emtricitabine/tenofovir alafenamide, emtricitabine, rilpivirine and tenofovir alafenamide, emtricitabine/tenofovir alafenamide, grazoprevir/elbasvir, coagulation factor VIIa recombinant, epoetin alfa, Aflibercept or etanercept.

In some embodiments, the therapeutic or diagnostic agent is Abatacept, AbobotulinumtoxinA, Agalsidase beta, Albiglutide, Aldesleukin, Alglucosidase alfa, Alteplase (cathflo activase), Anakinra, Asfotase alfa, Asparaginase, Asparaginase erwinia chrysanthemi, Becaplermin, Belatacept, Collagenase, Collagenase clostridium histolyticum, Darbepoetin alfa, Denileukin diftitox, Dornase alfa, Dulaglutide, Ecallantide, Elosulfase alfa, Etanercept-szzs, Filgrastim, Filgrastim-sndz, Galsulfase, Glucarpidase, Idursulfase, IncobotulinumtoxinA, Interferon alfa-2b, Interferon alfa-n3, Interferon beta-la, Interferon beta-1b, Interferon gamma-1b, Laronidase, Methoxy polyethylene glycol-epoetin beta, Metreleptin, Ocriplasmin, OnabotulinumtoxinA, Oprelvekin, Palifermin, Parathyroid hormone, Pegaspargase, Pegfilgrastim, Peginterferon alfa-2a, Peginterferon alfa-2a co-packaged with ribavirin, Peginterferon alfa-2b, Peginterferon beta-1a, Pegloticase, Rasburicase, Reteplase, Rilonacept, RimabotulinumtoxinB, Romiplostim, Sargramostim, Sebelipase alfa, Tbo-filgrastim, Tenecteplase, or Ziv-aflibercept.

In some embodiments, the diagnostic agent is tuberculin purified protein derivative, hyrotropin alpha, secretin, soluble transferrin receptor, troponin, B-type natriuretic peptide, iobenguane I 123, florbetapir F 18, perflutren, gadoterate meglumine, florbetaben F 18, flutemetamol F 18, gadoterate meglumine, isosulfan blue, regadenoson, technetium Tc 99m tilmanocept, florbetaben F 18, perflutren, regadenoson, or flutemetamol F 18.

Other Agents

In some embodiments, the first liquid contains an agent to produce particles for non-therapeutic or non-diagnostic use. Such particles may include, but are not limited to, agents such as silica, titania, metals or other elements, metal salts, metal oxides, metal nitrides, metal sulfides, metal alkoxides, and/or polymers. This approach presents an alternative to sol-gel synthesis and provides particles for a diverse set of applications, including semiconductor particles (e.g., lead sulfide), surface plasmon resonance (e.g., gold), magnetism (e.g., iron oxide), UV-blocking (e.g., zinc oxide), imaging agents (e.g., silicon), and laser applications (e.g., poly(methyl methacrylate) and silicon dioxide mixtures).

EXAMPLES

The methods disclosed herein have been utilized in separate instances to prepare particles including at least one of several agents, e.g., whole human IgG or bovine IgG, or one of several monoclonal antibodies. Various analytical techniques were applied to assess the physical characteristics of the particles themselves as well as the structural and functional properties of the processed agents. Scanning electron microscopy and associated image analysis were used to study the particle morphology and size distribution, respectively. Various morphologies were achieved by controlling the properties of the first liquid and/or the second liquid. In some instances, the processing conditions conferred smooth particles of high sphericity and/or facile control of the mean particle size over a broad range with low dispersity. In certain cases, the particle surfaces were also decorated with excipients. Density and water content measurement demonstrated that the particles approached crystalline packing efficiencies and retained very low levels of residual moisture. The functional properties of the agents were also preserved, as evidenced by ELISA and binding assays performed on reconstituted material. This was corroborated by size exclusion HPLC analysis indicating that the process had a minimal or even remedial effect on the degree of inter-protein association. Finally, investigation of the Sub-visible Particle (SvP) population revealed very few insoluble artifacts, particularly compared to alternative particle formation procedures.

Materials and Methods

Human IgG (IRHUGGF-LY, >97%) and bovine IgG (IRBVGGF) were obtained from Innovative Research as a lyophilized powder and an aqueous solution, respectively. The antibody products (mAb1, mAb2, mAb3, mAb4) were obtained in aqueous solution. The latter three mAbs were used as received while mAb1 was reformulated based on conditions of interest. Concentration columns were procured from Millipore Sigma (Amicon® Ultra 15 mL Filters for Protein Purification and Concentration with a 3 kDa cut off) and used where necessary to: (i) reach the desired protein concentration, and (ii) exchange buffer/excipients before particle formation. Zeba desalting columns (Thermo Fisher Scientific 87773) were also used to remove salt from solutions in certain instances. Typically, the ratio of residual salt to agent in the desalted solutions (wt/wt) was <1%. All excipients were purchased from Sigma-Aldrich and used as received.

Desiccation liquids, i.e., second liquids, included benzyl benzoate, various alcohols, various acetates, oils, surfactants, and aqueous media comprising different forms of polyethylene glycol (PEG). Benzyl benzoate is an organic liquid, largely immiscible with water, which exhibits a density (d=1.12 g/cm$^3$) that typically brackets that of the liquid feed solution (d≈1 g/cm$^3$ in the case of water) and the density of solid proteins, i.e., the density of the dry protein powder (d≈1.25-1.35 g/cm$^3$). It therefore served as a medium upon which drops floated while undergoing primary desiccation via dispersal of the first liquid in the benzyl benzoate and evaporation of the first liquid in the surrounding medium, e.g., air (typically of order several seconds or less). The desiccated particles sunk thereafter, such that a spatial separation was generated between wet incoming drops and processed particles. Such separation helped to mitigate particle coalescence, among other phenomena. The remaining liquids typically exhibited a density less than or approximately that of the feed solution. Drops did not tend to float, and primary desiccation was therefore driven primarily by dispersal of the first liquid in the second liquid. All desiccation ("second") liquids were purchased from Sigma Aldrich and used as received.

Particle Formation

Unless otherwise noted, an electrospray apparatus was used to form drops for desiccation and particle formation. In most instances this apparatus comprised a Sono-Tek 120 kHz ultrasonic atomizer charged by a Matsusada EQ-30P1-LCt or EQ-30N1-LCt high voltage DC power supply, while in others it was replaced by a small blunt disposable syringe needle (VWR International). A Harvard Apparatus Model 33 dual-channel syringe pump was utilized for pumping the feed solution. The drops generated by the apparatus were collected for desiccation by a vessel containing the second liquid, typically under conditions of continuous stirring. Thermal management of the second liquid was utilized in the preparation of select samples. The distance between the surface of the second liquid in the vessel and the tip of the drop source was typically 10-20 cm.

Lyophilization

The particles for lyophilized samples, i.e., samples marked as having gone through a secondary desiccation step involving freeze drying, were loaded into either microcentrifuge or 15 mL conical tubes and subjected to snap freezing by immersion in liquid nitrogen for approximately 10 min. The samples were then loosely covered and transferred to either a Virtis Advantage or a Labconco FreeZone lyophilizer for approximately 24 hours at a pressure of approximately 10-50 mTorr.

Scanning Electron Microscopy

Electron micrographs were collected for select samples with either a Hitachi TM3030Plus or a TM1000 tabletop microscope. The samples were immobilized on conductive tape and examined in a low-vacuum anti-charging environment, obviating the need for sample preparation.

Image Analysis

Select microscopy images were chosen for further analysis on the basis of (i) minimal particle overlapping, (ii) good contrast between the particles and the background, and (iii) a resolution providing for particle occupancies of at least 10 pixels. This allowed for particles to be easily identified and reduced resolution-based error. A binary threshold was applied to separate the particles from background, and a watershed segmentation algorithm was applied to ensure that individual particles were measured separately. The ImageJ tool "Analyze Particles" was then applied on the binary picture with the following parameters: circularity between 0.5 and 1.0; size between 5 and infinity square microns; exclude on edges; fill holes. The outlines of the identified particles were overlaid onto the original image. Particles which were misidentified, such as clusters that were identified as a single particle or particles whose outlines do not match the particle, were then discarded. Missing particles were measured by manually tracing the particle's outline and using ImageJ's Measure tool.

Density Analysis

The skeletal density of particles from select samples was determined by examining approximately 0.1 g of powder with an AccuPyc II 1340 gas displacement pycnometry system.

Water Content Analysis

The residual moisture in particles from select samples was determined by placing approximately 0.1 g of powder in a vacuum oven with a Karl Fischer titrator and heating the sample.

Elisa Assay

ELISA assay was used on select samples to detect human antibody in a denaturation sensitive manner. Human IgG was first plated in PBS for 1 hour, followed by washing with wash buffer (PBS+0.05% Tween20) three times for 4 minutes, followed by blocking with 2% BSA (Sigma) in wash buffer for 45 minutes, followed by incubation with dilute (20 µg/mL) protein A-HRP (Abcam) for 45 minutes, followed by wash buffer three times for 3 minutes, followed by incubation with TMB (Abcam) for 10 minutes, finally followed by quenching of the reaction with STOP solution (Abcam). The colorimetric readout was conducted on a Thermo Multiskan Spectrum.

Size Exclusion Chromatography

The quantification of size variants in select samples was determined by size exclusion chromatography. This analysis utilized an AdvanceBio SEC-3 column, 7.8 mm ID×30 cm, 3 μm (Agilent) run on an HPLC system (1260 Infinity II, Agilent). The mobile phases were 25 mM potassium phosphate and 0.25 M potassium chloride at pH 6.8. The chromatography was run isocractically at a flow rate of 1.0 mL/min for 15 minutes. The column temperature was maintained at ambient 25° C. and the eluent absorbance was monitored at 280 nm. Each monoclonal antibody was diluted with its respective formulation buffer to 1 mg/mL. The injection volume was 10 μL.

Cation Exchange Chromatography (CIEX)

Charge variant analysis was performed for each sample using an Agilent BioMAb NP5, 4.6×250 mm, PEEK ion exchange column. Samples were prepared at 1 mg/mL concentration after overnight dialysis in water. Buffer A was prepared with: 30 mM phosphate, pH: 6.3, and NaCl: 0 mM. Buffer B was prepared with: Buffer A: 30 mM phosphate, pH 6.3 plus NaCl: 175 mM. The samples were run in a gradient starting with 100% Buffer A, ramping up to a 100% Buffer B over a course of 20 min, after which the gradient was set to return to 100% Buffer A and 0% Buffer B in the next 1 min. The system re-equilibrated in 100% Buffer A for 10 min before the injection of the next sample. Integration was performed as a manual skim peak mode to reflect the Agilent data in the following protocol: https://www.agilent.com/cs/library/applications/5991-5557EN.pdf Subvisible Particle (SVP) Analysis Subvisible particles (SvPs) were analyzed with a Fluid Imaging Technologies FlowCam PV-100 system. Samples for analysis were reconstituted in sterile centrifuge tubes with filtered water (Milli-Q) to the concentration of interest. Three sets of samples were investigated thereafter. These included (i) a sample of the diluent used for reconstitution, (ii) an aliquot of the feed solution used for the particle formation process, i.e., a sample of the first liquid, and (iii) the reconstituted material.

Monoclonal Antibody Binding Assay (Flow Cytometry)

Monoclonal antibodies from select samples were assessed for cellular binding ability utilizing cells that express the appropriate cell surface receptors. Cells were incubated for 30 minutes at 4° C. with monoclonal antibodies at respective concentrations and then spun down at 2000 rpm followed by washing with PBS three times. Cells were then incubated with secondary goat anti-human Fab antibody fluorescently labeled with PE for 30 minutes at 4° C. The cells were then spun down at 2000 rpm followed by washing with PBS, three times. The cells were then re-suspended and then analyzed on an Attune Flow Cytometer (Invitrogen).

Antibody-Dependent Cell-Mediated Cytotoxicity (ADCC)

Using an ADCC luciferase-based kit (Promega-G7015), target cells were plated in a 96 well plate (25 μL per well; 12,500 cells per 25 μL). 25 μL of antibody solution (2 μg/mL starting concentration) was added to each well, after which a 3× serial dilution was carried out. Effector cells were added (25 μL per well; 75,000 cells per 25 μL) and the plate was incubated at 37° C. for 6 h in an incubator. The plate was then equilibrated at RT for 15 min before addition of 30 μL Luciferin reagent to each well. The luminescence was measured using a Thermo Scientific Varioskan LUX luminometer.

Accelerated Storage

Storage was carried out under accelerated conditions for select samples by maintaining them at an elevated temperature (40° C.) for defined periods of time in an incubator or oven. Samples were kept in 2 mL or 4 mL Wheaton glass vials and sealed with paraffin film.

Results

Example 1

Figure 13:
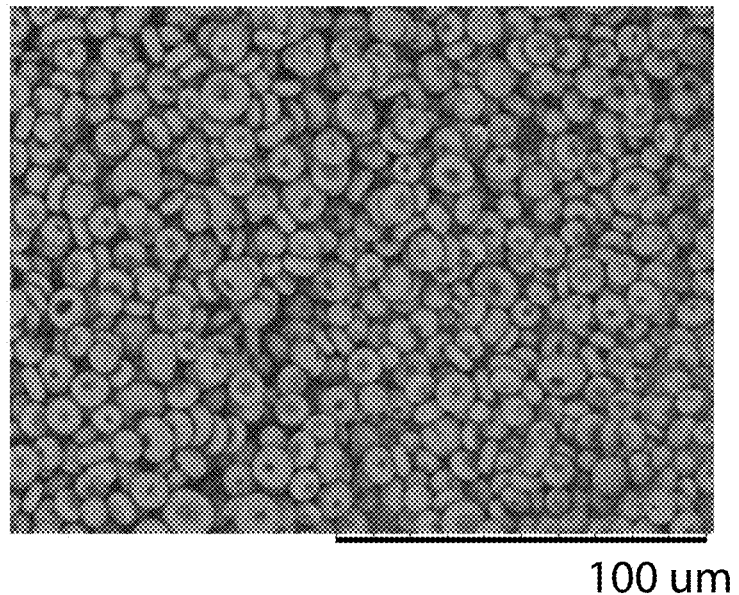

Human IgG powder was reconstituted in salt solution to a protein concentration of approximately 70 mg/mL without desalting or otherwise modifying the solution. The solution was atomized and collected with a perfluoroalkoxy (PFA) vessel containing 200 mL of benzyl benzoate held at 40-50° C. under conditions of gentle stirring. After primary desiccation, particles were collected, washed, and allowed to undergo secondary desiccation under ambient conditions, i.e., by evaporation of the remaining liquids in air. SEM images revealed identifiable particulate matter (FIGS. 9A-9D).

Example 2

Human IgG powder was reconstituted in deionized water to a protein concentration of approximately 25 mg/mL. The solution was atomized and collected with a PFA vessel containing 5 mL of 1-ethyl-3-methyl imidazolium tetrafluoroborate (EMI-BF4) held near 40° C. After primary desiccation, particles were collected, washed, and vacuum dried to remove residual liquid.

Example 3

Human IgG powder was reconstituted in deionized water to a protein concentration of approximately 50 mg/mL. The solution was desalted and a quantity of trehalose (50 mg/mL) was added, after which it was atomized and collected with a stainless steel vessel containing 200 mL of ethanol held near room temperature under conditions of gentle stirring. Approximately 1 mL of feed solution was processed. After primary desiccation, particles were collected, washed, and vacuum dried to remove residual liquid. SEM images revealed identifiable particulate matter (FIG. 10).

Example 4

Human IgG powder was reconstituted in deionized water to a protein concentration of approximately 50 mg/mL. The solution was desalted and a quantity of trehalose (50 mg/mL) was added, after which it was atomized and collected with a stainless steel vessel containing 200 mL of isopropanol held near room temperature under conditions of gentle stirring. Approximately 1 mL of feed solution was processed. After primary desiccation, particles were collected, washed, and vacuum dried to remove residual liquid. SEM images revealed identifiable particulate matter (FIGS. 11A-11B).

Example 5

Human IgG powder was reconstituted in deionized water to a protein concentration of approximately 50 mg/mL. The solution was desalted and quantities of trehalose (50 mg/mL) and Tween 20 (5 mg/mL) were added, after which it was atomized and collected with a stainless steel vessel containing 200 mL of isopropanol held near room temperature under conditions of gentle stirring. Approximately 1 mL of feed solution was processed. After primary desiccation, particles were collected, washed, and vacuum dried to remove residual liquid. SEM images revealed identifiable particulate matter (FIGS. 12A-12B).

Example 6

Human IgG powder was reconstituted in deionized water to a protein concentration of approximately 50 mg/mL. The solution was desalted and a quantity of trehalose (50 mg/mL) was added, after which it was atomized and collected with a stainless steel vessel containing 200 mL of butanol held near room temperature under conditions of gentle stirring. Approximately 1 mL of feed solution was processed. After primary desiccation, particles were collected, washed, and vacuum dried to remove residual liquid. SEM images revealed identifiable particulate matter (FIG. 13).

Example 7

Figure 14:
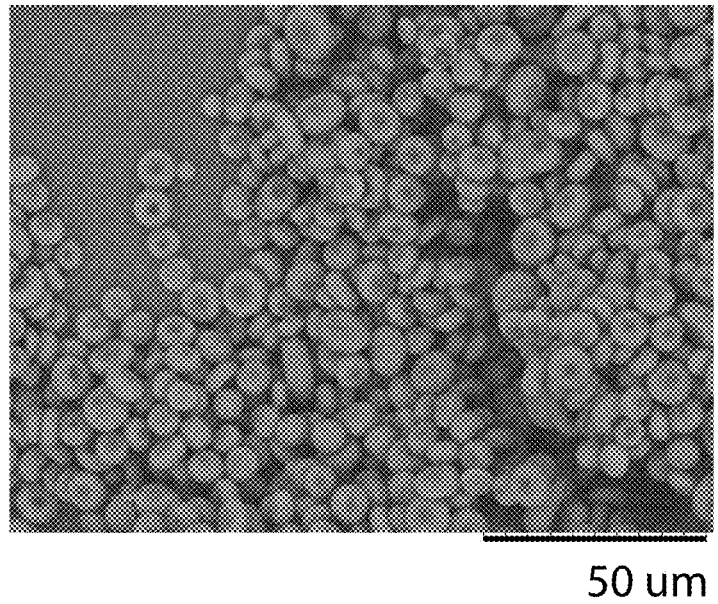

Human IgG powder was reconstituted in deionized water to a protein concentration of approximately 50 mg/mL. The solution was desalted and quantities of trehalose (50 mg/mL) and Tween 20 (5 mg/mL) were added, after which it was atomized and collected with a stainless steel vessel containing 200 mL of butanol held near room temperature under conditions of gentle stirring. Approximately 1 mL of feed solution was processed. After primary desiccation, particles were collected, washed, and vacuum dried to remove residual liquid. SEM images revealed identifiable particulate matter (FIG. 14).

Example 8

Figure 15A:
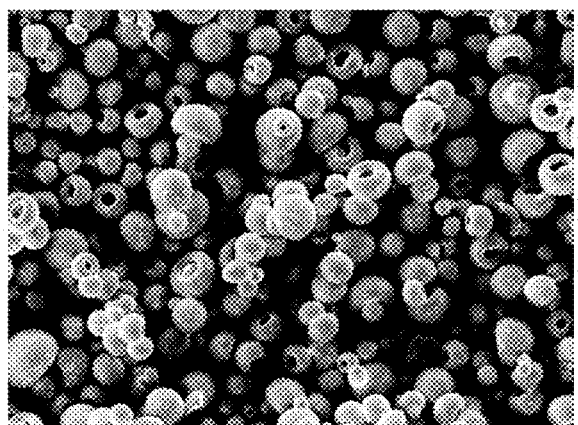
Figure 15C:
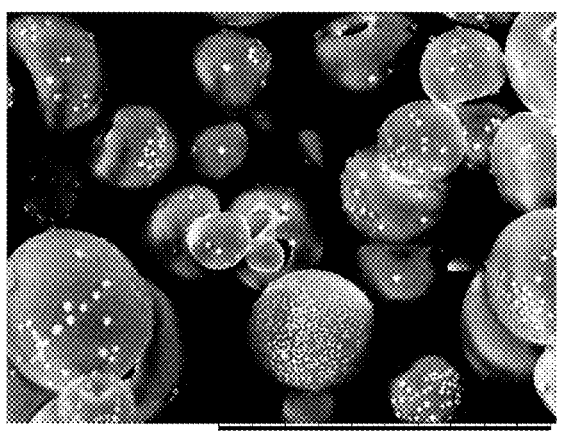
Figure 15B:
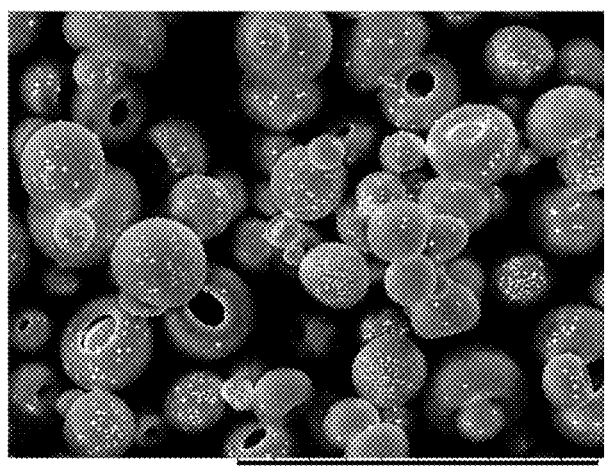

Human IgG powder was reconstituted in deionized water to a protein concentration of approximately 70 mg/mL without desalting or otherwise modifying the solution. The solution was atomized and collected with a perfluoroalkoxy alkane (PFA) vessel containing 50 mL of ethyl acetate held near 35° C. After primary desiccation, particles were collected, washed, and allowed to undergo secondary desiccation under ambient conditions, i.e., by evaporation of the remaining liquids in air. SEM images revealed identifiable particulate matter (FIGS. 15A-15C).

Example 9

Figure 16:
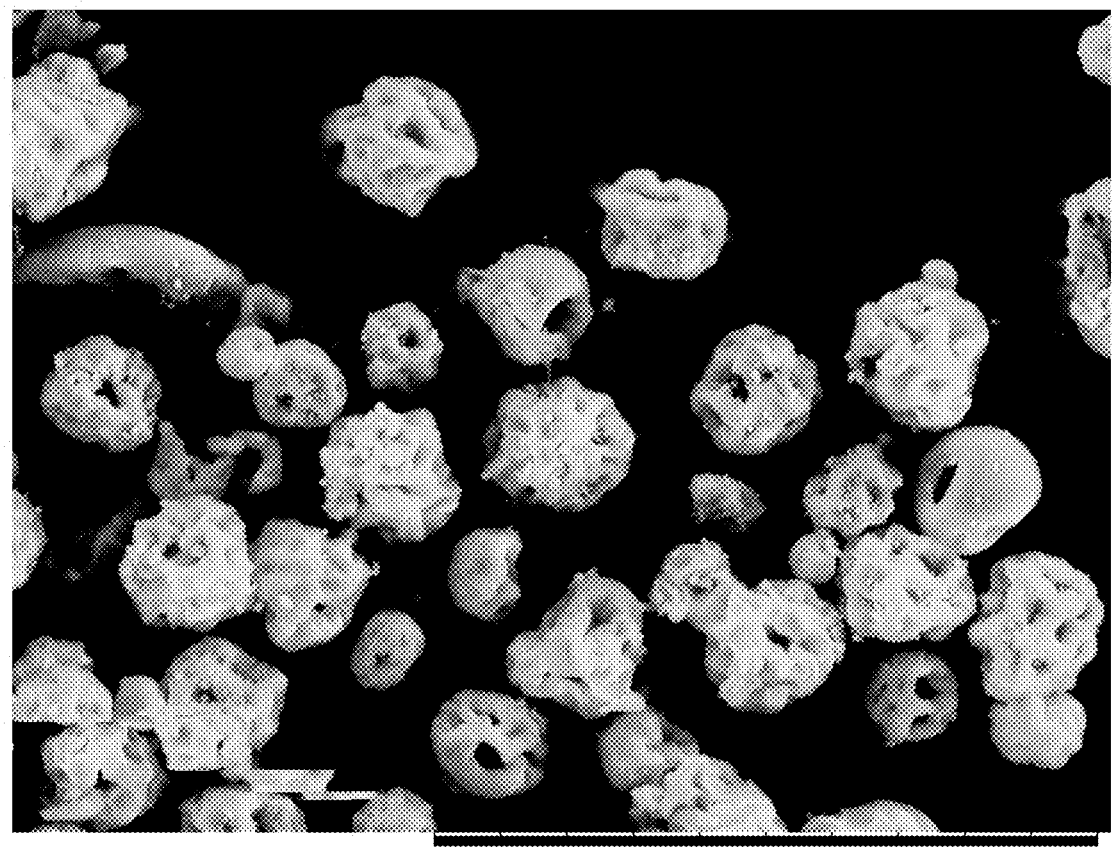

Human IgG powder was reconstituted in deionized water to a protein concentration of approximately 10 mg/mL without desalting or otherwise modifying the solution. The solution was atomized and collected with a perfluoroalkoxy alkane (PFA) vessel containing 200 mL of ethyl acetate held near room temperature. After primary desiccation, particles were collected, washed, and allowed to undergo secondary desiccation under ambient conditions, i.e., by evaporation of the remaining liquids in air. SEM images revealed identifiable particulate matter (FIG. 16).

Example 10

Figure 17A:
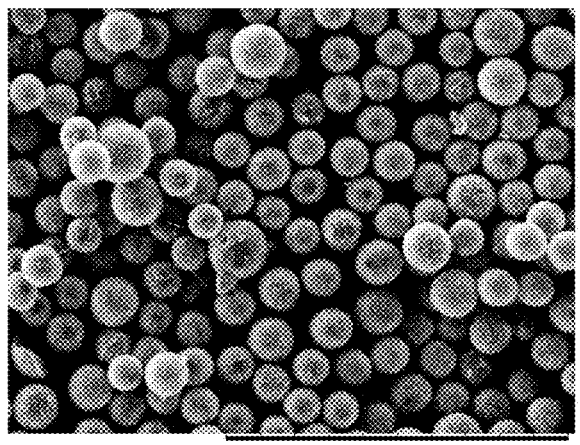
Figure 17C:
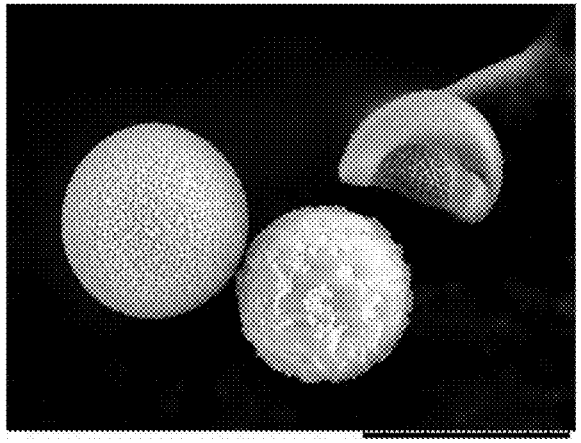
Figure 17B:
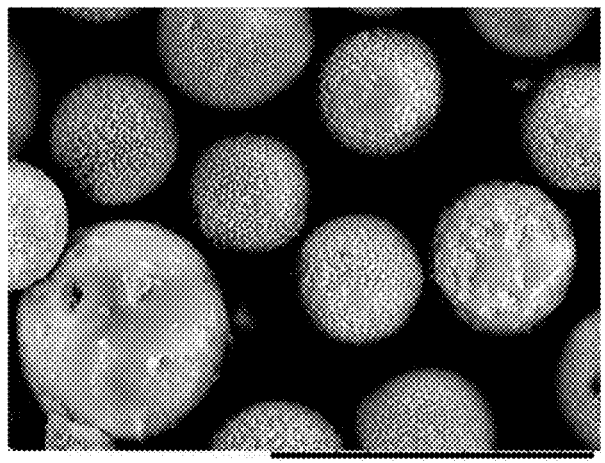

Human IgG powder was reconstituted in deionized water to a protein concentration of approximately 70 mg/mL without desalting or otherwise modifying the solution. The solution was atomized and collected with a perfluoroalkoxy alkane (PFA) vessel containing 200 mL of butyl acetate held near room temperature. After primary desiccation, particles were collected, washed, and allowed to undergo secondary desiccation under ambient conditions, i.e., by evaporation of the remaining liquids in air. SEM images revealed identifiable particulate matter (FIGS. 17A-17C).

Example 11

Figure 18A:
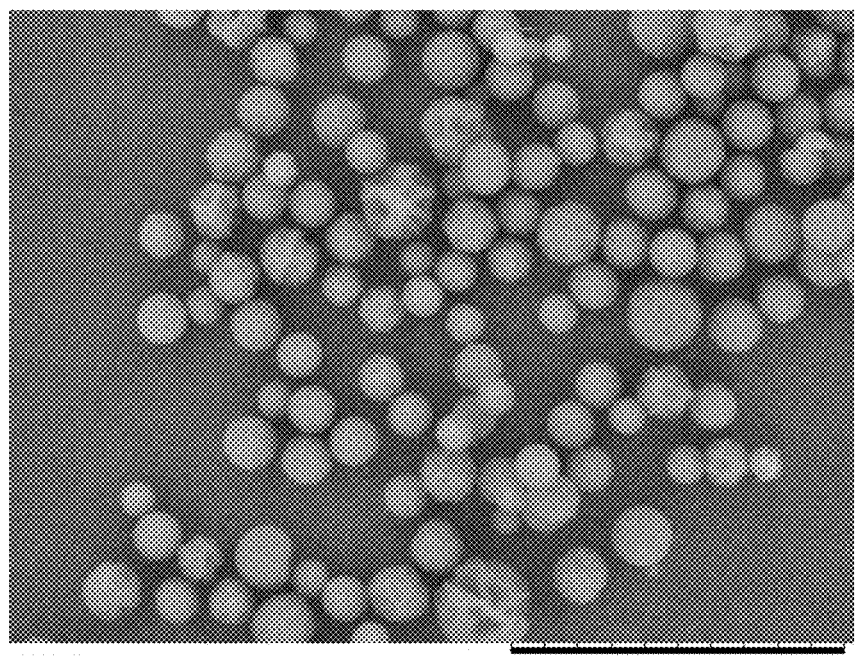
Figure 18B:
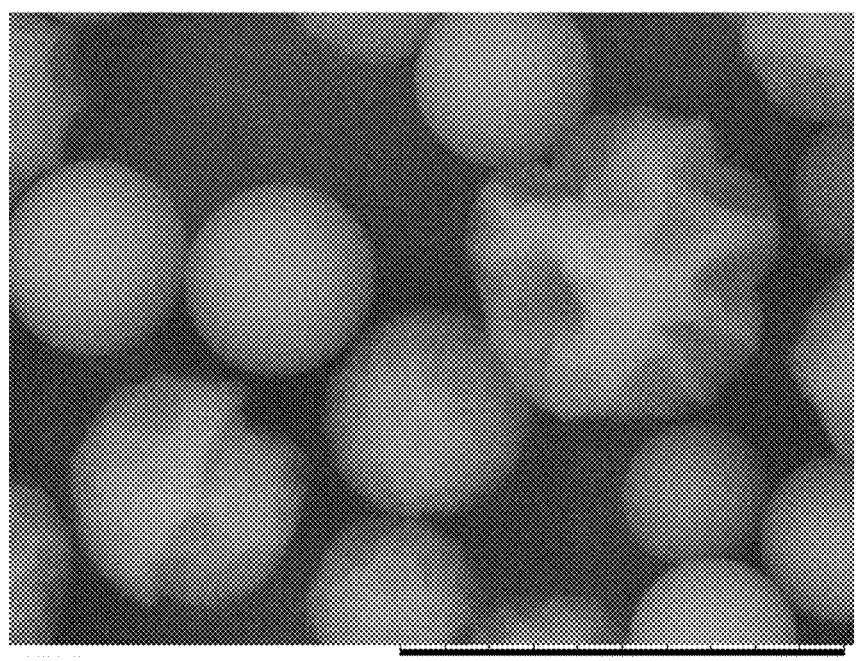

Human IgG powder was reconstituted in deionized water to a protein concentration of approximately 20 mg/mL. The solution was desalted, after which it was atomized and collected with a stainless steel vessel containing 200 mL of butyl acetate held near room temperature under conditions of gentle stirring. Approximately 2 mL of feed solution was processed. After primary desiccation, particles were collected, washed, and vacuum dried to remove residual liquid. SEM images revealed identifiable particulate matter (FIGS. 18A-18B).

Example 12

Figure 19A:
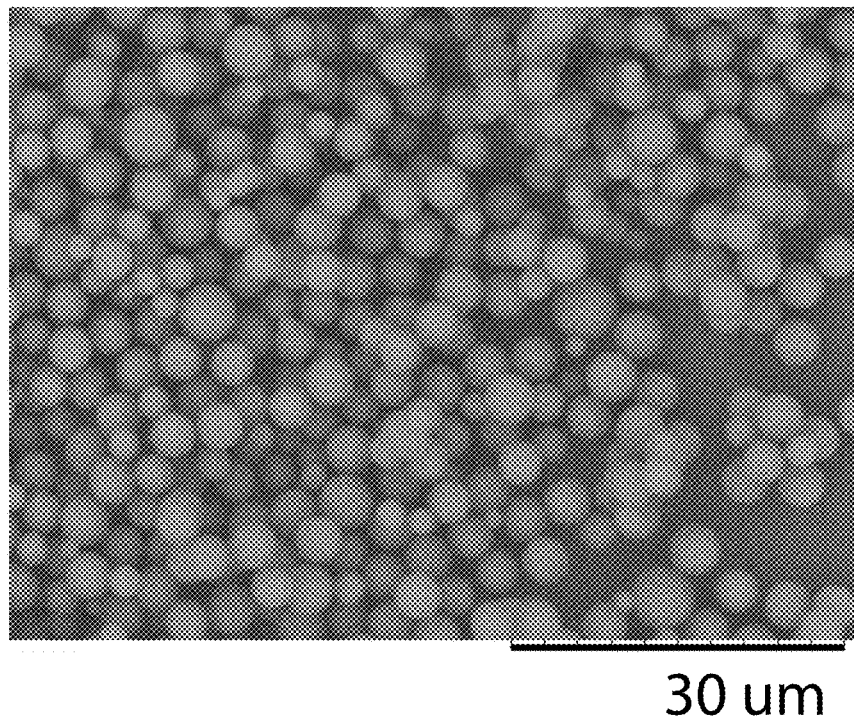
Figure 19B:
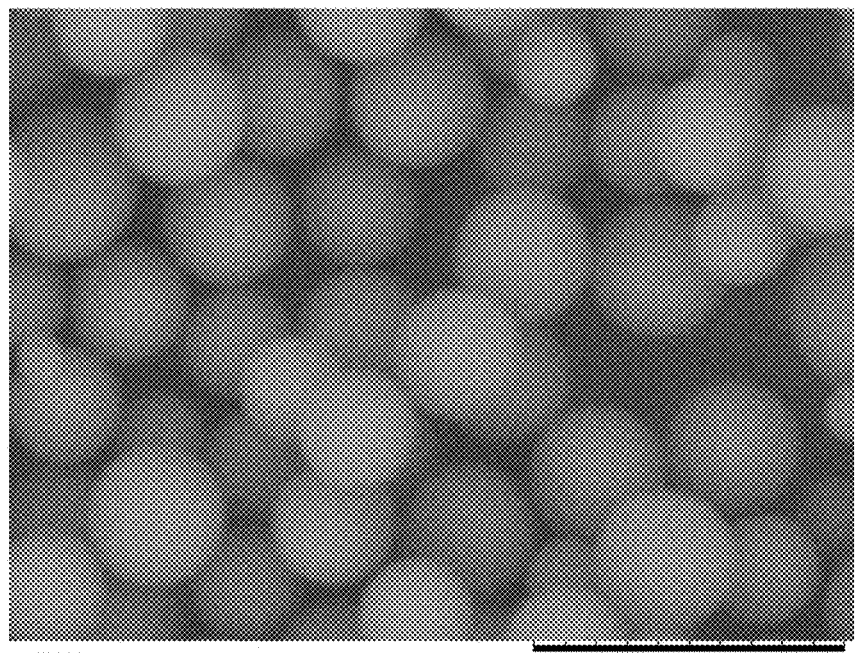

Human IgG powder was reconstituted in deionized water to a protein concentration of approximately 20 mg/mL. The solution was desalted and a quantity of Tween 20 (5 mg/mL) was added, after which it was atomized and collected with a stainless steel vessel containing 200 mL of butyl acetate held near room temperature under conditions of gentle stirring. Approximately 2 mL of feed solution was processed. After primary desiccation, particles were collected, washed, and vacuum dried to remove residual liquid. SEM images revealed identifiable particulate matter (FIGS. 19A-19B).

Example 13

Figure 20A:
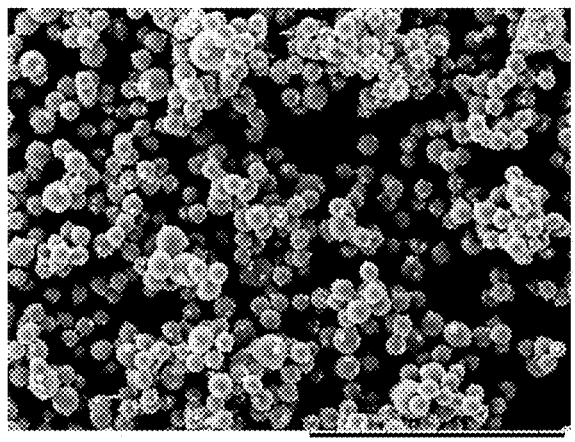
Figure 20C:
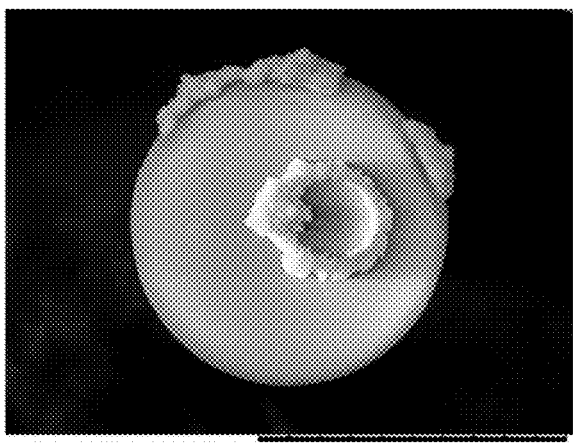
Figure 20B:
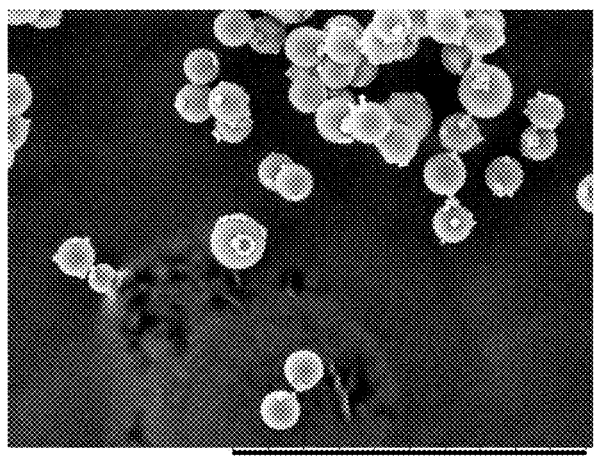

Human IgG powder was reconstituted in deionized water to a protein concentration of approximately 70 mg/mL without desalting or otherwise modifying the solution. The solution was atomized and collected with a perfluoroalkoxy alkane (PFA) vessel containing 200 mL of 2-ethylhexyl acetate held near room temperature under conditions of gentle stirring. Approximately 0.9 mL of feed solution was atomized. After primary desiccation, particles were collected, washed, and allowed to undergo secondary desiccation under ambient conditions, i.e., by evaporation of the remaining liquids in air. SEM images revealed identifiable particulate matter (FIGS. 20A-20C).

Example 14

Human IgG powder is reconstituted in deionized water to a protein concentration of approximately 50 mg/mL. The solution is desalted and a quantity of trehalose (50 mg/mL) is added, after which it is atomized and collected with a stainless steel vessel containing 200 mL of an aqueous solution of PEG 3350 (40 wt %) held near room temperature under conditions of gentle stirring. Approximately 1 mL of feed solution is processed. After primary desiccation, particles are collected, washed, and vacuum dried to remove residual liquid.

Example 15

Human IgG powder is reconstituted in deionized water to a protein concentration of approximately 50 mg/mL. The solution is desalted and a quantity of trehalose (50 mg/mL) is added, after which it is atomized and collected with a stainless steel vessel containing 200 mL of an aqueous solution of PEG 4000 (40 wt %) held near room temperature under conditions of gentle stirring. Approximately 1 mL of feed solution is processed. After primary desiccation, particles are collected, washed, and vacuum dried to remove residual liquid.

Example 16

Human IgG powder is reconstituted in deionized water to a protein concentration of approximately 50 mg/mL. The solution is desalted and quantities of trehalose (50 mg/mL) and Tween 20 (5 mg/mL) are added, after which it is atomized and collected with a stainless steel vessel containing 200 mL of an aqueous solution of PEG 4000 (40 wt %) held near room temperature under conditions of gentle stirring. Approximately 1 mL of feed solution is processed. After primary desiccation, particles are collected, washed, and vacuum dried to remove residual liquid.

Example 17

Human IgG powder is reconstituted in deionized water to a protein concentration of approximately 50 mg/mL. The solution is desalted and a quantity of trehalose (50 mg/mL) is added, after which it is atomized and collected with a stainless steel vessel containing 200 mL of an aqueous solution of PEG 20000 (20 wt %) held near room temperature under conditions of gentle stirring. Approximately 1 mL of feed solution is processed. After primary desiccation, particles are collected, washed, and vacuum dried to remove residual liquid.

Example 18

Human IgG powder is reconstituted in deionized water to a protein concentration of approximately 50 mg/mL. The solution is desalted and quantities of trehalose (50 mg/mL) and Tween 20 (5 mg/mL) are added, after which it is atomized and collected with a stainless steel vessel containing 200 mL of an aqueous solution of PEG 20000 (20 wt %) held near room temperature under conditions of gentle stirring. Approximately 1 mL of feed solution is processed. After primary desiccation, particles are collected, washed, and vacuum dried to remove residual liquid.

Example 19

Human IgG powder was reconstituted in deionized water to a protein concentration of approximately 50 mg/mL without desalting or otherwise modifying the solution. The solution was atomized and collected with a stainless steel vessel containing 400 mL of a solution of PEG 20000 (40 wt %) held near 40° C. under conditions of gentle stirring. Approximately 1 mL of feed solution was processed. After primary desiccation, particles were collected, washed, and vacuum dried to remove residual liquid.

Example 20

Human IgG powder is reconstituted in deionized water to a protein concentration of approximately 50 mg/mL. The solution is desalted and a quantity of trehalose (50 mg/mL) is added, after which it is atomized and collected with a stainless steel vessel containing 200 mL of 1-butyl-3-methylimidazolium chloride held near room temperature under conditions of gentle stirring. Approximately 1 mL of feed solution is processed. After primary desiccation, particles are collected, washed, and vacuum dried to remove residual liquid.

Example 21

Human IgG powder is reconstituted in deionized water to a protein concentration of approximately 50 mg/mL. The solution is desalted and a quantity of trehalose (50 mg/mL) is added, after which it is atomized and collected with a stainless steel vessel containing 200 mL of choline taurinate held near room temperature under conditions of gentle stirring. Approximately 1 mL of feed solution is processed. After primary desiccation, particles are collected, washed, and vacuum dried to remove residual liquid.

Example 22

Human IgG powder is reconstituted in deionized water to a protein concentration of approximately 50 mg/mL. The solution is desalted and quantities of trehalose (50 mg/mL) and Tween 20 (5 mg/mL) are added, after which it is atomized and collected with a stainless steel vessel containing 200 mL of choline taurinate held near room temperature under conditions of gentle stirring. Approximately 1 mL of feed solution is processed. After primary desiccation, particles are collected, washed, and vacuum dried to remove residual liquid.

Example 23

Human IgG powder is reconstituted in deionized water to a protein concentration of approximately 50 mg/mL. The solution is desalted and a quantity of trehalose (50 mg/mL) is added, after which it is atomized and collected with a stainless steel vessel containing 200 mL of an aqueous solution of choline acetate held near room temperature under conditions of gentle stirring. Approximately 1 mL of feed solution is processed. After primary desiccation, particles are collected, washed, and vacuum dried to remove residual liquid.

Example 24

Human IgG powder is reconstituted in deionized water to a protein concentration of approximately 50 mg/mL. The solution is desalted and quantities of trehalose (50 mg/mL) and Tween 20 (5 mg/mL) are added, after which it is atomized and collected with a stainless steel vessel containing 200 mL of choline acetate held near room temperature under conditions of gentle stirring. Approximately 1 mL of feed solution is processed. After primary desiccation, particles are collected, washed, and vacuum dried to remove residual liquid.

Example 25

Figure 21A:
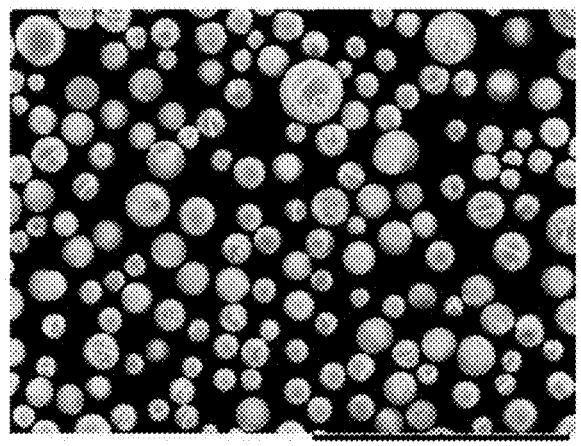
Figure 21C:
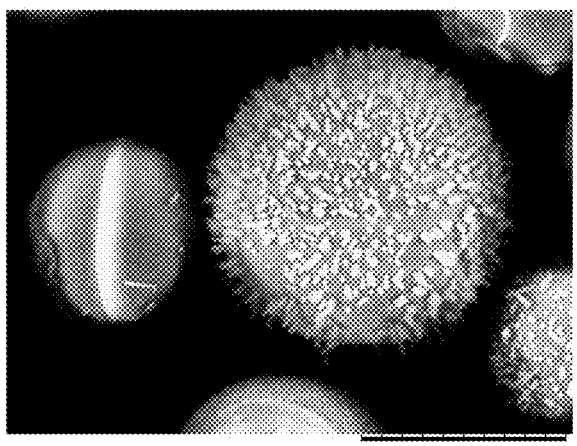
Figure 21B:
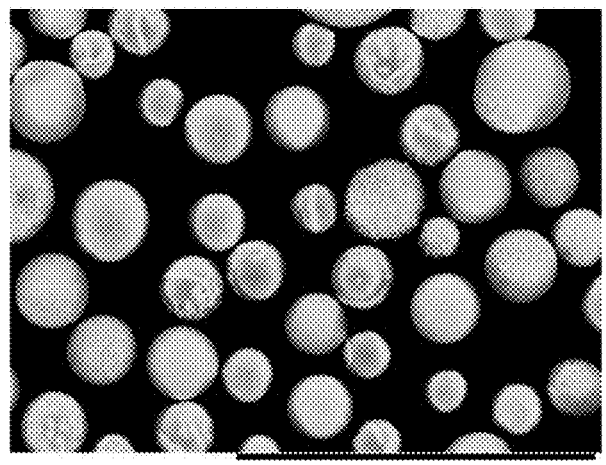

Human IgG powder was reconstituted in deionized water to a protein concentration of approximately 70 mg/mL without desalting or otherwise modifying the solution. The solution was atomized and collected with a perfluoroalkoxy alkane (PFA) vessel containing 100 mL of a mixture comprising ethyl acetate and benzyl benzoate (50:50 v/v %) held near room temperature. Approximately 0.5 mL of feed solution was atomized. After primary desiccation, particles were collected, washed, and allowed to undergo secondary desiccation under ambient conditions, i.e., by evaporation of the remaining liquids in air. SEM images revealed identifiable particulate matter (FIGS. 21A-21C).

Example 26

Figure 22A:
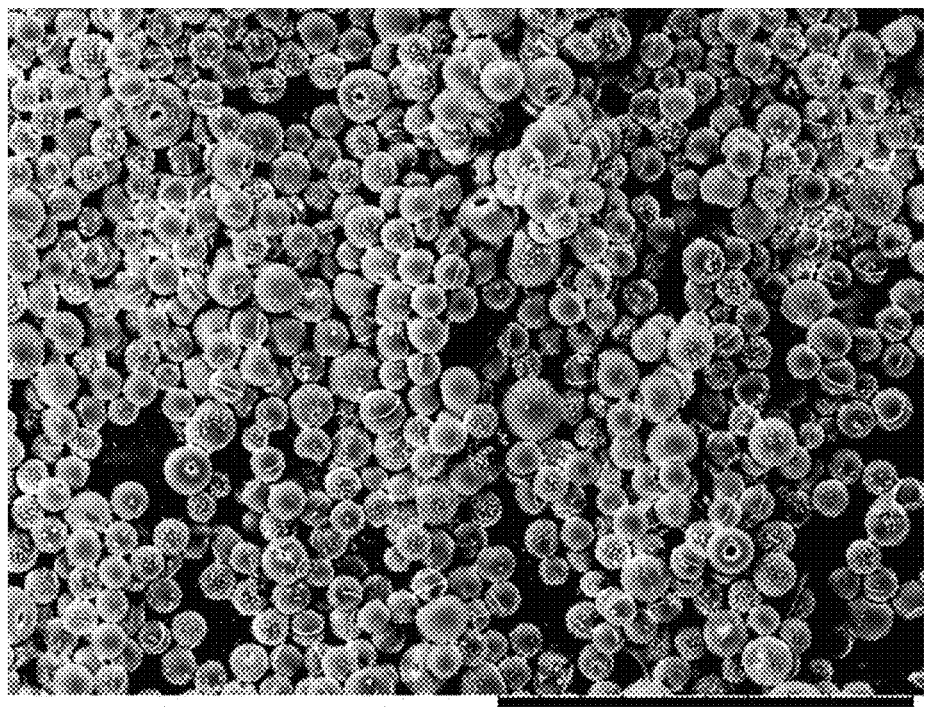
Figure 22B:
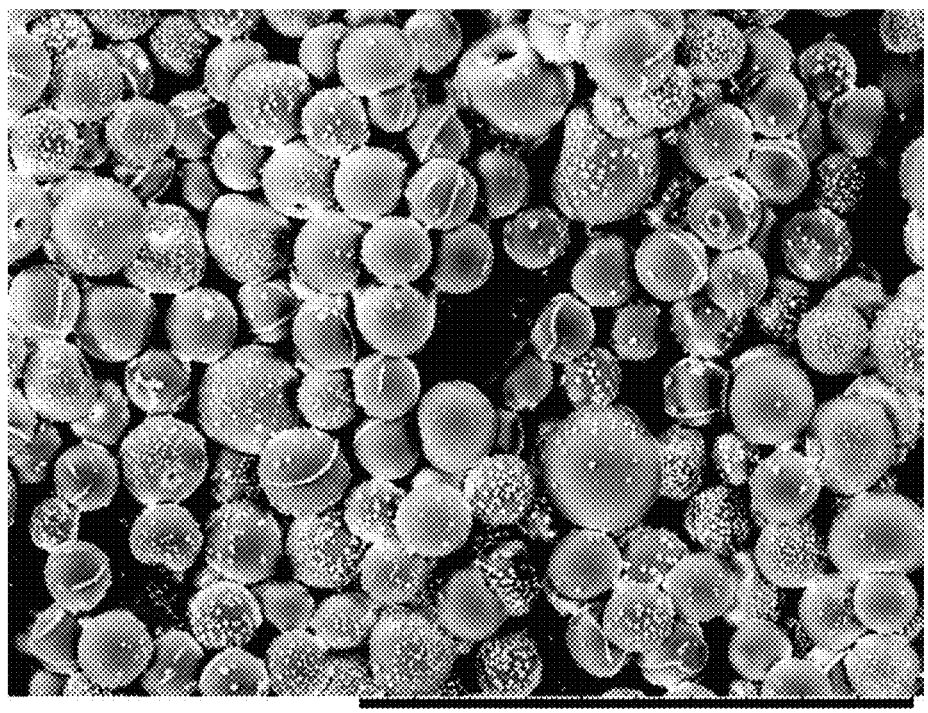

Human IgG powder was reconstituted in deionized water to a protein concentration of approximately 35 mg/mL without desalting or otherwise modifying the solution. The solution was atomized and collected with a perfluoroalkoxy alkane (PFA) vessel containing 100 mL of a mixture comprising ethyl acetate and benzyl benzoate (75:25 v/v %) held near 35° C. Approximately 0.4 mL of feed solution was atomized. After primary desiccation, particles were collected, washed, and allowed to undergo secondary desiccation under ambient conditions, i.e., by evaporation of the remaining liquids in air. SEM images revealed identifiable particulate matter (FIGS. 22A-22B).

Example 27

Figure 23:
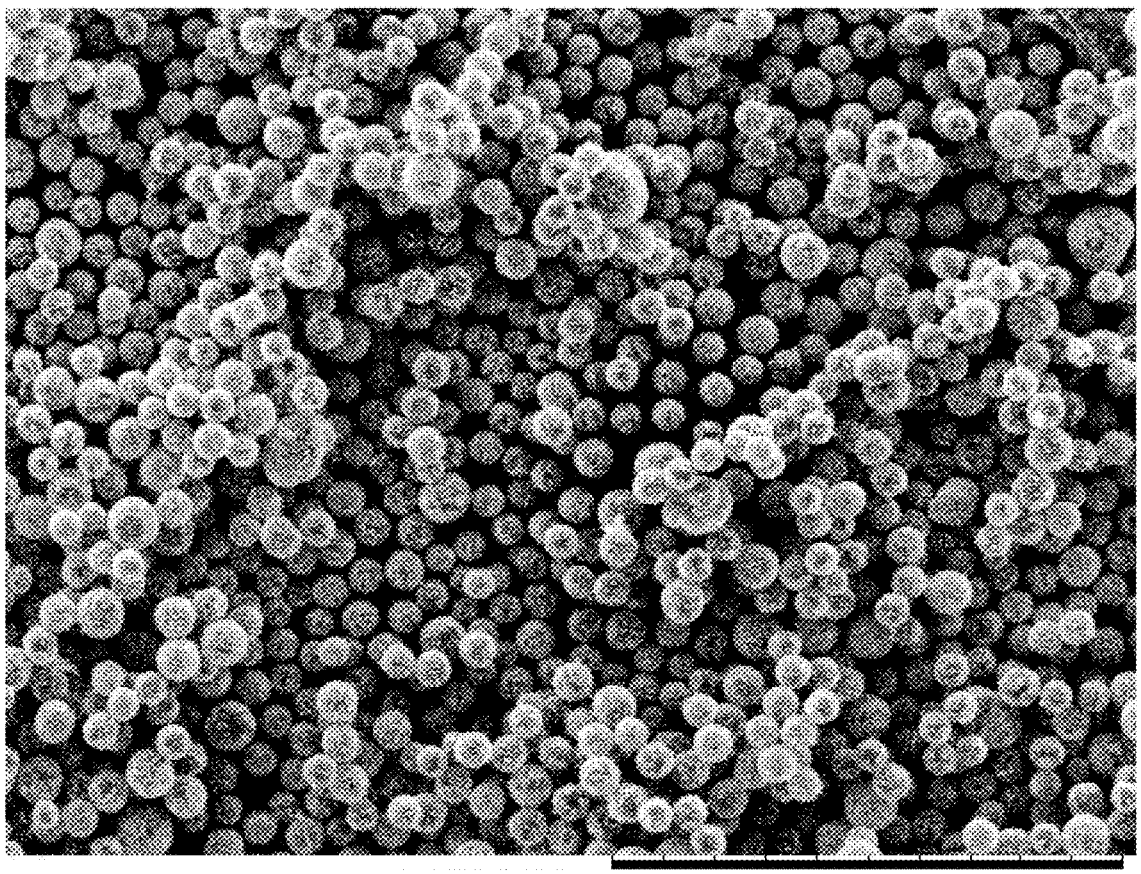

Human IgG powder was reconstituted in deionized water to a protein concentration of approximately 70 mg/mL without desalting or otherwise modifying the solution. The solution was atomized and collected with a perfluoroalkoxy alkane (PFA) vessel containing 200 mL of a mixture comprising ethyl acetate and cottonseed oil (75:25 v/v %) held near room temperature. After primary desiccation, particles were collected, washed, and allowed to undergo secondary desiccation under ambient conditions, i.e., by evaporation of the remaining liquids in air. SEM images revealed identifiable particulate matter (FIG. 23).

Example 28

Figure 24A:
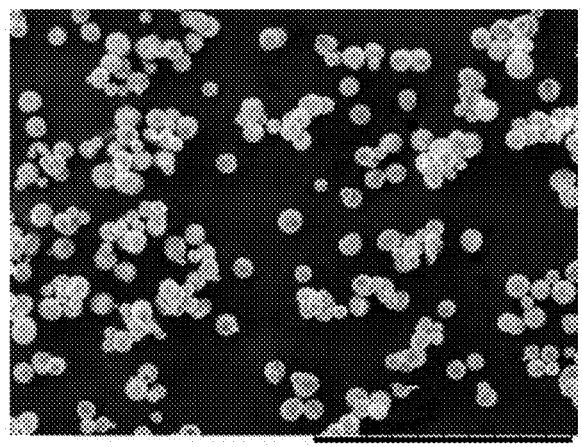
Figure 24C:
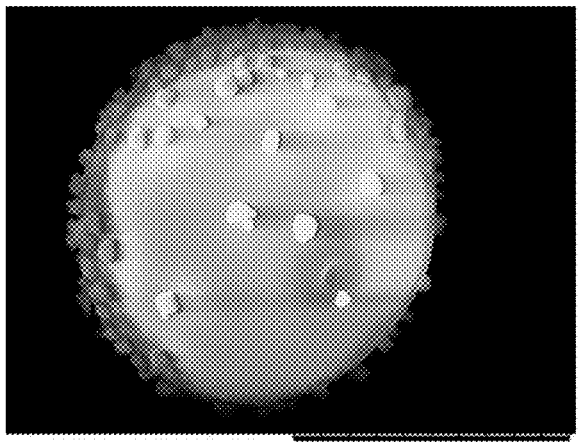
Figure 24B:
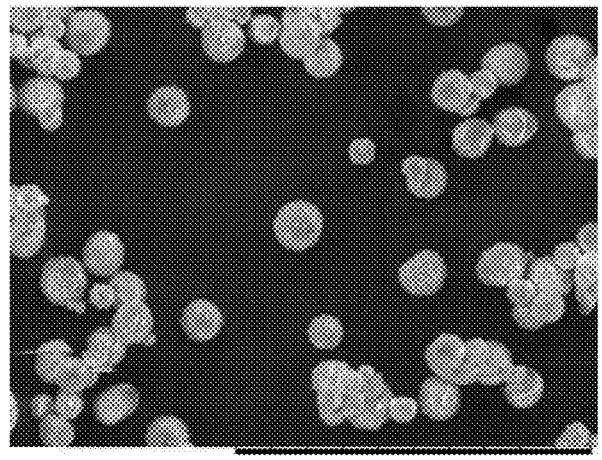

Human IgG powder was reconstituted in deionized water to a protein concentration of approximately 70 mg/mL without desalting or otherwise modifying the solution. The solution was atomized and collected with a perfluoroalkoxy alkane (PFA) vessel containing 200 mL of a mixture comprising ethyl acetate and toluene (75:25 v/v %) held near room temperature. After primary desiccation, particles were collected, washed, and allowed to undergo secondary desiccation under ambient conditions, i.e., by evaporation of the remaining liquids in air. SEM images revealed identifiable particulate matter (FIGS. 24A-24C).

Example 29

Figure 25:
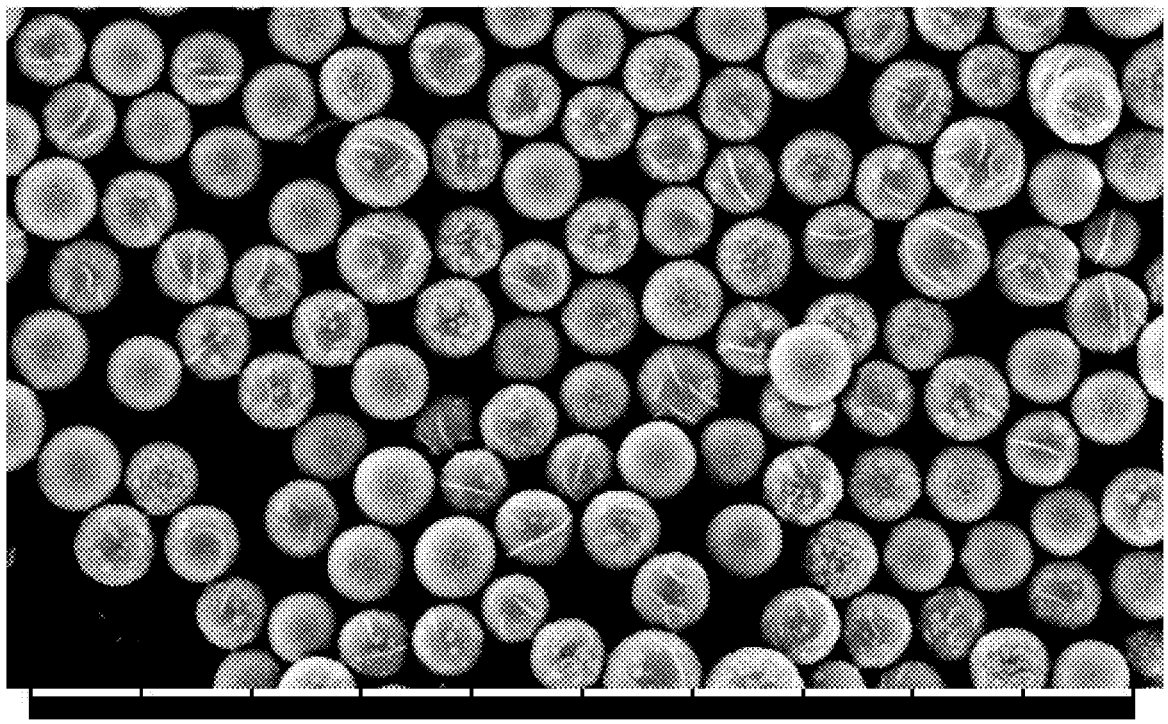
Figure 26A:
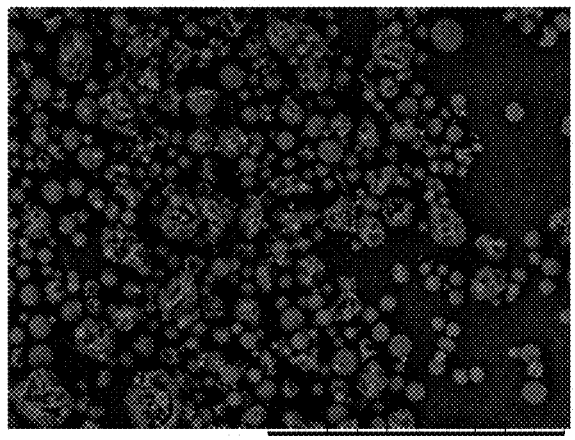
Figure 26C:
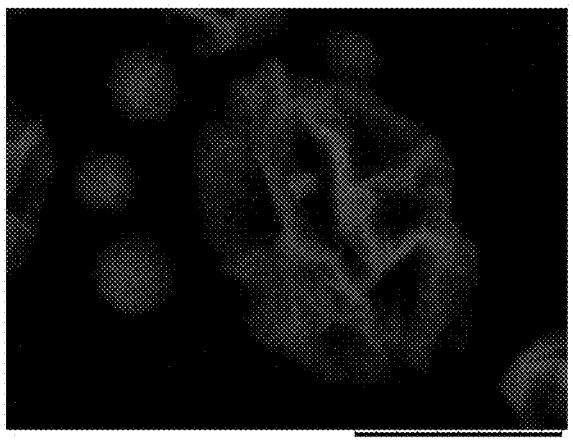
Figure 26B:
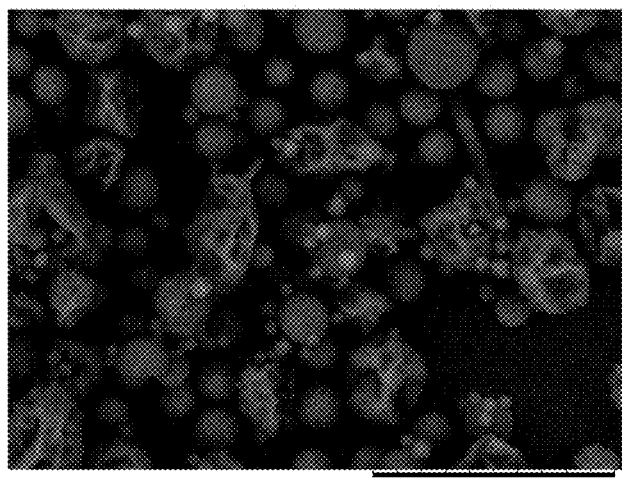
Figure 27A:
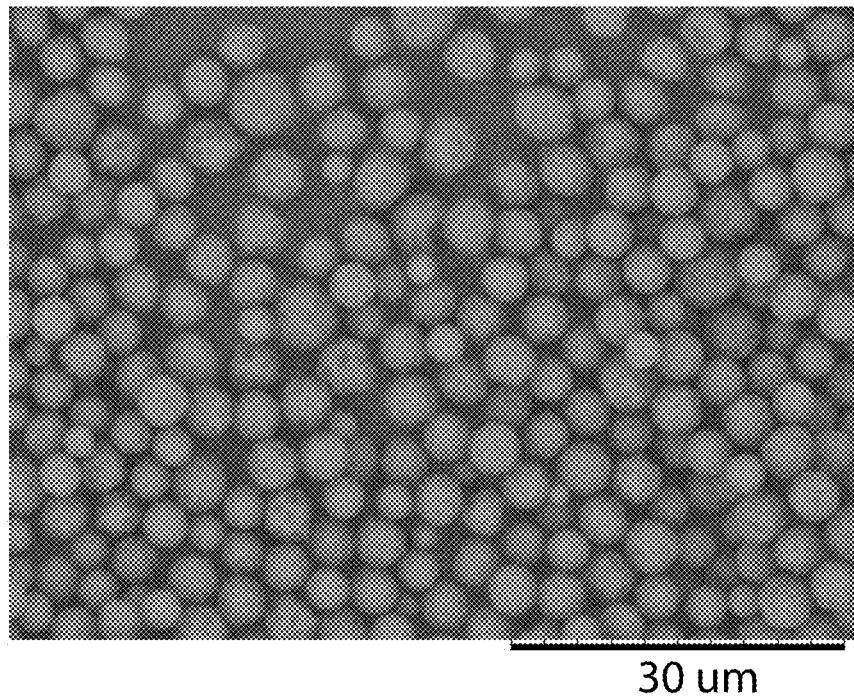
Figure 27B:
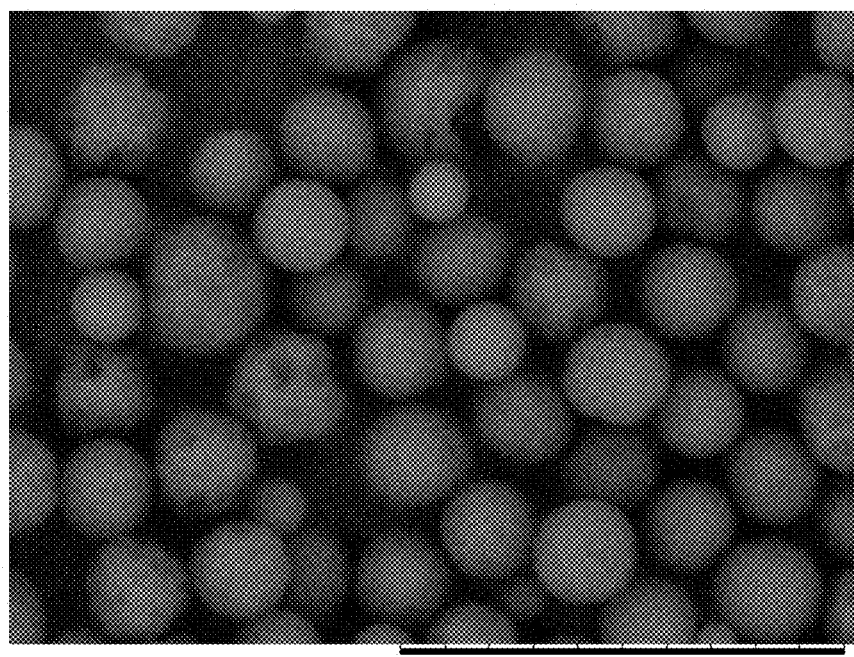
Figure 28A:
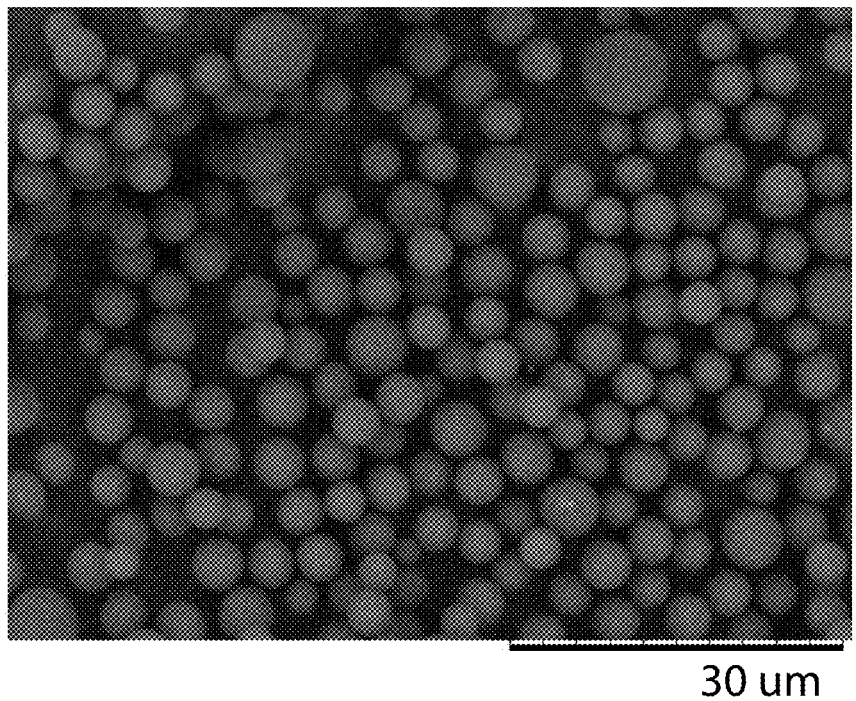
Figure 28B:
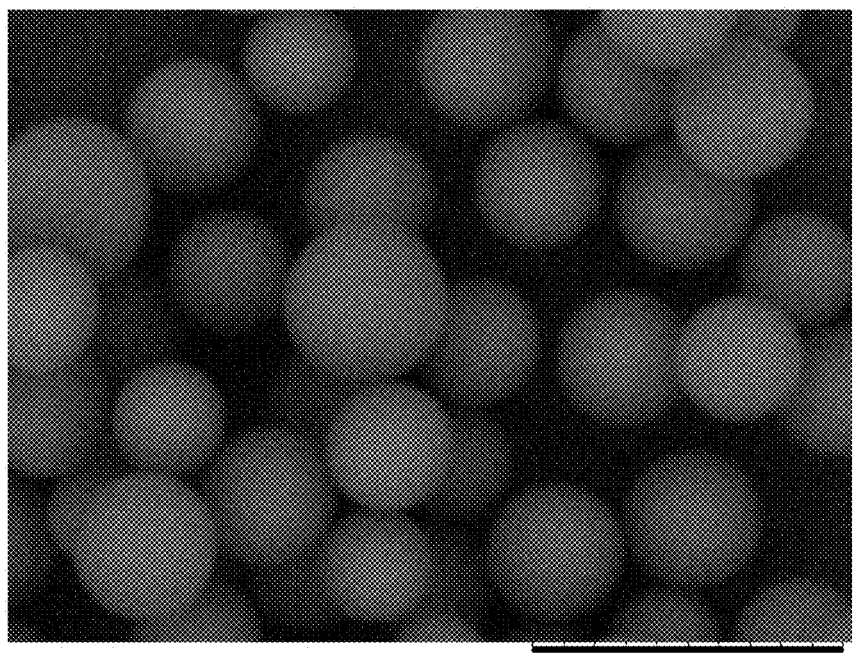

Human IgG powder was reconstituted in deionized water to a protein concentration of approximately 70 mg/mL without desalting or otherwise modifying the solution. The solution was atomized and collected with a perfluoroalkoxy alkane (PFA) vessel containing 200 mL of a mixture comprising butyl acetate and cottonseed oil (75:25 v/v %) held near room temperature. After primary desiccation, particles were collected, washed, and allowed to undergo secondary desiccation under ambient conditions, i.e., by evaporation of the remaining liquids in air. SEM images revealed identifiable particulate matter (FIG. 25).

Example 30

Human IgG powder was reconstituted in deionized water to a protein concentration of approximately 70 mg/mL. The solution was desalted, after which it was atomized and collected with a perfluoroalkoxy alkane (PFA) vessel containing 200 mL of a mixture comprising butyl acetate and cottonseed oil (75:25 v/v %) held near room temperature. After primary desiccation, particles were collected, washed, and allowed to undergo secondary desiccation under ambient conditions, i.e., by evaporation of the remaining liquids in air.

Example 31

Human IgG powder is reconstituted in deionized water to a protein concentration of approximately 70 mg/mL. The solution is desalted, after which it is atomized and collected with a perfluoroalkoxy alkane (PFA) vessel containing 200 mL of a mixture comprising 1-butyl-3-methylimidazolium chloride and butanol (75:25 v/v %) held near room temperature. After primary desiccation, particles are collected, washed, and vacuum dried to remove residual liquid.

Example 32

Human IgG powder is reconstituted in deionized water to a protein concentration of approximately 70 mg/mL. The solution is desalted, after which it is atomized and collected with a perfluoroalkoxy alkane (PFA) vessel containing 200 mL of a mixture comprising 1-butyl-3-methylimidazolium chloride and butyl acetate (75:25 v/v %) held near room temperature. After primary desiccation, particles are collected, washed, and vacuum dried to remove residual liquid.

Example 33

Human IgG powder is reconstituted in deionized water to a protein concentration of approximately 70 mg/mL. The solution is desalted, after which it is atomized and collected with a perfluoroalkoxy alkane (PFA) vessel containing 200 mL of a mixture comprising 1-butyl-3-methylimidazolium chloride and water (99:1 v/v %) held near room temperature. After primary desiccation, particles are collected, washed, and vacuum dried to remove residual liquid.

Example 34

Human IgG powder is reconstituted in deionized water to a protein concentration of approximately 20 mg/mL. The solution is desalted, after which it is atomized and collected with a stainless steel vessel containing 200 mL of butanol held near 4° C. under conditions of gentle stirring. After primary desiccation, particles are collected, washed, and vacuum dried to remove residual liquid.

Example 35

Human IgG powder is reconstituted in deionized water to a protein concentration of approximately 20 mg/mL. The solution is desalted, after which it is atomized and collected with a stainless steel vessel containing 200 mL of butanol held near 40° C. under conditions of gentle stirring. After primary desiccation, particles are collected, washed, and vacuum dried to remove residual liquid.

Example 36

Human IgG powder is reconstituted in deionized water to a protein concentration of approximately 20 mg/mL. The solution is desalted and a quantity of Tween 20 (5 mg/mL) is added, after which it is atomized and collected with a stainless steel vessel containing 200 mL of butanol held near 40° C. under conditions of gentle stirring. After primary desiccation, particles are collected, washed, and vacuum dried to remove residual liquid.

Example 37

Human IgG powder is reconstituted in deionized water to a protein concentration of approximately 20 mg/mL. The solution is desalted, after which it is atomized and collected with a stainless steel vessel containing 200 mL of a mixture of butanol and Tween 80 (99:1 v/v %) held near 40° C. under conditions of gentle stirring. After primary desiccation, particles are collected, washed, and vacuum dried to remove residual liquid.

Example 38

Human IgG powder was reconstituted in deionized water to a protein concentration of approximately 20 mg/mL. The solution was desalted, after which it was atomized and collected with a stainless steel vessel containing 200 mL of butyl acetate held near 4° C. under conditions of gentle stirring. Approximately 2 mL of feed solution was processed. After primary desiccation, particles were collected, washed, and vacuum dried to remove residual liquid. SEM images revealed identifiable particulate matter (FIGS. 26A-26C).

Example 39

Human IgG powder was reconstituted in deionized water to a protein concentration of approximately 20 mg/mL. The solution was desalted, after which it was atomized and collected with a stainless steel vessel containing 200 mL of butyl acetate held near 40° C. under conditions of gentle stirring. Approximately 2 mL of feed solution was processed. After primary desiccation, particles were collected, washed, and vacuum dried to remove residual liquid. SEM images revealed identifiable particulate matter (FIGS. 27A-27B).

Example 40

Human IgG powder was reconstituted in deionized water to a protein concentration of approximately 20 mg/mL. The solution was desalted and a quantity of Tween 20 (5 mg/mL) was added, after which it was atomized and collected with a stainless steel vessel containing 200 mL of butyl acetate held near 40° C. under conditions of gentle stirring. Approximately 2 mL of feed solution was processed. After primary desiccation, particles were collected, washed, and vacuum dried to remove residual liquid. SEM images revealed identifiable particulate matter (FIGS. 28A-28B).

Example 41

Human IgG powder was reconstituted in deionized water to a protein concentration of approximately 20 mg/mL. The solution was desalted, after which it was atomized and collected with a stainless steel vessel containing 200 mL of a mixture of butyl acetate and Tween 80 (99:1 v/v %) held near 40° C. under conditions of gentle stirring. After primary desiccation, particles were collected, washed, and vacuum dried to remove residual liquid.

Example 42

Human IgG powder is reconstituted in deionized water to a protein concentration of approximately 20 mg/mL. The solution is desalted, after which it is atomized and collected with a stainless steel vessel containing 200 mL of an aqueous solution of PEG 3350 (40 wt %) held near 4° C. under conditions of gentle stirring. After primary desiccation, particles are collected, washed, and vacuum dried to remove residual liquid.

Example 43

Human IgG powder is reconstituted in deionized water to a protein concentration of approximately 20 mg/mL. The solution is desalted, after which it is atomized and collected with a stainless steel vessel containing 200 mL of an aqueous solution of PEG 3350 (40 wt %) held near 40° C. under conditions of gentle stirring. After primary desiccation, particles are collected, washed, and vacuum dried to remove residual liquid.

Example 44

Human IgG powder is reconstituted in deionized water to a protein concentration of approximately 20 mg/mL. The solution is desalted and a quantity of Tween 20 (5 mg/mL) is added, after which it is atomized and collected with a stainless steel vessel containing 200 mL of an aqueous solution of PEG 3350 (40 wt %) held near 40° C. under conditions of gentle stirring. After primary desiccation, particles are collected, washed, and vacuum dried to remove residual liquid.

Example 45

Human IgG powder is reconstituted in deionized water to a protein concentration of approximately 20 mg/mL. The solution is desalted, after which it is atomized and collected with a stainless steel vessel containing 200 mL of an aqueous solution of PEG 3350 (40 wt %) and Tween 80 (1 wt %) held near 40° C. under conditions of gentle stirring. After primary desiccation, particles are collected, washed, and vacuum dried to remove residual liquid.

Example 46

Human IgG powder is reconstituted in deionized water to a protein concentration of approximately 20 mg/mL. The solution is desalted, after which it is atomized and collected with a stainless steel vessel containing 200 mL of choline taurinate held near 4° C. under conditions of gentle stirring. After primary desiccation, particles are collected, washed, and vacuum dried to remove residual liquid.

Example 47

Human IgG powder is reconstituted in deionized water to a protein concentration of approximately 20 mg/mL. The solution is desalted, after which it is atomized and collected with a stainless steel vessel containing 200 mL of choline taurinate held near 40° C. under conditions of gentle stirring. After primary desiccation, particles are collected, washed, and vacuum dried to remove residual liquid.

Example 48

Human IgG powder is reconstituted in deionized water to a protein concentration of approximately 20 mg/mL. The solution is desalted and a quantity of Tween 20 (5 mg/mL) is added, after which it is atomized and collected with a stainless steel vessel containing 200 mL of choline taurinate held near 40° C. under conditions of gentle stirring. After primary desiccation, particles are collected, washed, and vacuum dried to remove residual liquid.

Example 49

Human IgG powder is reconstituted in deionized water to a protein concentration of approximately 20 mg/mL. The solution is desalted, after which it is atomized and collected with a stainless steel vessel containing 200 mL of a mixture of choline taurinate and Tween 80 (99:1 v/v %) held near 40° C. under conditions of gentle stirring. After primary desiccation, particles are collected, washed, and vacuum dried to remove residual liquid.

Example 50

Figure 29A:
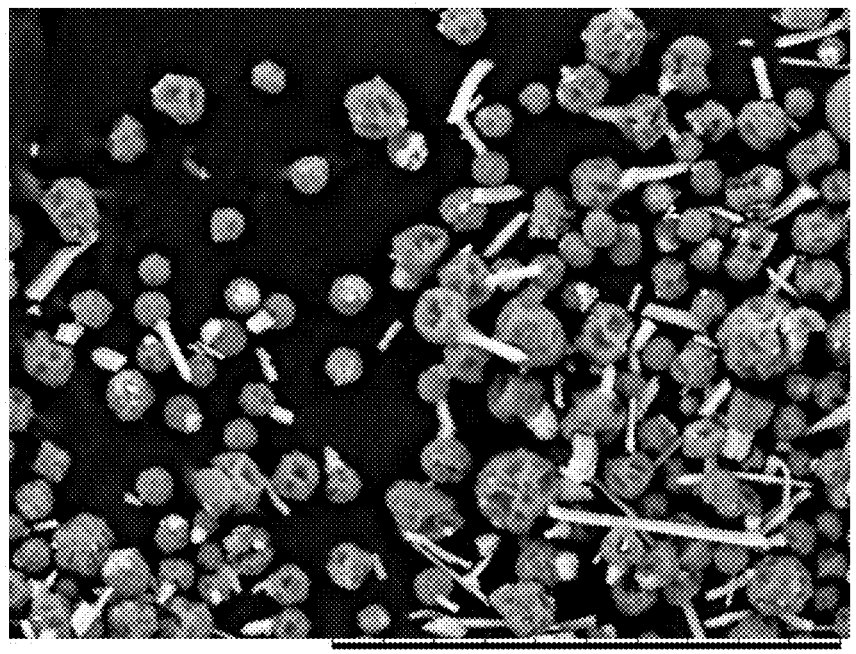
Figure 29B:
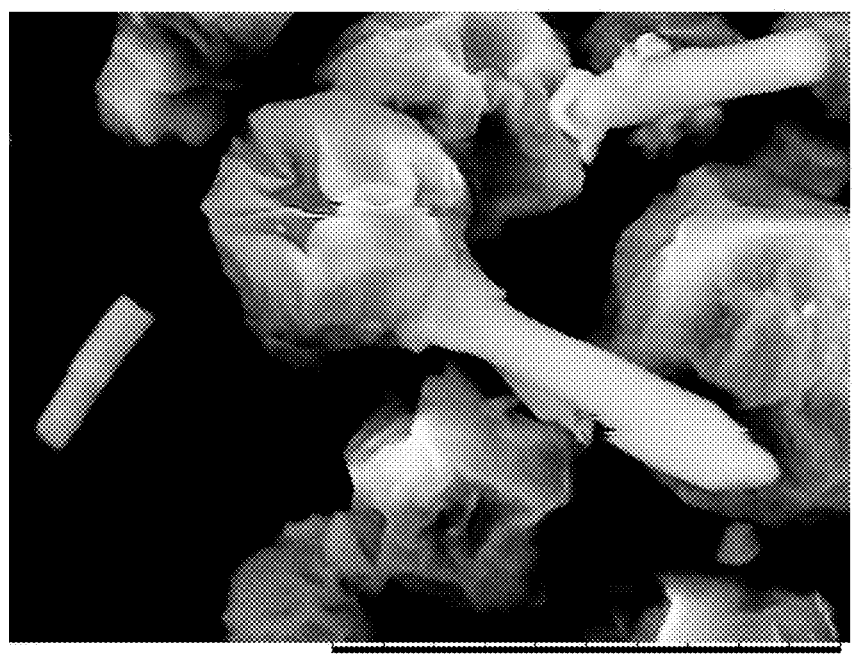

Bovine IgG was thawed without desalting or otherwise modifying the solution. The solution was atomized and collected with a stainless steel vessel containing 400 mL of 2-ethylhexyl acetate held near 30° C. in the absence of stirring, i.e., such that bulk flow did not prevail in the second liquid. Approximately 2 mL of feed solution was processed. After primary desiccation, particles were collected, washed, and vacuum dried to remove residual liquid. SEM images revealed identifiable particulate matter (FIGS. 29A-29B).

Example 51

Human IgG powder is reconstituted in deionized water to a protein concentration of approximately 20 mg/mL. The solution is desalted, after which it is directly atomized in a stainless steel vessel containing 200 mL of butanol, i.e., with the atomizer source immersed in the second liquid, held near room temperature under conditions of gentle stirring. Approximately 2 mL of feed solution is processed, all of which involves generation of drops directly within the butanol. After primary desiccation, particles are collected, washed, and vacuum dried to remove residual liquid.

Example 52

Human IgG powder is reconstituted in deionized water to a protein concentration of approximately 20 mg/mL. The solution is desalted, after which it is directly atomized in a stainless steel vessel containing 200 mL of butanol, i.e., with the atomizer source immersed in the second liquid, held near room temperature under conditions of gentle stirring. No voltage is applied. Approximately 2 mL of feed solution is processed, all of which involves generation of drops directly within the butanol. After primary desiccation, particles are collected, washed, and vacuum dried to remove residual liquid.

Example 53

Figure 30A:
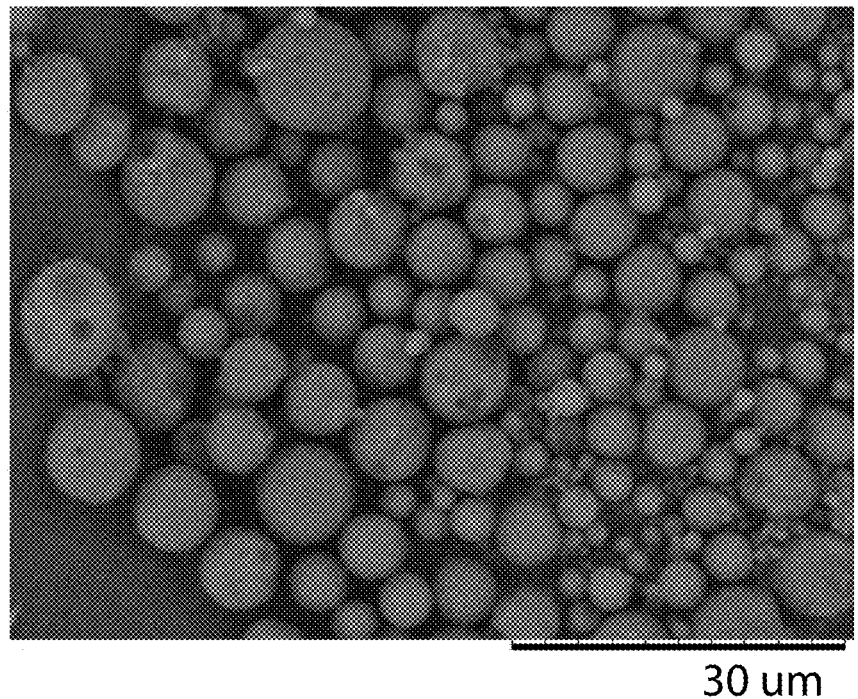
Figure 30B:
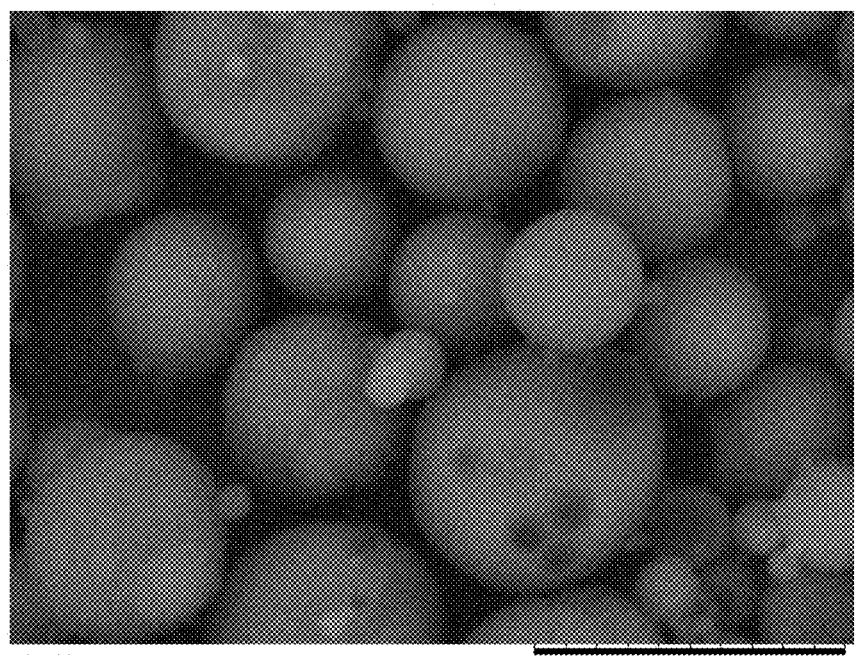

Human IgG powder was reconstituted in deionized water to a protein concentration of approximately 20 mg/mL. The solution was desalted, after which it was directly atomized in a stainless steel vessel containing 200 mL of butyl acetate, i.e., with the atomizer source immersed in the second liquid, held near room temperature under conditions of gentle stirring. Approximately 2 mL of feed solution was processed, all of which involved generation of drops directly within the butyl acetate. After primary desiccation, particles were collected, washed, and vacuum dried to remove residual liquid. SEM images revealed identifiable particulate matter (FIGS. 30A-30B).

Example 54

Figure 31A:
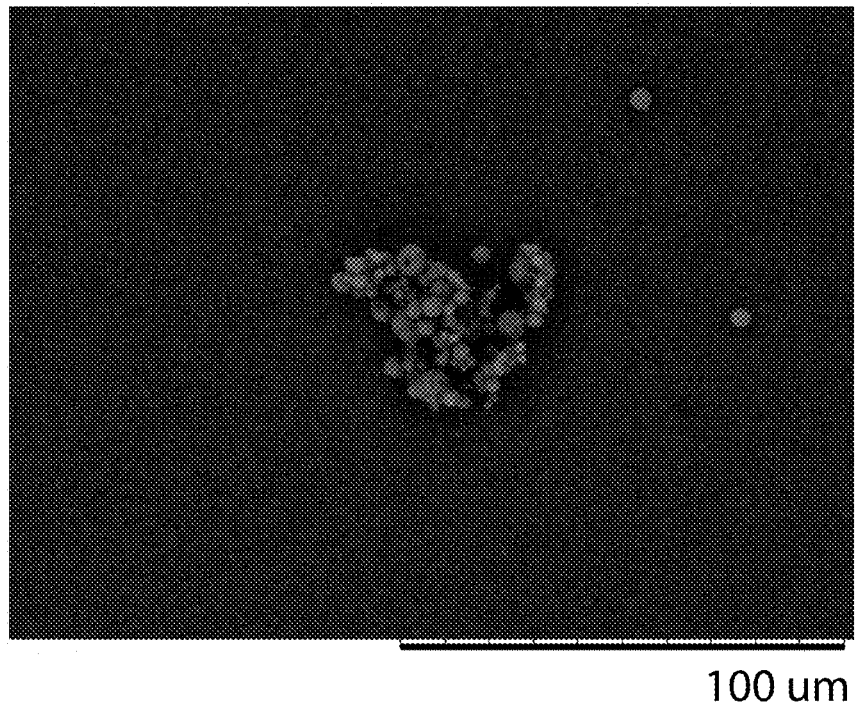
Figure 31B:
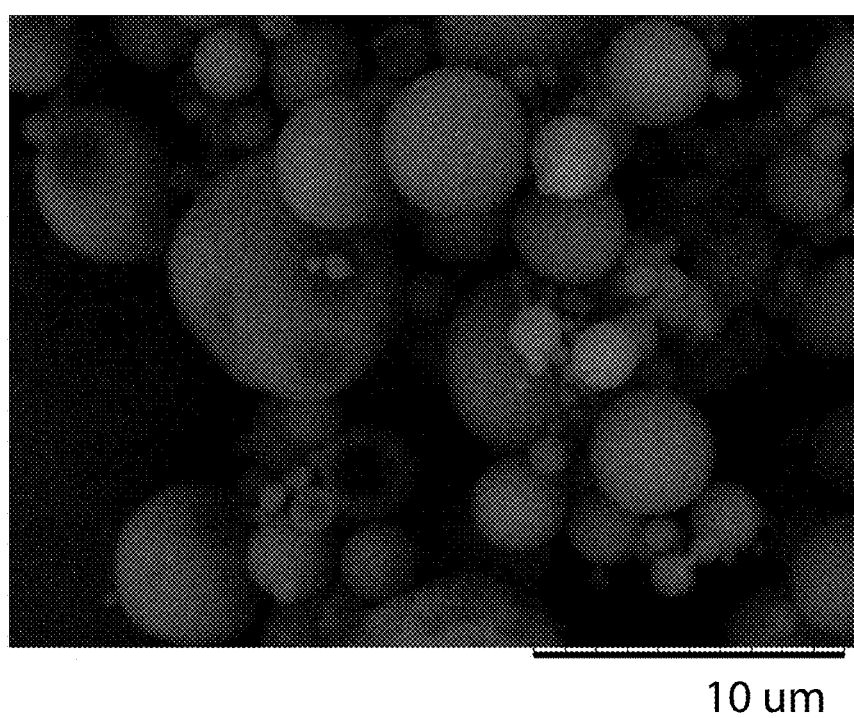
Figure 32A:
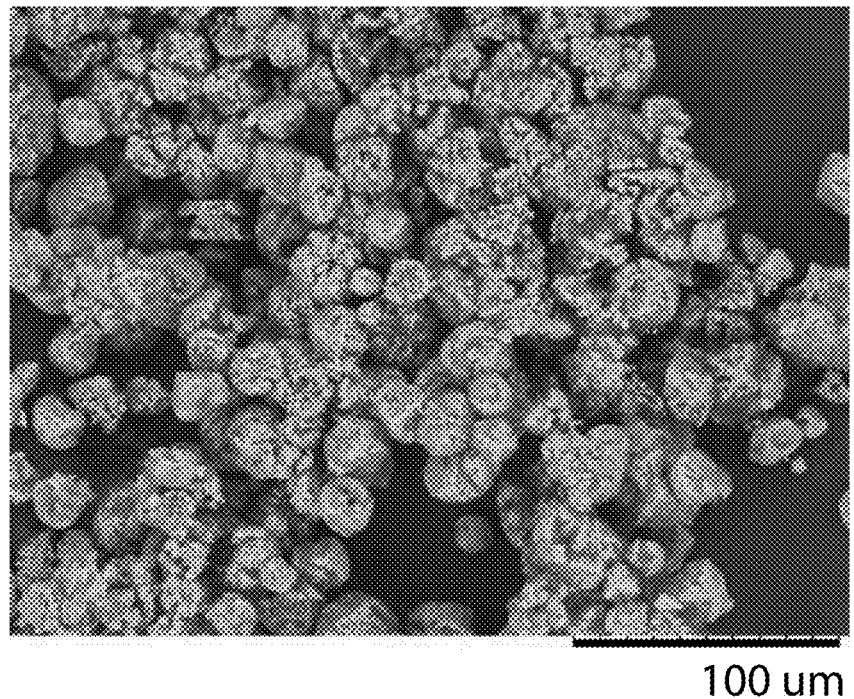
Figure 32B:
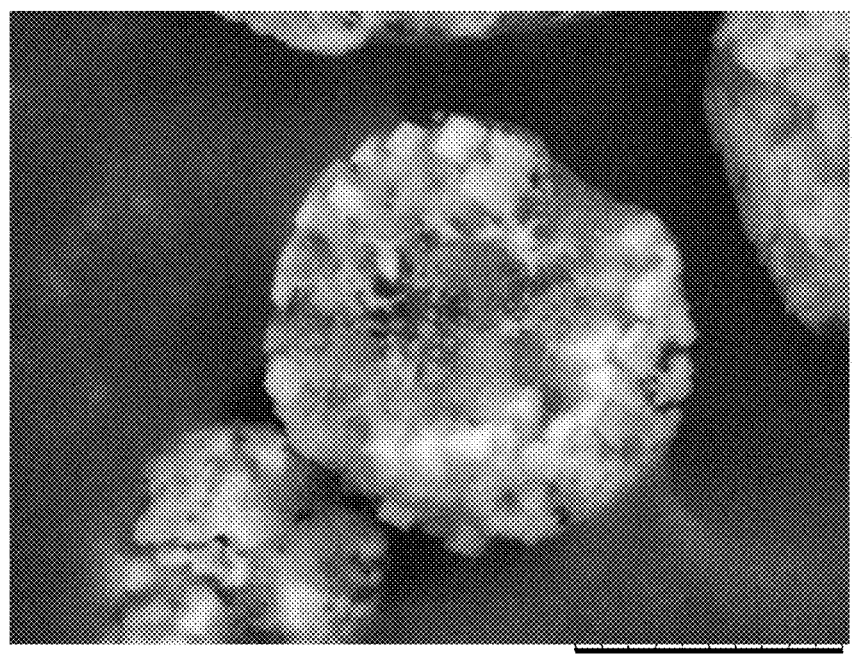
Figure 33:
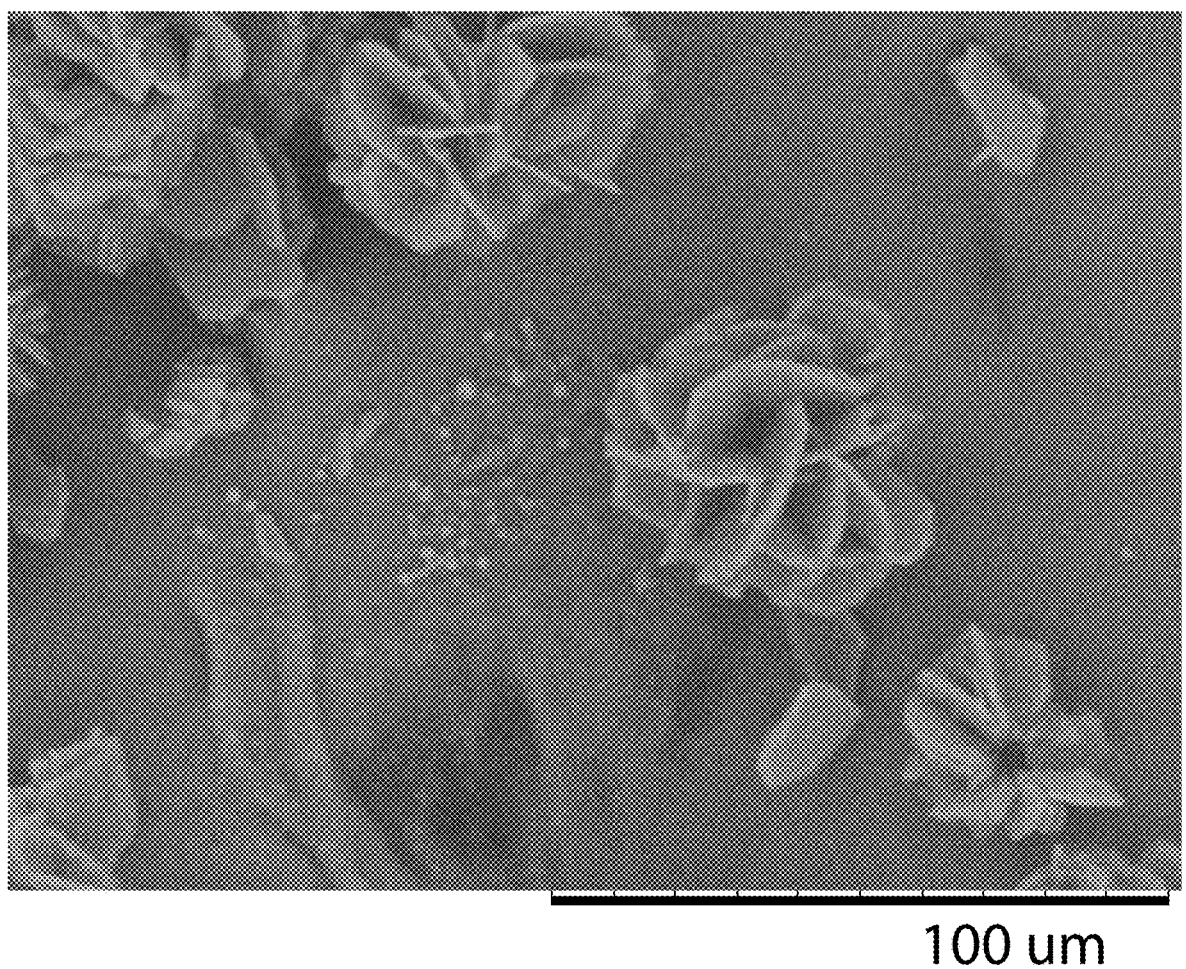
Figure 34:
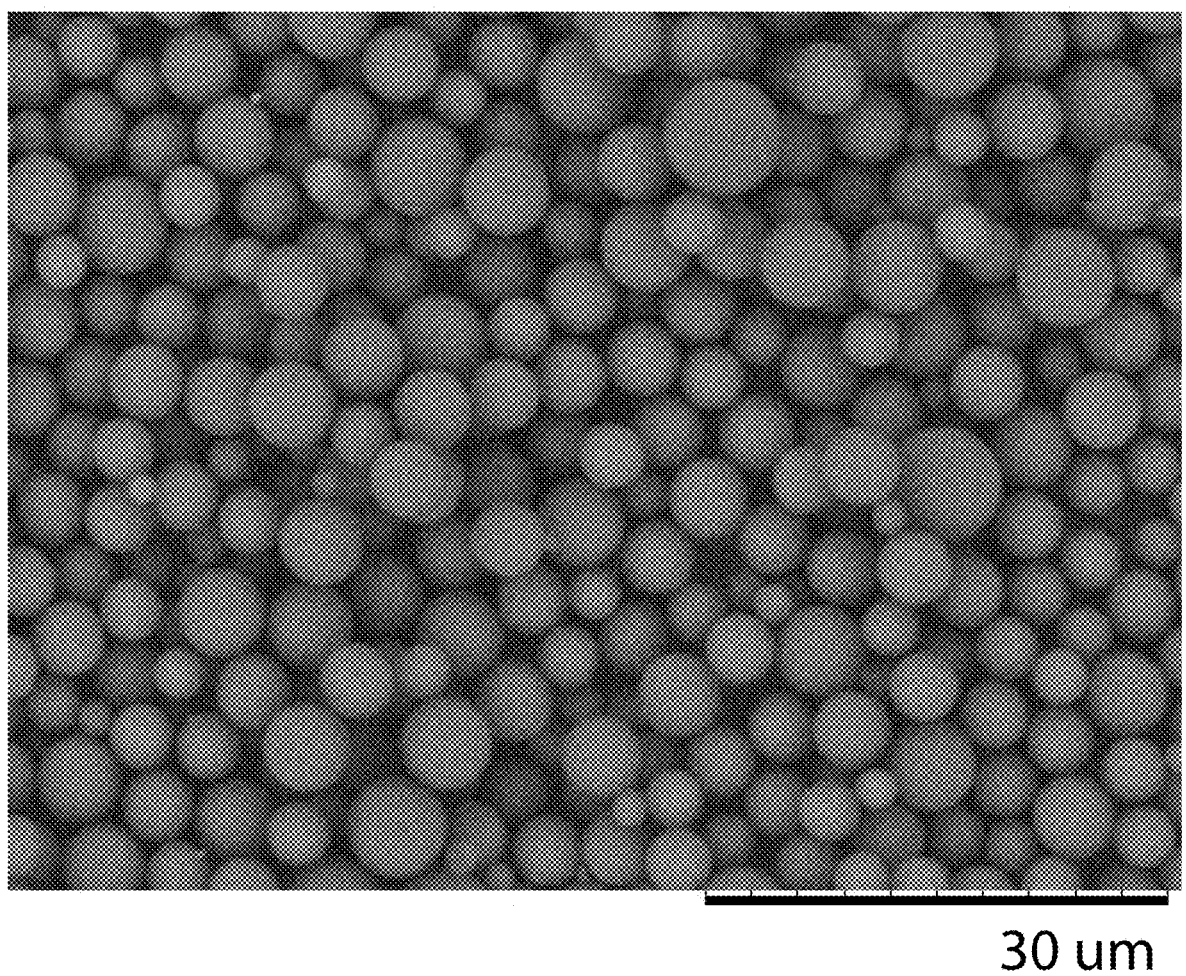

Human IgG powder was reconstituted in deionized water to a protein concentration of approximately 30 mg/mL. The solution was desalted, after which it was directly atomized in a stainless steel vessel containing 350 mL of butyl acetate, i.e., with atomizer source immersed in the second liquid, held near room temperature under conditions of gentle stirring. No voltage was applied. Approximately 1.5 mL of feed solution was processed, all of which involved generation of drops directly within the butyl acetate. After primary desiccation, particles were collected, washed, and vacuum dried to remove residual liquid. SEM images revealed identifiable particulate matter (FIGS. 31A-31B).

Example 55

Human IgG powder is reconstituted in deionized water to a protein concentration of approximately 20 mg/mL. The solution is desalted, after which it is directly atomized in a stainless steel vessel containing 200 mL of an aqueous solution of PEG 3350 (40 wt %), i.e., with the atomizer source immersed in the second liquid, held near room temperature under conditions of gentle stirring. Approximately 2 mL of feed solution is processed, all of which involves generation of drops directly within the PEG solution. After primary desiccation, particles are collected, washed, and vacuum dried to remove residual liquid.

Example 56

Human IgG powder is reconstituted in deionized water to a protein concentration of approximately 20 mg/mL. The solution is desalted, after which it is directly atomized in a stainless steel vessel containing 200 mL of an aqueous solution of PEG3350 (40 wt %), i.e., with the atomizer source immersed in the second liquid, held near room temperature under conditions of gentle stirring. No voltage is applied. Approximately 2 mL of feed solution is processed, all of which involves generation of drops directly within the PEG solution. After primary desiccation, particles are collected, washed, and vacuum dried to remove residual liquid.

Example 57

Human IgG powder is reconstituted in deionized water to a protein concentration of approximately 20 mg/mL. The solution is desalted, after which it is directly atomized in a stainless steel vessel containing 200 mL of choline acetate, i.e., with the atomizer source immersed in the second liquid, held near room temperature under conditions of gentle stirring. Approximately 2 mL of feed solution is processed, all of which involves generation of drops directly within the ionic liquid. After primary desiccation, particles are collected, washed, and vacuum dried to remove residual liquid.

Example 58

Human IgG powder is reconstituted in deionized water to a protein concentration of approximately 20 mg/mL. The solution is desalted, after which it is directly atomized in a stainless steel vessel containing 200 mL of choline acetate, i.e., with the atomizer source immersed in the second liquid, held near room temperature under conditions of gentle stirring. No voltage is applied. Approximately 2 mL of feed solution is processed, all of which involves generation of drops directly within the ionic liquid. After primary desiccation, particles are collected, washed, and vacuum dried to remove residual liquid.

Example 59

A 2 mL solution of ibuprofen in butyl acetate was prepared at a concentration of 58 mg/mL. The solution was atomized and collected with a stainless steel vessel containing 200 mL of deionized water held near 40° C. under conditions of gentle stirring. After primary desiccation, particles were collected, washed, and vacuum dried to remove residual liquid.

Example 60

Human IgG powder is reconstituted in deionized water to a protein concentration of approximately 35 mg/mL. The solution is atomized and collected with a stainless steel vessel containing 400 mL of cottonseed oil held near room temperature under conditions of gentle stirring. Approximately 3 mL of feed solution is processed, resulting in an ensemble of wet (substantially hydrated) drops within the oil. Since primary desiccation occurs over a long time scale in cottonseed oil, a 400 mL quantity of ethanol is added to the stirring vessel at a rate of 1 mL/min to facilitate primary desiccation at a defined rate. After primary desiccation, particles are collected, washed, and vacuum dried to remove residual liquid.

Example 61

Human IgG powder is reconstituted in deionized water to a protein concentration of approximately 35 mg/mL. The solution is atomized and collected with a stainless steel vessel containing 400 mL of cottonseed oil held near room temperature under conditions of gentle stirring. Approximately 3 mL of feed solution is processed, resulting in an ensemble of wet (substantially hydrated) drops within the oil. Since primary desiccation occurs over a long time scale in cottonseed oil, a 400 mL quantity of 1-butyl-3-methylimidazolium chloride is added to the stirring vessel at a rate of 1 mL/min to facilitate primary desiccation at a defined rate. After primary desiccation, particles are collected, washed, and vacuum dried to remove residual liquid.

Example 62

Human IgG powder is reconstituted in deionized water to a protein concentration of approximately 50 mg/mL. The solution is desalted, after which it was atomized and collected by a vessel containing 200 mL of PEG 3350 solution (40 wt %) held near 40° C. under conditions of gentle stirring. After primary desiccation, particles are collected and washed with ethanol such that PEG 3350 is removed without solubilizing the proteinaceous particles. The particles are vacuum dried thereafter to remove residual liquid.

Example 63

Human IgG protein is reconstituted in deionized water to a protein concentration of approximately 50 mg/mL without desalting or otherwise modifying the solution. The solution is atomized in a microfluidic flow focusing chip with the assistance of a continuous phase consisting of neat cottonseed oil. The proteinaceous dispersed phase and cottonseed oil are driven with syringe pumps at rates from 0.1-10 mL/h and 1-50 mL/h, respectively, to form droplets of various sizes. The output of the microfluidic flow focusing chip is collected with a vessel containing 400 mL of isopropanol held near room temperature under conditions of gentle stirring. After primary desiccation, particles are collected, washed, and vacuum dried to remove residual liquid.

Example 64

Human IgG protein is reconstituted in deionized water to a protein concentration of approximately 50 mg/mL without desalting or otherwise modifying the solution. The solution is atomized in a microfluidic flow focusing chip with the assistance of a continuous phase consisting of neat cottonseed oil. The proteinaceous dispersed phase and cottonseed oil are driven with syringe pumps at rates from 0.1-10 mL/h and 1-50 mL/h, respectively, to form droplets of various sizes. The output of the microfluidic flow focusing chip is collected with a vessel containing 400 mL of choline taurinate held near room temperature under conditions of gentle stirring. After primary desiccation, particles are collected, washed, and vacuum dried to remove residual liquid.

Example 65

A suspension of titanium dioxide ($TiO_2$) powder is prepared by mixing 0.05 g of $TiO_2$ with 100 mL deionized water. After an hour of sonication, the suspension is atomized and collected with a stainless steel vessel containing 400 mL of a mixture comprising toluene and acetone (25/75 v/v %) held near room temperature. After primary desiccation, particles are collected, washed, and vacuum dried to remove residual liquid.

Example 66

A suspension of titanium dioxide ($TiO_2$) powder is prepared by mixing 0.05 g of $TiO_2$ with 100 mL deionized water. After an hour of sonication, the suspension is atomized and collected with a stainless steel vessel containing 400 mL of 1-butyl-3-methylimidazolium chloride held near room temperature. After primary desiccation, particles are collected, washed, and vacuum dried to remove residual liquid.

Example 67

A 5 mg quantity of porcine intestinal mucins was reconstituted in salt solution. The solution was processed according to one of the preceding examples. After primary desiccation, particles were collected, washed, and vacuum dried to remove residual liquid. SEM images revealed identifiable particulate matter (FIGS. 32A-32B).

Example 68

A 0.25 mL quantity of double stranded DNA (1.95 mg/mL) was mixed with 1.5 mL histidine solution (32 mg/mL). The solution was processed according to one of the preceding examples. After primary desiccation, particles were collected, washed, and vacuum dried to remove residual liquid. SEM images revealed identifiable particulate matter (FIG. 33).

Example 69

A solution containing mAbl (20 mg/mL), a buffer (4 mg/mL), a surfactant (1 mg/mL), and salt (0.7 mg/mL) was processed according to one of the preceding examples. The solution was atomized and collected with a vessel containing a second liquid. After primary desiccation, particles were collected, washed, and lyophilized to remove residual liquid. SEM images revealed identifiable particulate matter (FIG. 34). The average particle size was 4.2 μm with a $d_{90}$ of 5.2 μm. The density and residual moisture content were approximately 1.3 g/$cm^3$ and <2 wt %, respectively. Reconstitution of a freshly prepared batch of particles demonstrated that the percentage of monomers in the reconstituted material were within 0.1% of the percentage of monomers in the feed solution, which is within the error of the HPLC-SEC instrument. A separate batch of particles was stored for 7 days under accelerated conditions (40 ° C.). After storage, mAb 1 was reconstituted and various structural and functional assays were performed. The percentage of monomers in the reconstituted material was within 0.6% of the percentage of monomers in feed solution. The percentages of acidic, main, and basic charge variants were within 0.5%, 1%, and 0.6% of the percentages of the corresponding species in the feed solution. Flow cytometry was performed and EC50 values were calculated to compare mAb1 feed solution to stored particles, which resulted in a p-value of 0.1271 (no significant difference). Antibody dependent cell-mediated cytotoxicity was performed and EC50 values were calculated to compare mAb 1 feed solution to stored particles, which resulted in a p-value of 0.1271 (no significant difference).

Example 70

Figure 35:
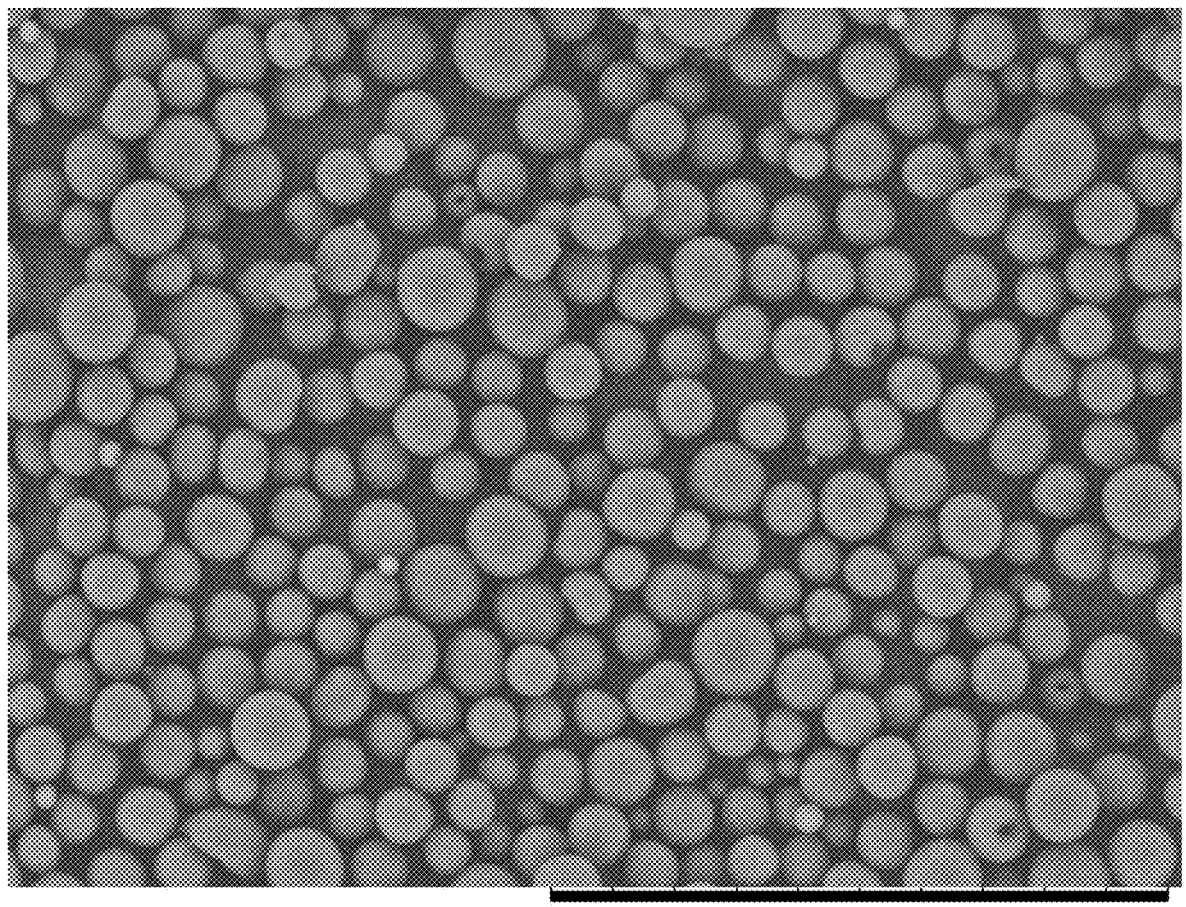
Figure 36:
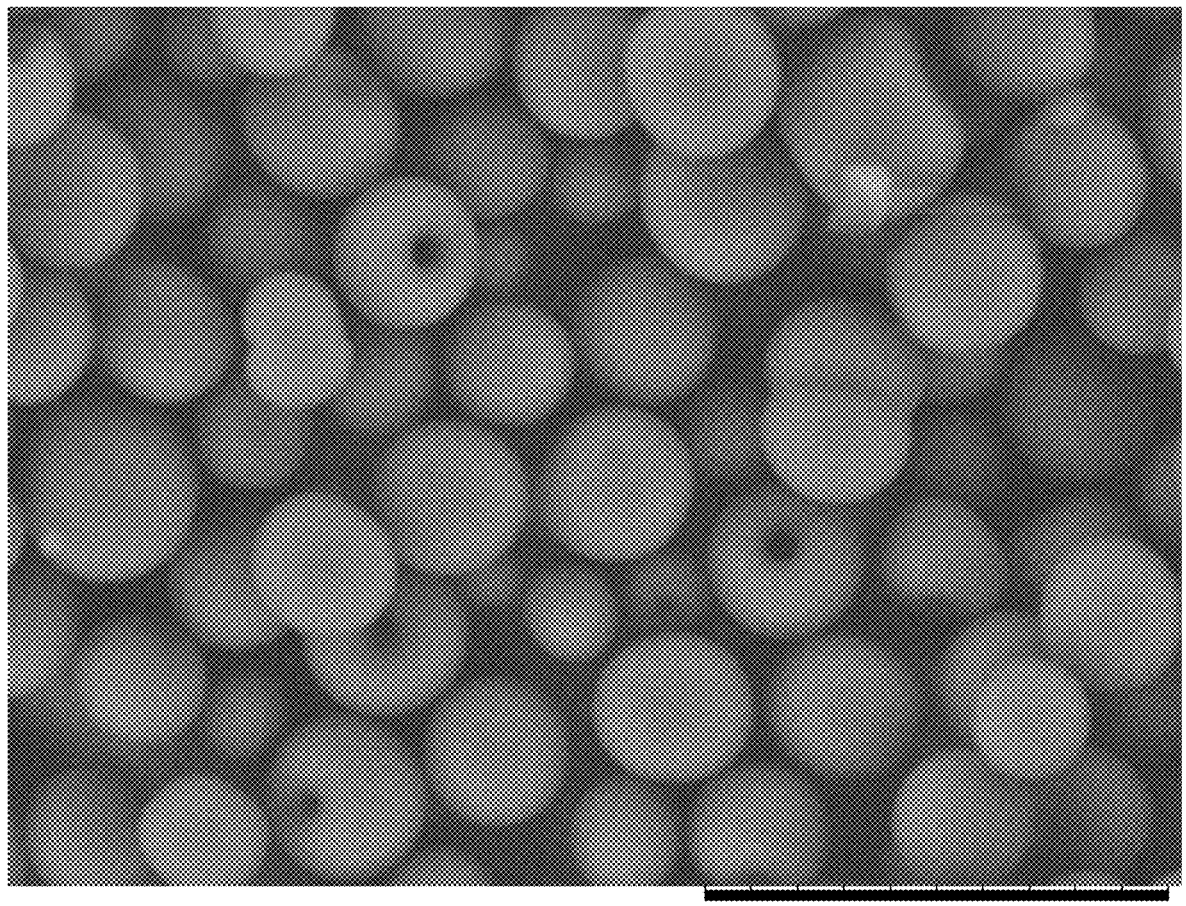
Figure 37:
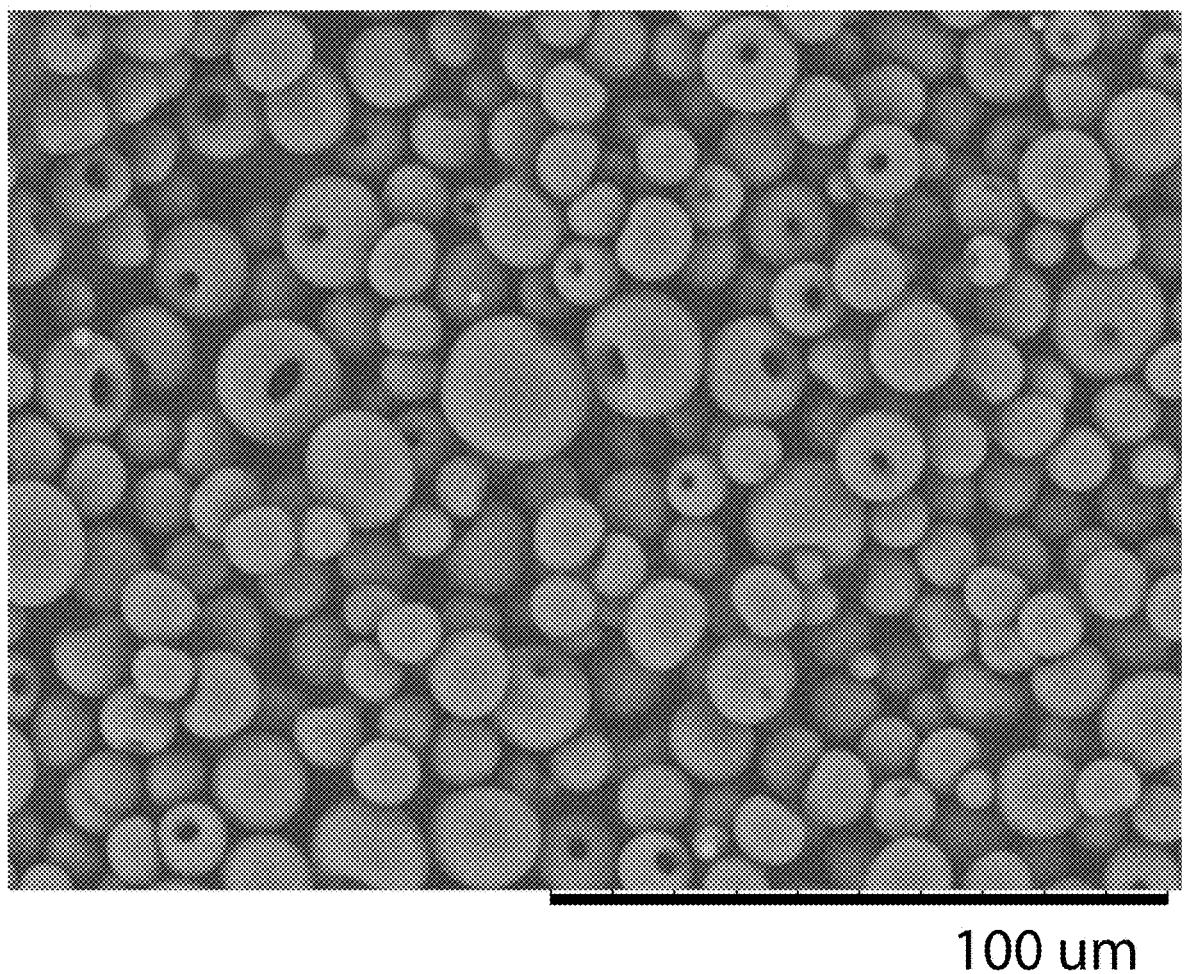
Figure 38:
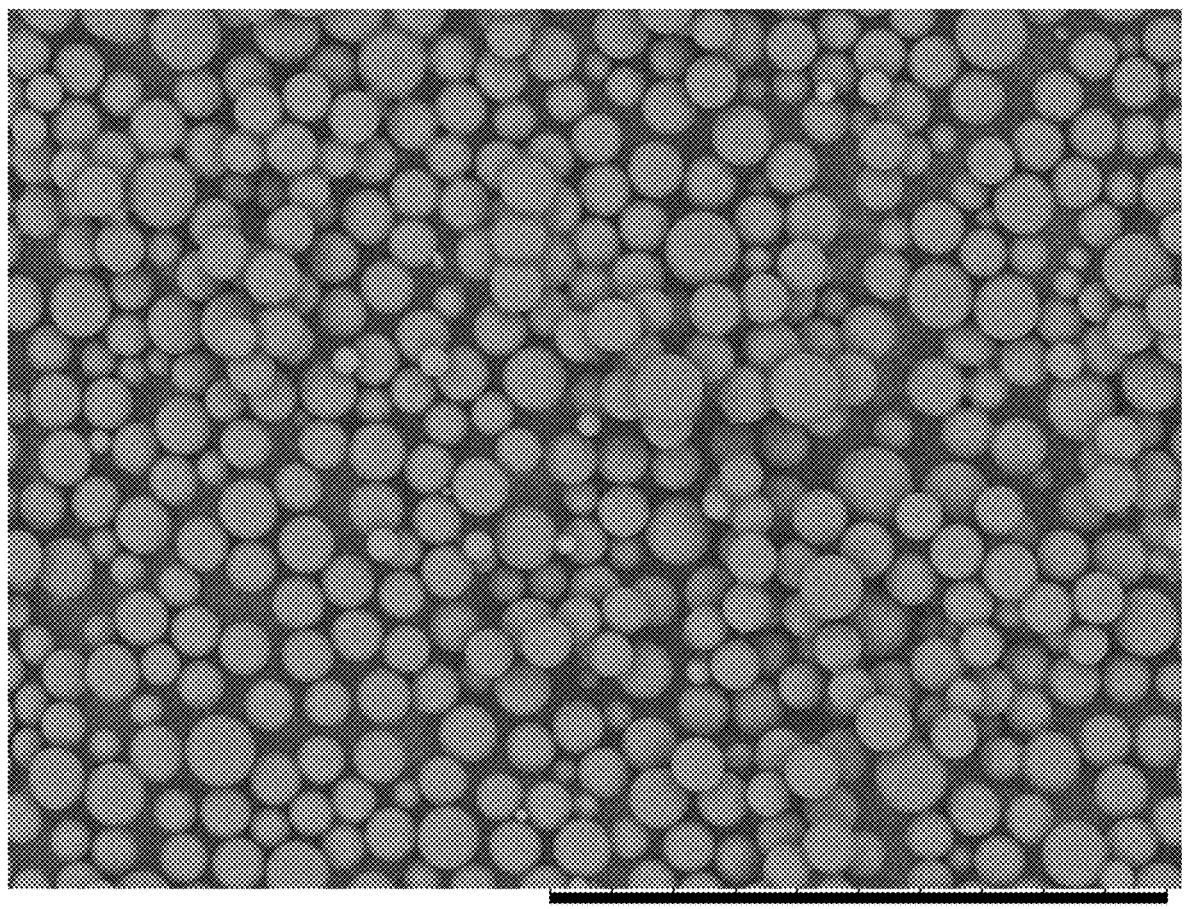
Figure 39:
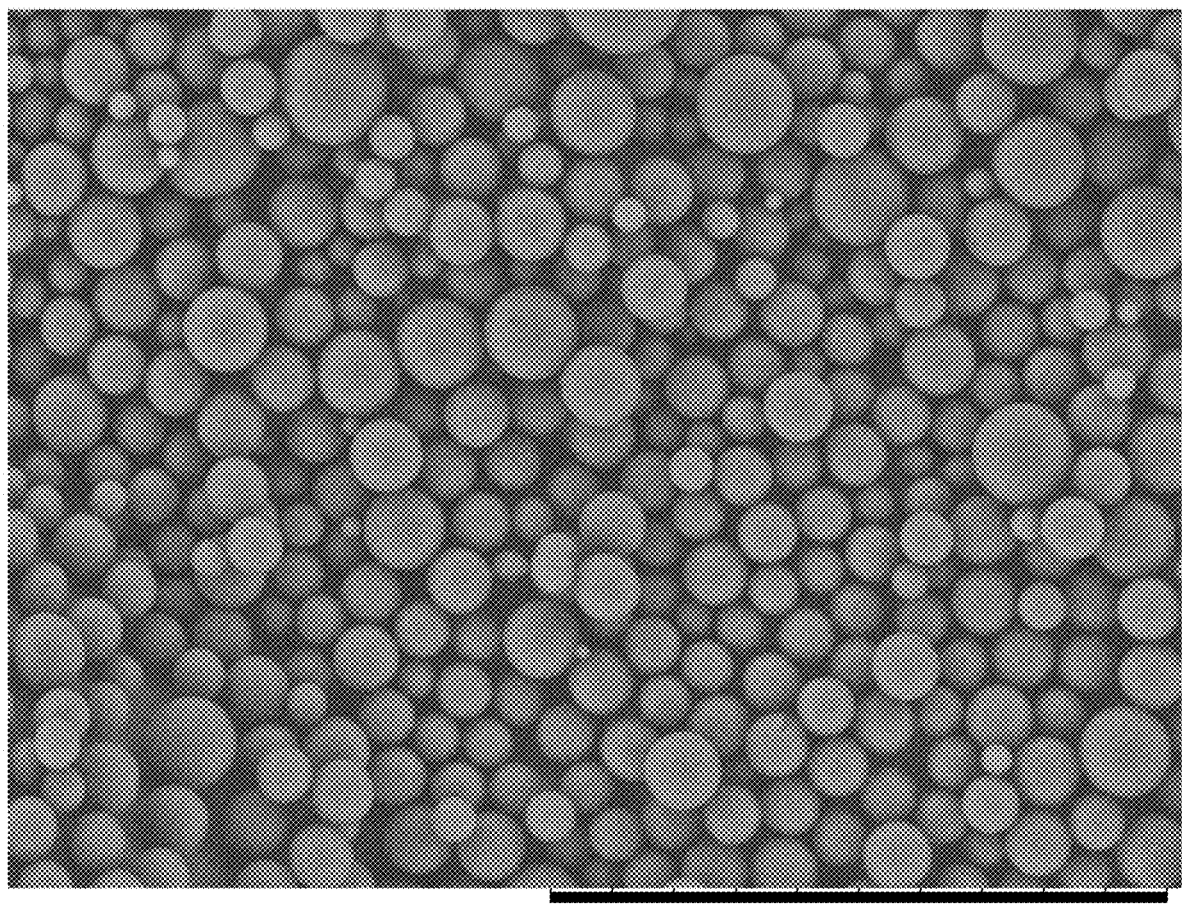
Figure 40:
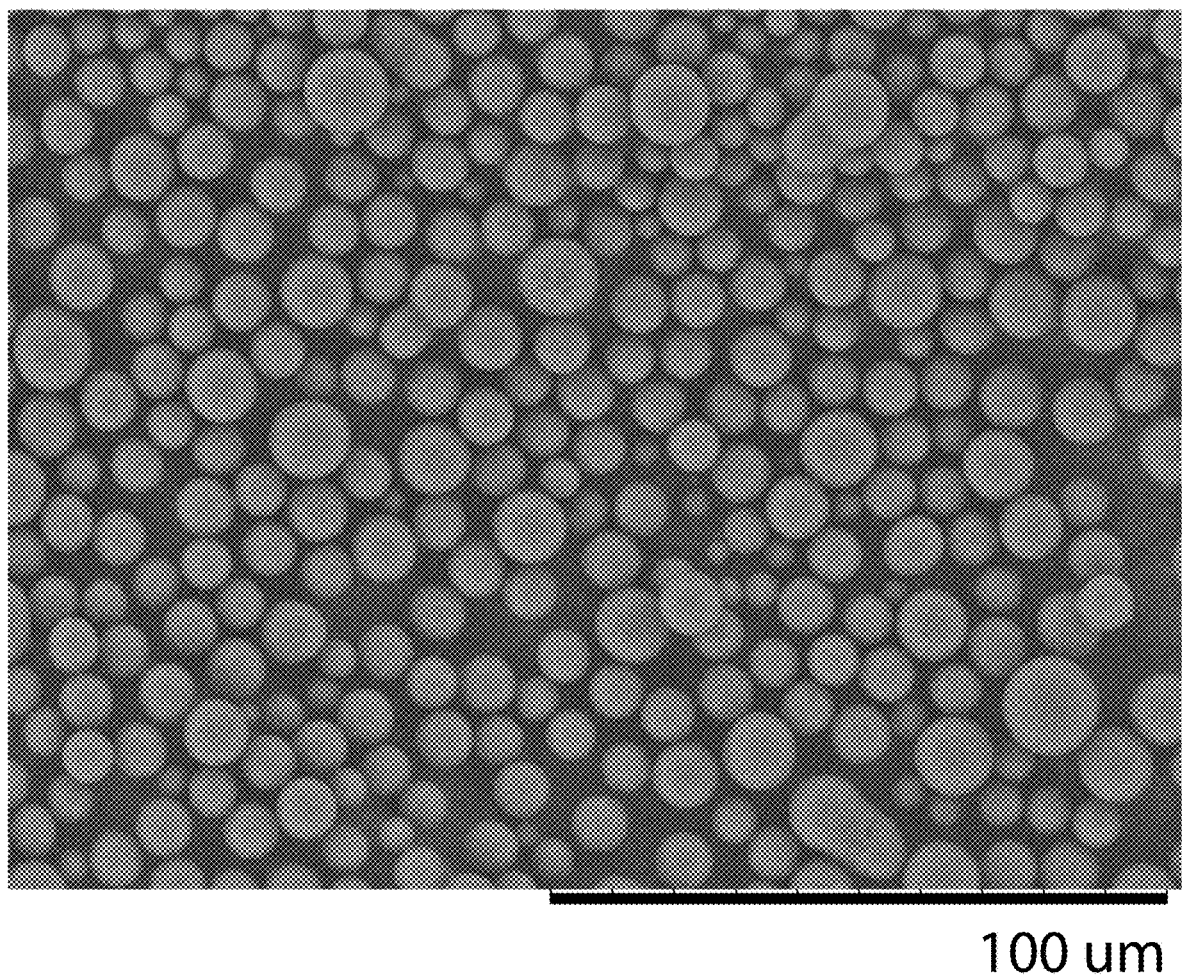

A solution containing mAb2 (100 mg/mL), a sugar (9.5 mg/mL), and buffer (35.7 mg/mL) was processed according to one of the preceding examples. The solution was atomized and collected with a vessel containing a second liquid. After primary desiccation, particles were collected, washed, and lyophilized to remove residual liquid. SEM analysis revealed identifiable particulate matter (FIG. 35). The mean particle size was 8.3 μm with a dispersity of 0.27. The particles were reconstituted in clean, deionized water to a mAb2 concentration of approximately 3-5 mg/mL. SEC analysis of the reconstituted material indicated aggregate, monomer, and fragment percentages of 0.207%, 99.793%, and 0%, respectively. The feed solution exhibited 0.498%, 99.502%, and 0%, respectively. SvP analysis of the reconstituted material indicated 19,350 SvPs>1 μm, 110 SvPs>10 μm, and 0 SvPs>25 μm. A control sample comprising a proportional volume of diluent exhibited 2,068 SvPs>1 μm, 21 SvPs>10 μm, and 0 SvPs>25 μm. The aqueous mAb, at approximately 7-8 mg/mL, exhibited 6760 SvPs>1 μm, 21 SvPs>10 μm, and 0 SvPs>25 μm.

Example 71

A solution containing mAb3 (100 mg/mL), a sugar (9.5 mg/mL), and buffer (35.7 mg/mL) was processed according to one of the preceding examples. The solution was atomized and collected with a vessel containing a second liquid. After primary desiccation, particles were collected, washed, and lyophilized to remove residual liquid. SEM analysis revealed identifiable particulate matter (FIG. 36). The mean particle size was 8.33 μm with a dispersity of 0.24. The particles were reconstituted in clean, deionized water to a mAb2 concentration of approximately 7-10 mg/mL. SEC analysis of the reconstituted material indicated aggregate, monomer, and fragment percentages of 5.599%, 94.121%, and 0.280%, respectively. The feed solution exhibited 5.251%, 94.298%, and 0.451%, respectively. SvP analysis of the reconstituted material indicated 39,930 SvPs>1 μm, 426 SvPs>10 μm, and 0 SvPs>25 μm. A control sample comprising a proportional volume of diluent exhibited 2,068 SvPs>1 μm, 21 SvPs>10 p.m, and 0 SvPs>25 μm. The aqueous mAb, at approximately 6-8 mg/mL, exhibited 4632 SvPs >1 μm, 110 SvPs>10 μm, and 0 SvPs>25 μm.

Example 72

A solution containing mAb4 (150 mg/mL), a sugar (90 mg/mL), and buffer (1.8 mg/mL) was processed according to one of the preceding examples. The solution was atomized and collected with a vessel containing a second liquid. After primary desiccation, particles were collected, washed, and lyophilized to remove residual liquid. SEM analysis revealed identifiable particulate matter (FIG. 37). The mean particle size was 11 μm with a dispersity of 0.30. The particles were reconstituted in clean, deionized water to a mAb2 concentration of approximately 6-8 mg/mL. SEC analysis of the reconstituted material indicated aggregate, monomer, and fragment percentages of 0.021%, 99.779%, and 0%, respectively. The feed solution exhibited 0.572%, 99.428%, and 0%, respectively. SvP analysis of the reconstituted material indicated 38,272 SvPs>1 μm, 309 SvPs>10 μm, and 0 SvPs>25 μm. A control sample comprising a proportional volume of diluent exhibited 2,068 SvPs>1 μm, 21 SvPs>10 μm, and 0 SvPs>25 μm. The aqueous mAb, at approximately 11-13 mg/mL, exhibited 2679 SvPs>1 μm, 21 SvPs >10 μm, and 0 SvPs>25 μm.

Example 73

A solution containing mAb2 (100 mg/mL), a sugar (9.5 mg/mL), and buffer (35.7 mg/mL) was processed according to one of the preceding examples. The solution was atomized and collected with a vessel containing a second liquid. After primary desiccation, particles were collected, washed, and lyophilized to remove residual liquid. SEM analysis revealed identifiable particulate matter (FIG. 38). The mean particle size was 7.06 μm with a dispersity of 0.26. The particles were reconstituted in clean, deionized water to a mAb2 concentration of approximately 3-5 mg/mL. SEC analysis of the reconstituted material indicated aggregate, monomer, and fragment percentages of 0.230%, 99.692%, and 0.079%, respectively. The feed solution exhibited 0.498%, 99.502%, and 0%, respectively. SvP analysis of the reconstituted material indicated 5688 SvPs>1 μm, 72 SvPs>10 μm, and 0 SvPs>25 μm. A control sample comprising a proportional volume of diluent exhibited 2,068 SvPs>1 μm, 21 SvPs>10 μm, and 0 SvPs>25 μm. The aqueous mAb, at approximately 7-8 mg/mL, exhibited 6760 SvPs>1 μm, 21 SvPs>10 μm, and 0 SvPs>25 μm.

Example 74

A solution containing mAb3 (100 mg/mL), a sugar (9.5 mg/mL), and buffer (35.7 mg/mL) was processed according to one of the preceding examples. The solution was atomized and collected with a vessel containing a second liquid. After primary desiccation, particles were collected, washed, and lyophilized to remove residual liquid. SEM analysis revealed identifiable particulate matter (FIG. 39). The mean particle size was 7.86 μm with a dispersity of 0.25. The particles were reconstituted in clean, deionized water to a mAb2 concentration of approximately 7-10 mg/mL. SEC analysis of the reconstituted material indicated aggregate, monomer, and fragment percentages of 5.368%, 94.354%, and 0.278%, respectively. The feed solution exhibited 5.251%, 94.298%, and 0.451%, respectively. SvP analysis of the reconstituted material indicated 32,530 SvPs>1 μm, 320 SvPs>10 μm, and 0 SvPs>25 μm. A control sample comprising a proportional volume of diluent exhibited 2,068 SvPs>1 μm, 21 SvPs>10 μm, and 0 SvPs>25 μm. The aqueous mAb, at approximately 6-8 mg/mL, exhibited 4632 SvPs>1 μm, 110 SvPs>10 μm, and 0 SvPs>25 μm.

Example 75

A solution containing mAb4 (150 mg/mL), a sugar (90 mg/mL), and buffer (1.8 mg/mL) was processed according to one of the preceding examples. The solution was atomized and collected with a vessel containing a second liquid. After primary desiccation, particles were collected, washed, and lyophilized to remove residual liquid. SEM analysis revealed identifiable particulate matter (FIG. 40). The mean particle size was 8.23 μm with a dispersity of 0.26. The particles were reconstituted in clean, deionized water to a mAb2 concentration of approximately 6-8 mg/mL. SEC analysis of the reconstituted material indicated aggregate, monomer, and fragment percentages of 0.274%, 99.656%, and 0.070%, respectively. The feed solution exhibited 0.572%, 99.428%, and 0%, respectively. SvP analysis of the reconstituted material indicated 39,193 SvPs>1 μm, 712 SvPs>10 μm, and 0 SvPs>25 μm. A control sample was generated by processing an aqueous feed stock, without any solute, in the same manner as the particles. A control sample comprising a proportional volume of diluent exhibited 2,068 SvPs>1 μm, 21 SvPs>10 μm, and 0 SvPs>25 μm. The aqueous mAb, at approximately 11-13 mg/mL, exhibited 2679 SvPs>1 μm, 21 SvPs>10 μm, and 0 SvPs>25 μm.

Discussion

As demonstrated in the exemplary material, particle morphology was manipulated variously and extensively by modifying the composition and properties of the first liquid and the second liquid. In the case of particle formulations containing monoclonal antibodies (Examples 38-44), physiochemical analyses indicated agent activity was substantially preserved immediately following processing and on stability under thermal stress (7 days at 40° C.).

Other embodiments are in the claims.

What is claimed is:

1. A composition comprising particles, wherein a plurality of particles are round particles having a sphericity greater than 0.9, wherein the plurality of particles comprise an excipient and a therapeutic agent, wherein a mass loading of the therapeutic agent in the plurality of particles is between 50% and 100%, wherein the therapeutic agent is a protein, peptide, or nucleic acid, and wherein the excipient is a salt, an amino acid, a surfactant, or a carbohydrate.

2. The composition of claim 1, wherein the composition has a concentration of Subvisible Particles of less than 10,000,000 per mL, wherein the Subvisible Particles are insoluble upon reconstitution in water.

3. The composition of claim 2, wherein the Subvisible Particles have a characteristic size greater than or equal to 10 um and are at a concentration of less than 6,000 per mL.

4. The composition of claim 2, wherein the Subvisible Particles have a characteristic size greater than or equal to 25 μm and are at a concentration of less than 600 per mL.

5. The composition of claim 1, wherein the therapeutic agent has 0.5 to 1.0 activity per unit.

6. The composition of claim 1, wherein the particles have diameters from 0.1 to 1000 μm.

7. The composition of claim 1, wherein the therapeutic agent is an antibody or fragment thereof.

8. The composition of claim 1, wherein the particles have less than 10% aggregation of the therapeutic agent in suspension or upon reconstitution in water.

9. The composition of claim 1, wherein the particles have less than 10% fragmentation of the therapeutic agent in suspension or upon reconstitution in water.

10. The composition of claim 1, wherein the particles have less than 50% change in charge variants of the therapeutic agent compared to the therapeutic agent prior to particle formation in suspension or upon reconstitution in water.

11. The composition of claim 1, wherein the particles are formed by a method comprising:

providing droplets comprising an aqueous first liquid and an antibody or fragment thereof;

contacting the droplets with an organic solvent, wherein the droplets float or do not float on the organic solvent; and allowing the droplets to dry, thereby forming the particles.

12. The composition of claim 11, wherein the particles have less than 10% by weight of the aqueous first liquid remaining after drying.

13. The composition of claim 11, wherein the particles have less than 10% by weight of the organic solvent remaining after drying.

14. The composition of claim 11, wherein the aqueous first liquid is selected from the group consisting of water, 0.9% saline, lactated Ringer's solution, dextrose 5%, and a buffer.

15. The composition of claim 11, wherein the organic solvent is selected from the group consisting of benzyl benzoate, acetone, ethyl lactate, dimethyl isosorbide, dimethyl sulfoxide, glycofurol, diglyme, methyl tert-butyl ether, polyethylene glycol, 2-pyrrolidone, tetrahydrofurfuryl alcohol, trigylcerides, methyl acetate, ethyl acetate, propyl acetate, butyl acetate, amyl acetate, chloroform, dichloromethane, ethanol, methanol, propanol, butanol, acetonitrile, diethyl ether, diglyme, 1,2-dimethoxyethane, dimethylformamide, pentane, toluene, and any combination thereof.

16. The composition of claim 1, wherein the salt is selected from the group consisting of sodium chloride, calcium chloride, potassium chloride, sodium hydroxide, magnesium sulfate, sodium glucoheptonate, sodium pertechnetate, and guanidine hydrochloride.

17. The composition of claim 1, wherein the amino acid is selected from the group consisting of alanine, aspartic acid, cysteine, isoleucine, glutamic acid, leucine, methionine, phenylalanine, pyrrolysine, serine, selenocysteine, threonine, tryptophan, tyrosine, valine, asparagine, L-arginine, histidine, glycine, glutamine, or a combination thereof.

18. The composition of claim 1, wherein the surfactant is selected from the group consisting of polysorbate, magnesium stearate, sodium dodecyl sulfate, polyethylene glycol nonaphenyl ether, glycerin, or polyoxyethylated castor oil.

19. The composition of claim 1, wherein the carbohydrate is selected from the group consisting of dextran, trehalose, sucrose, agarose, mannitol, lactose, sorbitol, or maltose.

* * * * *